United States Patent
Fink et al.

(10) Patent No.: US 6,197,798 B1
(45) Date of Patent: Mar. 6, 2001

(54) AMINO-BENZOCYCLOALKANE DERIVATIVES

(75) Inventors: Cynthia A. Fink, Lebanon; Gary M. Ksander, Milford; Paivi J. Kukkola, Whitehouse Station, all of NJ (US); Eli M. Wallace, Chapel Hill, NC (US); Mahavir Prashad, Montville, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/357,041

(22) Filed: Jul. 20, 1999

Related U.S. Application Data
(60) Provisional application No. 60/155,243, filed on Jul. 21, 1998.

(51) Int. Cl.[7] .................. A61K 31/44; A61K 31/17; C07D 333/32; C07C 261/00; C07C 233/00
(52) U.S. Cl. .................. 514/354; 514/378; 514/445; 514/596; 514/602; 514/617; 546/323; 548/248; 549/65; 560/27; 564/48; 564/92; 564/155
(58) Field of Search .................. 546/323; 514/354, 514/375, 445, 596, 602, 617; 548/248; 549/65; 560/27; 564/48, 92, 155

(56) References Cited

U.S. PATENT DOCUMENTS

| | | |
|---|---|---|
| 5,053,430 | 10/1991 | Grauert et al. . |
| 5,597,826 | 1/1997 | Howard et al. . |
| 5,675,024 | 10/1997 | Teng et al. . |
| 5,776,951 | 7/1998 | Arrowsmith et al. . |
| 5,958,927 | 9/1999 | Peglion et al. . |
| 5,998,623 | 12/1999 | Urban . |

FOREIGN PATENT DOCUMENTS

| | | |
|---|---|---|
| 701 819 A2 | 3/1996 | (EP) . |
| WO 95/04713 | 2/1995 | (WO) . |
| WO 96/21640 | 7/1996 | (WO) . |
| WO 96/23760 | 8/1996 | (WO) . |
| WO 96/36596 | 11/1996 | (WO) . |
| WO 96/40640 | 12/1996 | (WO) . |
| WO 97/19052 | 5/1997 | (WO) . |
| WO 97/24116 | 7/1997 | (WO) . |
| WO 98/04521 | 2/1998 | (WO) . |
| WO 00/32582 | 6/2000 | (WO) . |

OTHER PUBLICATIONS
Abstract of JP 10097602–A, 1998.

*Primary Examiner*—Deborah C. Lambkin
(74) *Attorney, Agent, or Firm*—Norbert Gruenfeld

(57) ABSTRACT

Compounds of the formula I

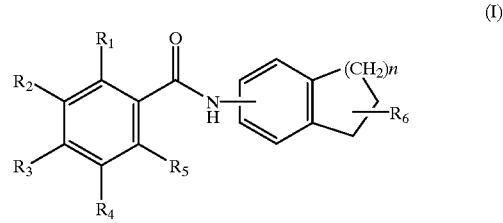

wherein $R_2$—C, $R_3$—C, $R_4$—C or $R_5$—C may be replaced by N; and wherein n is 1, 2 or 3;

$R_1$ is aryl, cycloalkyl or heterocyclyl;

$R_2$, $R_3$, $R_4$ and $R_5$ are independently hydrogen, optionally substituted alkyl, halo, amino, substituted amino, trifluoromethyl, cyano, carboxyl, alkoxycarbonyl, aralkoxycarbonyl, (alkyl, aryl or aralkyl)-thio, (alkyl, aryl or aralkyl)-oxy, acyloxy, (alkyl, aryl or aralkyl)-aminocarbonyloxy; or any two of $R_2$, $R_3$, $R_4$ and $R_5$ at adjacent positions are alkylenedioxy;

$R_6$ is hydrogen, optionally substituted alkyl, amino, substituted amino, acylamino,

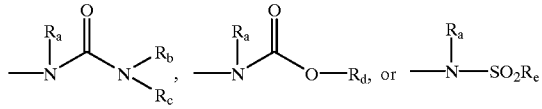

wherein $R_a$ is hydrogen or optionally substituted alkyl, $R_b$ and $R_c$ are independently hydrogen, optionally substituted alkyl, cycloalkyl, aryl or heterocyclyl; or $R_b$ and $R_c$ together represent lower alkylene or lower alkylene interrupted by O, S, or N—(H, alkyl or aralkyl);

$R_d$ is optionally substituted alkyl, cycloalkyl, aryl or heterocyclyl; and $R_e$ is optionally substituted alkyl, aryl, heterocyclyl, cycloalkyl, amino or substituted amino;

and pharmaceutically acceptable salts thereof; and enantiomers thereof; which are useful as inhibitors of microsomal triglyceride transfer protein (MTP) and of apolipoprotein B (ApoB) secretion.

16 Claims, No Drawings

AMINO-BENZOCYCLOALKANE DERIVATIVES

This application claims the benefit of provisional application No. 60/155,243 filed Jul. 21, 1998, which was converted from application Ser. No. 09/120,017, and which is incorporated herein by reference.

SUMMARY OF THE INVENTION

The present invention relates to the benzocycloalkane substituted amide derivatives described herein which are particularly useful as inhibitors of microsomal triglyceride transfer protein (MTP) and of apolipoprotein B (Apo B) secretion, methods for preparation thereof, pharmaceutical compositions comprising said compounds, a method of inhibiting MTP and Apo B secretion and of treating conditions in mammals which are responsive to MTP inhibition or inhibition of Apo B secretion using said compounds or pharmaceutical compositions comprising said compounds of the invention.

DETAILED DESCRIPTION OF THE INVENTION

The invention relates to the compounds of formula I

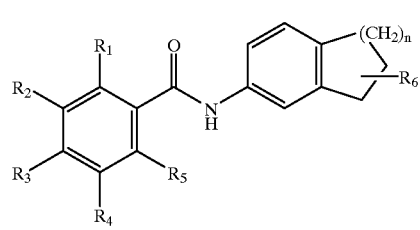
(I)

wherein $R_2$—C, $R_3$—C, $R_4$—C or $R_5$—C may be replaced by N; and wherein n is 1, 2 or 3;

$R_1$ is aryl, cycloalkyl or heterocyclyl;

$R_2$, $R_3$, $R_4$ and $R_5$ are independently hydrogen, optionally substituted alkyl, halo, amino, substituted amino, trifluoromethyl, cyano, carboxyl, alkoxycarbonyl, aralkoxycarbonyl, (alkyl, aryl or aralkyl)-thio, (alkyl, aryl or aralkyl)-oxy, acyloxy, (alkyl, aryl or aralkyl)-aminocarbonyloxy; or any two of $R_2$, $R_3$, $R_4$ and $R_5$ at adjacent positions are alkylenedioxy;

$R_6$ is hydrogen, optionally substituted alkyl, amino, substituted amino, acylamino,

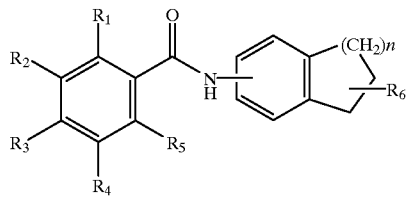

wherein $R_a$ is hydrogen or optionally substituted alkyl, $R_b$ and $R_c$ are independently hydrogen, optionally substituted alkyl, cycloalkyl, aryl or heterocyclyl; or $R_b$ and $R_c$ together represent lower alkylene or lower alkylene interrupted by O, S, or N—(H, alkyl or aralkyl);

$R_d$ is optionally substituted alkyl, cycloalkyl, aryl or heterocyclyl; and $R_e$ is optionally substituted alkyl, aryl, heterocyclyl, cycloalkyl, amino or substituted amino;

and pharmaceutically acceptable salts thereof; and enantiomers thereof.

Compounds of formula I are useful as inhibitors of microsomal triglyceride transfer protein (MTP) and of apolipoprotein B (ApoB) secretion and accordingly for the prevention and treatment of MTP and Apo B dependent conditions.

A particular embodiment of the invention relates to the compounds of formula I'

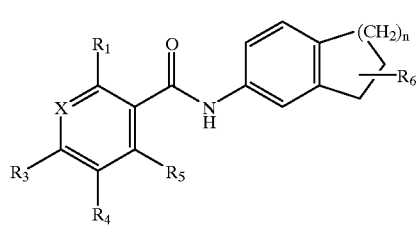
I' wherein $R_2$—C, $R_3$—C, $R_4$—C or $R_5$—C may be replaced by N; and wherein n, and $R_1$–$R_6$ have meaning as defined above; pharmaceutically acceptable salts thereof; and enantiomers thereof.

A specific embodiment of the invention relates to the compounds of formula Ia

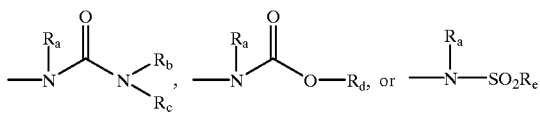
Ia wherein

X is $R_2$—C or N; and n, and $R_1$–$R_6$ have meaning as defined above.

Particular embodiments of the invention relate to the compounds of formula Ia wherein:

(a) $R_1$ represents aryl;

(b) $R_1$ represents heterocyclyl, in particular aromatic heterocyclyl (heteroaryl);

(c) n is one;

(d) X is $R_2$—C;

(e) X is N;

(f) $R_6$ is amino, substituted amino or acylamino;

(g) $R_6$ is

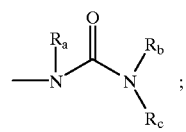
;

(h) $R_6$ is

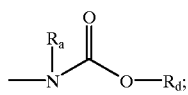

(i) $R_6$ is

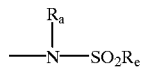

Preferred are the compounds of formula Ia wherein n is 1; $R_1$ is monocyclic aryl or heteroaryl; X is $R_2$—C or N; $R_2$, $R_3$, $R_4$ and $R_5$ are independently hydrogen, lower alkyl halo, trifluoromethyl, lower alkoxy or amino; and $R_6$ is amino, substituted amino, acylamino,

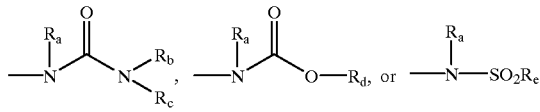

wherein $R_a$ is hydrogen; $R_b$ and $R_c$ are independently hydrogen, lower alkyl, aralkyl, aryl, heteroaryl or heteroaralkyl; or $R_b$ and $R_c$ together with the nitrogen represent piperidino, morpholino, pyrrolidino, or N-lower alkylpiperazino; $R_d$ and $R_e$ are lower alkyl, aralkyl, aryl, heteroaryl or heteroaralkyl; and pharmaceutically acceptable salts thereof.

Preferred are the compounds of formula I, I' or Ia wherein $R_6$ is located on the 5-, 6- or 7-membered saturated ring (n=1, 2, or 3) at a position not directly adjacent to the ring junction (non-benzylic position).

A particular aspect of the invention relates to the compounds of formula I wherein $R_2$—C, $R_3$—C, $R_4$—C or $R_5$—C may be replaced by N;

wherein n is 1, 2 or 3;

$R_1$ is phenyl or thienyl which in each case is unsubstituted or substituted by a substituent selected from the group consisting of lower alkyl, lower alkoxy, halo, trifluoromethyl, cyano, and trifluoromethoxy;

$R_2$, $R_3$, $R_4$ and $R_5$ are independently hydrogen, lower alkyl, lower alkoxy, halo, trifluoromethyl, amino, lower alkylamino, di-lower alkyl amino, or lower alkanoyl-amino;

$R_6$ is amino, phenyl-lower alkyl-amino, lower alkanoyl-amino, lower alkanoyl-amino in which the alkyl group of the alkanoyl group is substituted by phenyl, by lower alkoxy, by phenoxy, by lower alkylthio, by phenylthio, by di-lower alkylamino, by morpholino, by thiomorpholino, by piperazino, or by 4-lower alkyl-piperazino, or is N-methyl-N'-lower alkanoyl-amino, benzoyl-amino, or isoxazolylcarbonyl-amino in which isoxazoyl is unsubstituted or substituted by lower alkyl, or is wherein $R_a$ is hydrogen or alkyl, $R_b$ and $R_c$ are independently hydrogen, lower alkyl, 5- to 7-membered cycloalkyl, or phenyl; or $R_b$ and $R_c$ together are morpholino, thiomorpholino or lower alkylene;

$R_d$ is lower alkyl, lower alkyl substituted by lower alkoxy, by lower alkoxy-lower alkoxy, by morpholino, by thiomorpholino, by 2-oxo-1-pyrrolidino, by pyridyl, by phenyl, or by phenyl which is substituted by a substituent selected from halo, trifluoromethyl, lower alkyl, and lower alkoxy, or is phenyl, phenyl substituted by substituent selected from halo, trifluoromethyl, lower alkyl, and lower alkoxy, or is 5- to 7-membered cycloalkyl, or pyranyl; and $R_e$ is lower alkyl, phenyl-lower alkyl, phenyl which is unsubstituted or substituted by a group selected from lower alkyl, lower alkoxy, halo, trifluoromethyl, and lower alkane-sulphonyl, or is naphthyl, thienyl, furyl, isoxazolyl, imidazolyl or quinolinyl each of which is unsubstituted or substituted by a group selected from lower alkyl, halo and trifluoromethyl, or is lower alkylamino, di-lower alkyl-amino or 5- to 7-membered cycloalkyl-amino;

and pharmaceutically acceptable salts thereof; and enantiomers thereof.

A particular aspect of the invention relates to the indane derivatives of formula Ib wherein Ar is monocyclic aryl or heteroaryl;

X is $R_2$—C or N;

$R_2$, $R_3$, $R_4$ and $R_5$ are independently hydrogen, lower alkyl, halo, trifluoromethyl, cyano, or lower alkoxy;

and $R_6$ has meaning as defined above in each case.

Preferred are the said compounds of formula Ib wherein Ar is phenyl or phenyl substituted by fluoro, chloro, trifluoromethyl, cyano or lower alkyl; X is N or $R_2$—C; $R_2$, $R_3$, $R_4$ and $R_5$ are independently hydrogen, lower alkyl, lower alkoxy, halo or trifluoromethyl; and $R_6$ has meaning as defined above in each case.

Further preferred are the compounds of formula Ic

Ic wherein $R_2$, $R_3$ and $R_4$ are independently hydrogen, $C_1$–$C_4$-alkyl, $C_1$–$C_4$alkoxy, trifluoromethyl, chloro or fluoro; $R_7$ is trifluoromethyl, chloro or cyano; and $R_6$ is wherein $R_d$ is $C_1$–$C_4$-alkyl; and $R_e$ is $C_1$–$C_4$-alkyl, monocyclic carbocyclic aryl or heterocyclic aryl.

Further preferred are the compounds of formula Ic wherein $R_2$ is methyl; $R_3$ is hydrogen; $R_4$ is hydrogen or methyl; $R_7$ is trifluoromethyl or chloro; $R_d$ is $C_1$–$C_4$-alkyl; and $R_e$ is $C_1$–$C_4$-alkyl or thienyl.

A particular embodiment relates to the compounds of formula Ic wherein $R_2$ is methyl; $R_3$ is hydrogen; $R_4$ is hydrogen or methyl; $R_6$ is —NHSO$_2$R$_e$ wherein $R_e$ is methyl or thienyl; and $R_7$ is trifluoromethyl.

Another embodiment relates to the compounds of formula Ic wherein $R_2$ is methyl; $R_3$ is hydrogen; $R_4$ is hydrogen or methyl; $R_6$ is wherein $R_d$ is methyl; and $R_7$ is trifluoromethyl.

Also preferred in all of the above, is the more active enantiomer in which the carbon atom bearing the substituent $R_6$ (if $R_6$ is not hydrogen) has either the (R) or the (S)-configuration.

Listed below are definitions of various terms used to describe the compounds of the instant invention. These definitions apply to the terms as they are used throughout the specification (unless they are otherwise limited in specific instances either individually or as part of a larger group).

The term "lower" referred to herein in connection with organic radicals or compounds respectively generally defines, if not defined differently, such with up to and including 7, preferably up and including 4 and advantageously one or two carbon atoms. Such may be straight chain or branched.

The term "optionally substituted alkyl" refers to unsubstituted or substituted straight or branched chain hydrocarbon groups having 1 to 20 carbon atoms, preferably lower alkyl of 1 to 7 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like.

The term "substituted alkyl" refers to alkyl groups substituted by one or more of the following groups: halo (such as CCl$_3$ or CF$_3$), hydroxy, alkoxy, alkoxyalkoxy, aryloxy, cycloalkyl, alkanoyl, alkanoyloxy, amino, substituted amino, alkanoylamino, thiol, alkylthio, arylthio, alkylthiono, alkylsulfonyl, arylsulfonyl, heteroarylsulfonyl, aminosulfonyl, nitro, cyano, carboxy, carbamyl, alkoxycarbonyl, aryl, aralkoxy, guanidino, heterocyclyl (e.g., indolyl, imidazolyl, furyl, thienyl, thiazolyl, pyrrolidyl, pyridyl, pyrimidyl), and the like.

The term "lower alkyl" refers to those alkyl groups as described above having 1 to 7, preferably 1 to 4 carbon atoms.

The term "halogen" or "halo" refers to fluorine, chlorine, bromine and iodine.

The term "haloalkyl" refers to alkyl which mono- or polysubstituted by halo, such as trifluoromethoxy.

The term "alkylene" refers to a straight chain bridge of 1 to 6 carbon atoms connected by single bonds (e.g., —(CH$_2$)$_x$— wherein x is 1 to 6) which may be substituted with 1 to 3 lower alkyl groups.

The term "alkylene interrupted by O, S, N—(H, alkyl or aralkyl)" refers to a straight chain of 2 to 6 carbon atoms which is interrupted by O, S, N—(H, alkyl or aralkyl), such as (m)ethyleneoxy(m)ethylene, (m)ethylenethio(m)ethylene, or (m)ethyleneimino(m)ethylene.

The term "cycloalkyl" refers to cyclic hydrocarbon groups of 3 to 8 carbon atoms such as cyclopentyl, cyclohexyl or cycloheptyl.

The term "alkoxy" or "alkyloxy" refers to alkyl-O—.

The term "alkanoyl" refers to alkyl-C(O)—.

The term "alkanoyloxy" refers to alkyl-C(O)—O—.

The terms "alkylamino" and "dialkylamino" refer to (alkyl)NH— and (alkyl)$_2$N—, respectively.

The term "alkanoylamino" refers to alkyl-C(O)—NH—.

The term "alkylthio" refers to alkyl-S—.

The term "alkylthiono" refers to alkyl-S(O)—.

The term "alkylsulfonyl" refers to alkyl-S(O)$_2$—.

The term "carbamyl" refers to —C(O)-amino or —C(O)-substituted amino.

The term "alkoxycarbonyl" refers to alkyl-O—C(O)—.

The term "acyl" refers to alkanoyl, aroyl, heteroaryol, aryl-alkanoyl, heteroarylalkanoyl, and the like.

The term "aryl" or "ar", refers to monocyclic or bicyclic aromatic hydrocarbon groups having 6 to 12 carbon atoms in the ring portion, such as phenyl, naphthyl, tetrahydronaphthyl, and biphenyl groups, each of which may optionally be substituted by one to four substituents such as alkyl, halo, trifluoromethyl, hydroxy, alkoxy, halo-alkyl, alkanoyl, alkanoyloxy, amino, substituted amino, alkanoylamino, thiol, alkylthio, nitro, cyano, carboxy, carboxyalkyl, carbamyl, alkoxycarbonyl, alkylthiono, alkylsulfonyl, aminosulfonyl, heterocyclyl and the like.

The term "aralkyl" refers to an aryl group linked to an alkyl group, such as benzyl.

The term "aralkoxy" refers to an aryl group linked to an alkoxy group, such as locozyloxy.

The term "arylsulfonyl" refers to aryl-SO$_2$—.

The term "aroyl" refers to aryl-CO—.

The term "heterocyclyl" refers to an optionally substituted, fully saturated or unsaturated, aromatic or non-aromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b] pyridinyl), dihydroisoindolyl, dihydroquinazolinyl (such as 3,4-dihydro-4-oxo-quinazolinyl) and the like.

Exemplary tricyclic heterocyclic groups include carbazolyl, benzidolyl, phenanthrolinyl, acridinyl, phenanthridinyl, xanthenyl and the like. The term "heterocyclyl" also includes substituted heterocyclic groups. Substituted heterocyclic groups refer to heterocyclic groups substituted with 1, 2 or 3 of the following:

(a) alkyl;
(b) hydroxy (or protected hydroxy);
(c) halo;
(d) oxo (i.e. =O);
(e) amino or substituted amino;
(f) alkoxy;
(g) cycloalkyl;
(h) carboxy;
(i) heterocyclooxy;
(j) alkoxycarbonyl, such as unsubstituted lower alkoxycarbonyl;
(k) carbamyl, alkylcarbamyl, arylcarbamyl, dialkylcarbamyl;
(l) mercapto;
(m) nitro;
(n) cyano;
(o) sulfonamido, sulfonamidoalkyl or sulfonamidodialkyl;
(p) aryl;
(q) alkylcarbonyloxy;
(r) arylcarbonyloxy;
(s) arylthio;
(t) aryloxy;
(u) alkylthio;
(v) formyl;
(w) arylalkyl; or
(x) aryl substituted with alkyl, cycloalkyl, alkoxy, hydroxy, amino, alkylamino, dialkylamino or halo.

The term "heterocyclooxy" denotes a heterocyclic group bonded through an oxygen bridge.

The term "heteroaryl" "or heteroar" refers to an aromatic heterocycle, for example monocyclic or bicyclic aryl, such as pyrrolyl, pyrazolyl, imidazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl, and the like, optionally substituted by e.g., lower alkyl, lower alkoxy or halo.

The term "heteroarylsulfonyl" refers to heteroaryl-$SO_2$—.

The term "heteroaroyl" refers to heteroaryl-CO—.

The term "acylamino" refer to acyl-NH—.

The term "substituted amino" refers to amino mono- or, independently, disubstituted by alkyl, aralkyl, aryl, heteroaryl, cycloalkyl, cycloalkylalkyl, heteroaralkyl, or disubstituted by lower alkylene or lower alkylene interrupted by O, S, N—(H, alkyl, aralkyl) and the like.

Pharmaceutically acceptable salts of any acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)methylammonium salts.

Similarly acid addition salts, such as of mineral acids, organic carboxylic, and organic sulfonic acids e.g., hydrochloric acid, methanesulfonic acid, maleic acid, are possible provided a basic group, such as amino or pyridyl, constitutes part of the structure.

The compounds of the invention depending on the nature of the substituents, possess one or more asymmetric carbon atoms, and therefore exist as racemates and the (R) and (S) enantiomers thereof. All are within the scope of the invention.

The compounds of the invention, as illustrated for certain compounds of formula Ia wherein n is 1, can be prepared by coupling a protected compound of e.g. formula II

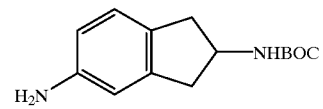

II wherein BOC is the protecting group t-butoxycarbonyl, with e.g, an activated carboxyl derivative, e.g. a compound of formula III

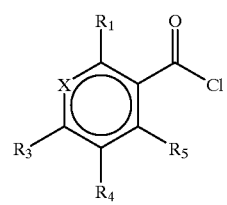

III wherein $R_1$–$R_5$ and X have meaning as defined above, in the presence of a base such as N-methylmorpholine, diisopropylethylamine or pyridine to provide compounds of the formula IV

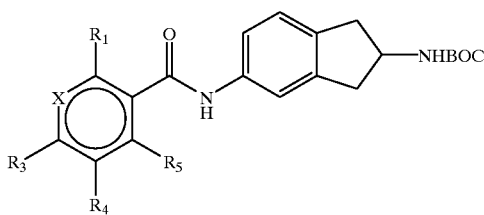

Compounds of formula IV are then reacted with an acid such as $HCO_2H$, to form compounds of formula V

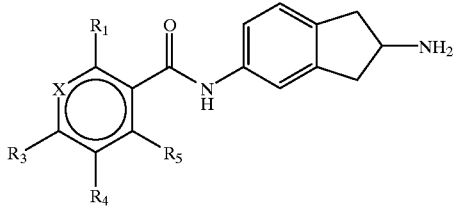

Compounds of formula V are then treated with an electrophile corresponding to the amino substituent in $R_6$, such as an appropriately substituted sulfonyl chloride (e.g., phenylsulfonyl chloride), a chloroformate (e.g., methyl chloroformate), an acid chloride (e.g., acetyl chloride), an isocyanate (e.g., phenyl isocyanate), an isothiocyanate (e.g., phenyl isothiocyanate) and the like, optionally in the presence of a base such as sodium hydroxide or triethylamine to form compounds of formula Ia. Compounds of formula V may be N-alkylated according to methods well known in the art prior to treatment with an electrophile.

Compounds of formula II are prepared by acid hydrolysis of e.g., N-(5-nitro-indan-2-yl)acetamide followed by protection of the resulting amine with BOC-anhydride and subsequent reduction, e.g., by catalytic hydrogenation, of the nitro group.

Biarylcarboxylic acids corresponding to the compounds of formula III can be prepared e.g. as described in Bioorg. Med. Chem. Lett. 7 (13), 1595 (1997) or as illustrated herein.

Compounds of formula III wherein $R_1$ is aryl or heteroaryl are prepared as shown in the scheme below by palladium catalyzed aryl-aryl coupling of aryl boronic acids of formula VI with bromo, iodo or trifluomethylmethanesulfonyloxy-substituted arylcarboxylic acid esters of formula VII. Subsequent hydrolysis of the ester group of resulting compounds of formula VIII with sodium hydroxide followed by reaction with a chlorinating agent such as oxalyl chloride lives acid chlorides of formula III.

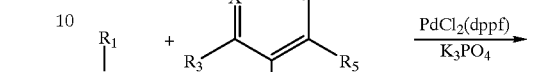

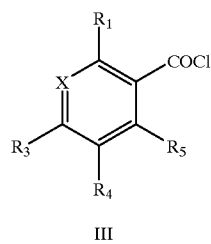

Compounds of formula V wherein $R_1$ is aryl or heteroaryl may also be prepared using the alternative synthesis below:

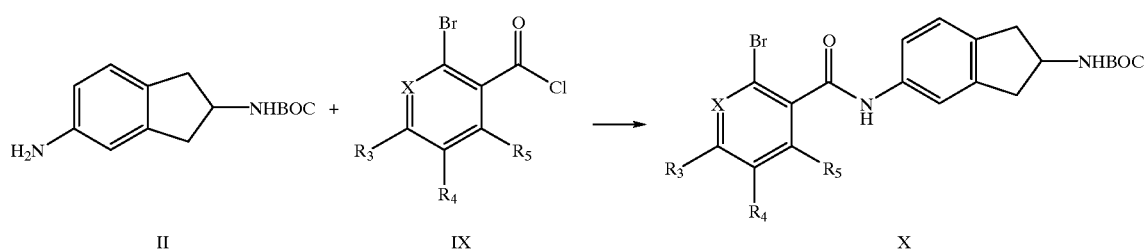

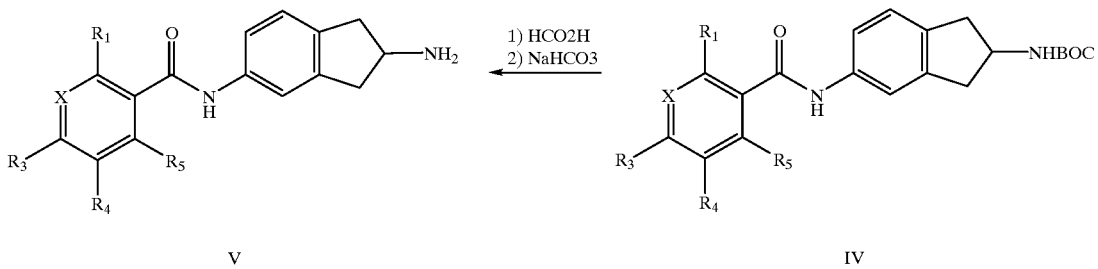

As shown above, amines of formula II are acylated with compounds of formula IX in the presence of a base such as N-methylmorpholine, diisopropylethylamine, triethylamine or pyridine to give compounds of the formula X. Palladium catalyzed aryl-aryl coupling of aryl boronic acids of formula ($R_1$—B(OH)2) with aryl bromides of the formula X (or iodides or triflates) gives compounds of formula IV. Acid, e.g., formic acid, treatment readily deprotects the nitrogen to give compounds of formula V.

Compounds of formula I wherein $R_6$ is disubstituted amino may also be prepared by the alternative synthesis illustrated below:

Compounds of formula I wherein $R_6$ is

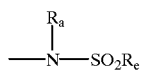

are similarly prepared.

Chiral compounds of the invention can be prepared as follows:

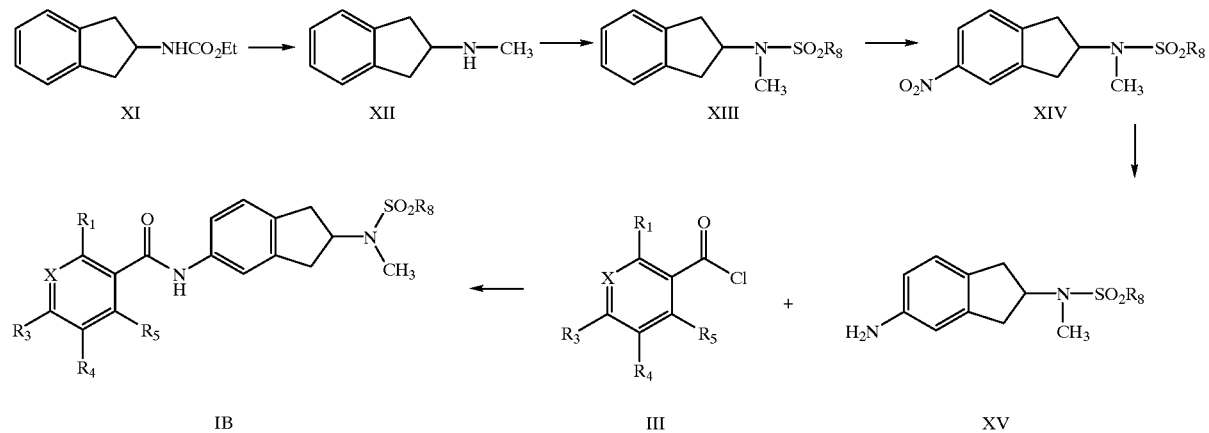

2-(Ethoxycarbonylamino)-indanes of formula XI are reduced with a reducing agent such as lithium aluminum hydride to give the N-methylamine of formula XII. Acylation, e.g., with sulfonyl chlorides, gives compounds of the formula XIII. Nitration followed by catalytic hydrogenation gives amines of the formula XV (via intermediate XIV). Acylation of compounds of formula XV with compounds of the formula III in the presence of diisopropylethyl amine gives compounds of formula I where $R_6$ is $$\begin{array}{c} R_a \\ | \\ —N—SO_2R_e \end{array}$$

(a) reducing (1S-trans)- or (1R-trans)-hydroxy-2-amino-6-nitroindane wherein the amino group is in protected form to the corresponding (R) or (S)-enantiomer of 2,6-diaminoindane in which the 2-amino group is in protected form;

(b) condensing said (R) or (S) enantiomer with a reactive derivative of a carboxylic acid, e.g., a compound of formula III, and removing the amino protecting group to obtain the (R) or (S) enantiomer of a compound of formula V; and (c) subsequently N-derivatizing a said enantiomer to a compound of formula Ia wherein $R_6$ is derivatized amino as defined herein for $R_6$.

For example, chiral compounds of the invention, can be prepared e.g., by acylating a protected amine of e.g., formula XVI

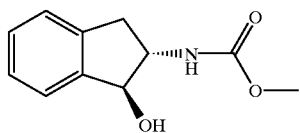

XVI with acetyl chloride to form compounds of formula XVII

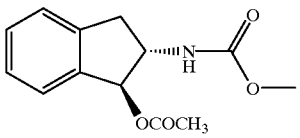

XVII

Compounds of formula XVII are nitrated with nitric acid, trifluoroacetic acid and trifluoroacetic anhydride to form compounds of formula XVIII

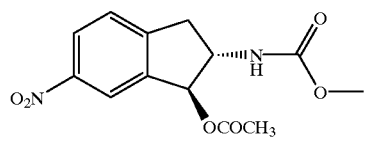

XVIII

Compounds of formula XVIII are saponified with sodium hydroxide to form compounds of formula XIX

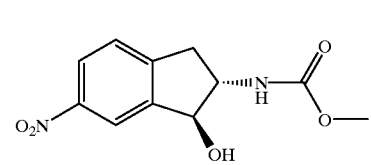

XIX

Compounds of formula XIX are reduced with hydrogen in the presence of Pd/C catalyst to form compounds of formula XX

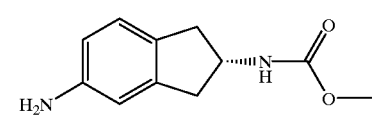

XX

Compounds of the formula XX are coupled with compounds of formula III in the presence of a base such as N-methylmorpholine, diisopropylethylamine, triethylamine or pyridine to provide compounds of formula XXI

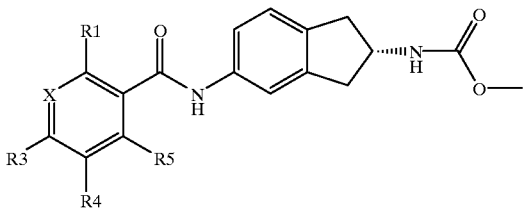

XXI

Compounds of formula XXI are treated with e.g., trimethylsilyl iodide to form the chiral compounds of the formula V'

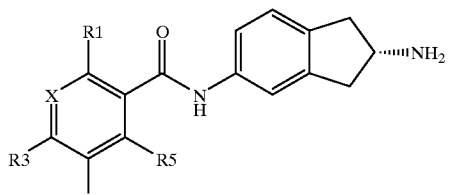

V'

Amines of formula V' are then treated with an electrophile as previously described to form other N-substituted chiral compounds corresponding to formula Ia.

The opposite enantiomer is similarly prepared from the diastereoisomer of the compound of formula XVI.

Alternatively, e.g. 5-bromo-2-aminoindane is prepared as described in example 17 by bromination of 2-aminoindane which is resolved with D- or L-camphorsulfonic acid, and the resulting chiral amine is protected as e.g. the N-methoxycarbonyl derivative. Reaction with benzophenone imine (in a Buchwald condensation, Tetrahedron Letters 36, 6367, 1997) yields the corresponding chiral compound of formula XV (or its enantiomer).

A method for the preparation of enantiomers of the compounds of the invention, e.g. of formula Ib, thus comprises:

(a) resolving 5-bromo-2-aminoindane with either (R) or (S)-10-camphorsulfonic acid to obtain either chiral (R)- or (S)-5-bromo-2-aminoindane;

(b) protecting the resulting (R)- or (S)-5-bromo-2-aminoindane with e.g. an N-alkoxycarboxyl protecting group;

(c) reacting a said N-alkoxycarbonyl-5-bromo-2-aminoindane with benzophenone imine under conditions of a Buchwald condensation;

(d) cleaving the resulting 5-benzophenoneimine derivative by catalytic hydrogenation or treatment with acid;

(e) condensing the resulting 2-protected amino-5-aminoindane with a reactive derivative of a carboxylic acid, e.g. of the formula III wherein $R_1$, $R_3$–$R_5$ and X have meaning as defined herein, and optionally removing the amino protecting group to obtain the corresponding (R) or (S) enantiomer of a compound of formula V; and (f) N-derivatizing a said compound to obtain a compound of formula Ib wherein $R_6$ is derivatized amine as defined herein.

Illustrative of step (a), R-2-amino-5-bromoindane can be prepared e.g. by treating racemic 2-amino-5-bromoindane with 1(S)-10-camphorsulfonic acid, selectively crystallizing and purifying the resulting (R,S) diastereomeric salt, and then liberating, by treatment with a base, (R)-2-amino-5-bromoindane which is substantially free of the (S)-isomer.

In turn, racemic 2-amino-5-bromoindane is commercially available or can be prepared by converting ninhydrin to 1,3-dioxo-2-hydroxyiminoindane followed by catalytic hydrogenation.

The Buchwald amination by condensation of e.g. 5-bromo-2-carbomethoxyaminoindane with benzophenone imine can be carried out similarly to the procedures described in Tetrahedron Letters 38, 6367 (1997). The amination is carried out in the presence of a palladium catalyst, a ligand and a base in an inert solvent such as toluene. Palladium catalysts include tris(dibenzylideneacetone)dipalladium (O), bis(dibenzylideneacetone)palladium (O) and palladium acetate. Preferred ligands include 2,2'-bis(diphenylphosphino-1,1'-binaphthyl, bis(2-diphenylphosphinophenyl)ether and 1,1'-bis(diphenylphosphino)ferrocene. Preferred bases include sodium methoxide and sodium isopropoxide, the use of which is not disclosed in Tetrahedron Letters 38, 6367 (1997).

The resulting benzophenone imines are cleaved to the free amines, e.g. by treatment with dilute acid, such as 2N hydrochloric acid.

The other steps are carried out as described herein.

In starting compounds and intermediates which are converted to the compounds of the invention in a manner described herein, functional groups present, such as amino, thiol, carboxyl, and hydroxy groups, are optionally protected by conventional protecting groups that are common in preparative organic chemistry. Protected amino, thiol, carboxyl, and hydroxy groups are those that can be converted under mild conditions into free amino and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, for example, in J. F. W. McOmie, "Protective Groups in Organic Chemistry", Plenum Press, London, New York, 1973, T. W. Greene, "Protective Groups in Organic Synthesis, third edition", Wiley, New York, 1999.

In the processes cited herein, reactive functional derivatives of carboxylic acids represent, for example, anhydrides (especially mixed anhydrides), acid halides, acid azides, lower alkyl esters, and activated esters thereof. Mixed anhydrides are preferably such from pivalic acid, or a lower alkyl (ethyl, isobutyl) hemiester of carbonic acid; acid halides are for example chlorides or bromides; activated esters for example succinimido, phthalimido or 4-nitrophenyl esters; lower alkyl esters are for example the methyl or ethyl esters.

Depending on the choice of starting materials and methods, the new compounds may be in the form of one of the possible isomers or mixtures thereof, for example, as substantially pure geometric (cis or trans) isomers, optical isomers (antipodes), racemates, or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization, or resolved by enzymatic resolution.

Any resulting racemates of intermediates can be resolved into the optical antipodes by known methods, e.g., by separation of the diastereoisomeric salts thereof, obtained with an optically active acid or base, and liberating the optically active acidic or basic compound. The amine intermediates can thus be resolved into their optical antipodes e.g., by fractional crystallization of salts of d- or l-carboxylic acids (e.g., d-or l-tartaric acid). Racemic products can also be resolved by chiral chromatography, e.g., high-pressure liquid chromatography using a chiral adsorbent.

Finally, compounds of the invention are either obtained in the free form, or as a salt thereof if salt forming groups are present.

Acidic compounds of the invention may be converted into salts with pharmaceutically acceptable bases, e.g., an aqueous alkali metal hydroxide, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

Compounds of the invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_1$–$C_4$)-alkanecarboxylic acids which, for example, are unsubstituted or substituted by halogen, for example acetic acid, such as saturated or unsaturated dicarboxylic acids, for example oxalic, succinic, maleic or fumaric acid, such as hydroxycarboxylic acids, for example glycolic, lactic, malic, tartaric or citric acid, such as amino acids, for example aspartic or glutamic acid, or with organic sulfonic acids, such as ($C_1$–$C_4$)-alkylsulfonic acids (for example methanesulfonic acid) or arylsulfonic acids which are unsubstituted or substituted (for example by halogen). Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, e.g. to inhibit microsomal triglyceride transfer protein (MTP) and apolipoprotein B (Apo B) secretion, and e.g. for the treatment of disorders responsive thereto, comprising an effective amount of a pharmacologically active compound of the invention, alone or in combination, with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1% to 100%, especially about 0.1 to75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable formulations for topical application, e.g., to the skin and eyes, are preferably aqueous solutions, ointments, creams or gels well known in the art.

The pharmaceutical formulations contain an inhibiting amount of a compound of the invention as defined above, either alone or in combination with another therapeutic agent, e.g., each at an effective therapeutic dose as reported in the art. Such therapeutic agents are well known in the art.

In conjunction with another active ingredient, a compound of the invention may be administered either simultaneously, before or after the other active ingredient, either separately by the same or different route of administration or together in the same pharmaceutical formulation.

The dosage of active compound administered is dependent on the species of warm-blooded animal (mammal), the body weight, age and individual condition, and on the form of administration. A unit dosage for oral administration to a mammal of about 50 to 70 kg may contain between about 10 and 1000 mg, advantageously between about 25 and 500 mg of the active ingredient.

The present invention also relates to methods of using the compounds of the invention and their pharmaceutically acceptable salts, or pharmaceutical compositions thereof, in mammals for the prevention or treatment of elevated levels of MTP and of Apo B and conditions related thereto. The present invention also relates to the use of a compound according to the instant invention or a pharmaceutically acceptable salt thereof for the manufacture of a medicament for the prevention or treatment of diseases or conditions associated with elevated levels of MTP and of Apo B.

The compounds of the invention are inhibitors of microsomal triglyceride transfer protein (MTP) and of apolipoprotein B (Apo B) secretion and are thus useful for lowering serum lipid levels, including serum triglyceride and serum cholesterol levels. Such compounds are therefore useful for the treatment and prevention of hyperlipedemia, hypercholesterolemia and hypertriglyceridemia, and diseases associated therewith, e.g., cardiovascular diseases including cardiac ischemia, atherosclerosis and its clinical sequelae, as well as obesity, pancreatitis and diabetes.

The above-cited properties are demonstrable in vitro and in vivo tests using advantageously mammals, e.g., rats, mice, dogs, monkeys, and isolated cells or enzyme preparations. Said compounds can be applied in vitro in the form of solutions, e.g., aqueous solutions, and in vivo advantageously orally, topically or parenterally, e.g., intravenously. The dosage in vitro may range from about $10^{-5}$ to $10^{-9}$ molar concentrations. The dosage in vivo may range, depending on the route of administration, between about 1 and 100 mg/kg. The tests are generally known in the art. For in vivo evaluation, the compounds are generally administered as a solution or suspension, e.g., as a suspension in 3% cornstarch.

The activity of a compound according to the invention can be assessed by the following methods:

The inhibition of the cellular secretion of Apo B is determined as follows:

Hep G2 cells are maintained in T-75 culture flasks (Corning) in Dulbecco's modified Eagles Medium (DMEM; Gibco-BRL) supplemented with 10% fetal calf serum Gibco-BRL) in a humidified atmosphere containing 5% carbon dioxide until they are confluent. For testing compounds, Hep G2 cells from the T-75 maintenance flasks are harvested and seeded in 96-well culture plates (Corning) and are grown for 72 hours (approximately 80% confluent). Test compound is dissolved at 1 mg/ml (w/v;1–5 mM) in dimethyl sulfoxide DMSO; Sigma) as stock solution. Prior to use, the stock solution of compound is diluted to 133 $\mu$M with DMSO and diluted further with growth medium (DMEM containing 10% fetal calf serum) to obtain 1 $\mu$M of compound in 100 $\mu$L of growth medium. 100 $\mu$L of growth medium containing the test compound is added to separate wells of a 96-well culture plate containing Hep G2 cells. For testing dose response of compound, a stock solution of test compound in DMSO is made at 665 $\mu$M and various dilutions from this solution are made in growth medium to obtain range of concentration of compound from 0.01 $\mu$M to 5 $\mu$M in 100 $\mu$L of growth medium. 100 $\mu$L of the growth medium containing different concentrations of test compound is added to separate wells containing Hep G2 cells. Twenty-four hours later, growth medium is collected and assayed by specific ELISA for apolipoprotein B (Apo B). At the same time Hep G2 cells from wells are assayed for protein (BioRad; cat. # 500-0006) and/or cell viability (Promega; CellTiter 96 Aqueous, cat. # G3581). Inhibitors are identified as compounds that decrease Apo B secretion into the medium without decreasing the total cellular protein and/or cell viability. For performing Apo B ELISA, an antisera for human Apo B is made by immunizing rabbit with purified human Apo B. The antisera is further purified by using an affinity column (CNBr activated Sepharose 4B, Pharmacia) with human LDL as ligand and used as primary antibody for human Apo B. A secondary antibody for Apo B is prepared by conjugating the human Apo B antibody with alkaline phosphatase (Sigma). The ELISA for Apo B is performed as follows. 15 $\mu$L of primary antibody solution prepared against Apo B is diluted to a final volume of 10 mL with coating buffer (containing 15 mM sodium carbonate, 35 mM sodium bicarbonate, 3 mM sodium azide, pH 9.6). 200 $\mu$L of diluted antibody solution is added to each well of a 96 well plate (Maxisorb, Nunc, cat. # 439454). After an overnight incubation at 4° C., the antibody solution is removed.

Nonspecific sites on the plastic well are blocked by adding 300 μL of blocking solution containing phosphate buffered saline (PBS), 1% (w/v) bovine serum albumin (Sigma), pH 7.4) and incubated for 45 minutes at room temperature. After removing blocking solution, 200 μL of dilution buffer (containing PBS/0.05% Tween 20/5 mM decyl sodium sulfate (Acros Organics)/2% BSA, pH 7.4) containing 20 μL of growth medium from Hep G2 cells or 1–30 ng of Apo B standards (prepared in dilution buffer) is added to each well. After 2 hours incubation at 37° C., solution from each well is removed and washed five times with washing buffer (containing PBS and 0.05% Tween 20, pH 7.4). 200 μL of diluted conjugated secondary antibody for Apo B (15 μl diluted to a final volume of 10 mL in dilution buffer) is added to each well. After 2 hours incubation at 37° C., the solution is removed and the well is washed five times with washing buffer. p-nitrophenyl phosphate disodium hexahydrate solution (Sigma, cat. # 104-0) is prepared in substrate buffer (containing 0.95 M diethanolamine/0.5 mM MgCl2/3 mM sodium azide, pH 9.5) at a concentration of 1 mg/ml and 200 μL of substrate solution is added to each well and incubated for 45–60 minutes. Absorbance of each well is read at 405 nm using a Beckman Biomek workstation. Apo B concentration is calculated from a standard curve generated from purified LDL standards that are run in parallel in the same assay. Secreted Apo B values are normalized with the total cellular protein assay and/or cell viability assay.

The inhibition of MTP is measured as follows:

Inhibition of the lipid transfer activity of MTP can be quantitated by measuring the inhibition of transfer of radiolabeled triglyceride from donor vesicles to acceptor vesicles in presence of soluble rat MTP. The procedure for preparing MTP is based on the method of Wetterau and Zilversmit (Biochim. Biophys. Acta (1986) 875:610). Briefly rats are decapitated under ether anesthesia. The liver is placed in ice cold sucrose buffer (contains 0.25M sucrose, 50 mM Tris Hcl, 1 mM EDTA, 0.02% sodium azide, pH 7.4) rinsed several times with the sucrose buffer.

All subsequent steps are performed on ice. A 57% homogenate (120 g/210 mL) of rat liver in 0.25 M sucrose buffer is prepared by using a Potter-Elvehjem homogenizer. The homogenate is then centrifuged at 4° C. for 30 min at 13,000×g to remove large cellular organells. The supernatant is then centrifuged for 90 min at 105,000×g to pellet the microsomes. The pellet is resuspended in 10 mM Tris-HCl buffer pH 8.6. and centrifuged for 90 min at 105,000×g. The washed pellet is then resuspended in 1 mM Tris buffer (pH 8.6) and centrifuged for 2 hrs. The pellet is resuspended in 28.5 mL of 0.25M sucrose solution and 1 mL aliquotes containing 4.2 g of liver are stored frozen at −80° C. until needed. Prior to performing the assay, the thawed pellet is suspended in 12 mL of cold Tris-HCl, 50 mM KCl, 5 mM MgCl, pH 7.4 and 1.2 mL of a 0.54% deoxycholate solution (pH 7.4) is added slowly with gentle mixing. The suspension is kept on ice for 30 min and then centrifuged at 105,000 g for 75 min. The supernatant containing soluble MTP is dialyzed against assay buffer (150 mM Tris-HCl, 40 mM NaCl, 1 mM EDTA, 0.02% NaN$_3$, pH 7.4). The protein content is measured using the Sigma Lowry micro total protein method and reagents (Sigma Cat. # 690A). The rat MTP is diluted with assay buffer to contain 15 μg protein per 50 μL and stored at 4° C.

Donor and acceptor liposomes are prepared as follows. For preparation of donor vesicles, 12.4 mg of egg phosphatidylcholine (Sigma, cat.# P-3556), 5.2 mg of cardiolipin (Sigma, Cat. # C-0563) and 8 mgs of hydroxybutylate toluene are dissolved in 4 mL of chloroform. To this solution, 34.8 μL of $^3$H labeled Triolein (Amersham, Cat. # TRA 191, glycerol tri[1,9-$^3$H]oleate) is added and mixed. 200 μL of this mixture is transferred into a screw cap glass vial, dried under nitrogen and reconstituted in 2 mL of assay buffer. The lipid suspension is sonicated for 30 min at 1.5 setting with pulse at 75 using Branson 450 sonifier in a water bath with ice. For preparation of acceptor vesicles, 18 mg of egg phophatidylcholine and 4 mg of hydroxybutylated toluene is added in 1 mL of chloroform. A 200 μL aliquot from this mixture is transferred into a screw cap glass vial. To this vial, 10 μL of Triolein ( 0.92 mg/mL in chloroform) and 2 μL of $^{14}$C labeled phosphotidylcholine (Amersham, cat. # CFA 695, L-3-phosphatidylcholine,1,2-di[1-$^{14}$C]oleoyl) are added and dried under nitrogen and reconstituted in 2 mL of assay buffer. The lipid suspension is sonicated using Branson 450 sonifier as described above. The donor and acceptor liposomes are centrifuged for 2 hours at 7° C. at 46,000 rpm in Ti50 rotor using Beckman Ultracentrifuge. The upper 75% of the supernatant is carefully removed and stored at 4° C. until used for MTP transfer assay.

MTP activity is measured using a MTP transfer assay. In this assay, donor and acceptor vesicles are mixed together with soluble MTP and test compound to measure the transfer of triglycerides from donor vesicles to acceptor vesicles. 50 μL of donor vesicles, 50 μL of acceptor vesicles, 20 μL of bovine serum albumin (10% w/v) and 50 μL of MTP (15 μg protein) are added along with various concentrations of test compound in a final volume 450 μL of assay buffer.

After incubation at 37° C. for 45 min, the triglyceride transfer Is terminated by addition of 300 μL of DEAE cellulose suspension (50%, w/v). After 4 min of vortexing, the donor vesicles bound to the DEAE cellulose are separated from acceptor vesicles by centrifuging at 14,000 rpm for 7 min. 250 μL of supernatant containing acceptor vesicles are counted using 5.5 mL of Ready safe scintillation solution (Beckman, cat. # 158735). The $^{14}$C and $^3$H counts are used to calculate the percent recovery of acceptor liposomes and the percent of triglyceride transfer using first order kinetics. Inhibition of triglyceride transfer by test compound is calculated by measuring the decrease in $^3$H label of triglyceride present in the acceptor vesicles as compared to controls where no test compound is present.

Illustrative of the invention the compound of example 13b demonstrates an IC$_{50}$ of about 1.8 nM in the Apo B assay and an IC$_{50}$ of about 60 nM in the MTP assay. The compound of example 13(i) demonstrates an IC$_{50}$ of about 0.7 nM in the Apo B assay and an IC$_{50}$ of about 70 nM in the MTP assay. The compound of example 13(al) demonstrates an IC$_{50}$ of about 3 nM in the Apo B assay. The compound of example 13(ey) demonstrates an IC$_{50}$ of about 1 nM in the Apo B assay.

The in vivo serum triglyceride lowering effect of the compounds of the invention can be determined by measuring their effect on triglyceride levels in mice, rats or dogs according to methodology well known in the art, e.g., in a model of pre-established hypertriglyceridemia in fructose fed rats or in normolipidemic rats.

The in vivo serum cholesterol lowering effect of the compounds of the invention can be determined by measuring their effect on cholesterol levels in mice, rats or dogs according to methodology well known in the art, e.g., in normolipidemic rats.

Illustrative of the invention, the compound of example 13(i) lowers both plasma triglycerides and cholesterol at a dose of 10 mg/kg. p.o.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg (=20–133 mbar). The structure of final products, intermediates and starting materials is confirmed by standard analytical methods, e.g., microanalysis and spectroscopic characteristics (e.g., MS, IR, NMR). Abbreviations used are those conventional in the art. The concentration for $[a]_D$ determinations is expressed in mg/ml. Compounds are purified by standard methods, e.g., recrystallization and high pressure liquid chromatography (HPLC).

The following Examples serve to illustrate the invention.

EXAMPLE 1

4'-Trifluoromethylbiphenyl-2-carboxylic acid (2-benzenesulfonylamino-indan-5-yl)-amide

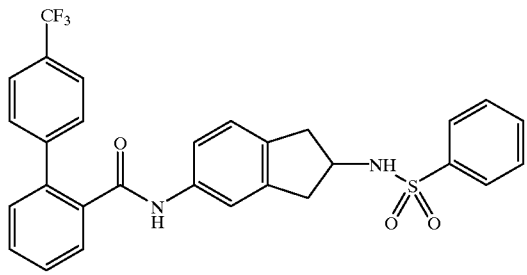

A. 2-Amino-5-nitro-indane hydrochloride

To N-(5-nitro-indan-2-yl)-acetamide (23.5 g, 107 mmol) is added 2N hydrochloric acid (500 mL). The mixture is heated to reflux for 24 h and then concentrated in vacuo. Methanol (100 mL) is added to the residue and the mixture is concentrated in vacuo. Toluene (100 mL) is added and the mixture is again concentrated. A solution of the residue in methanol (100 mL) is warmed, diethyl ether (500 mL) is added and the mixture is let stand overnight. The solid is collected by filtration and air dried to yield a white solid.

B. (5-Nitro-indan-2-yl)-carbamic acid tert-butyl ester

To a solution of the title A compound (20.4 g, 95 mmol) in methylene chloride (500 mL) under nitrogen is added diisopropylethyl amine (14.7 g, 114 mmol). To this is added a solution of di-tert-butyldicarbonate (22.8 g, 105 mmol) in methylene chloride. The mixture is stirred for 16 h, washed with brine, 1N hydrochloric acid, brine, and then dried over sodium sulfate. The solution is concentrated in vacuo to give a solid residue which is triturated with diethyl ether to give a white solid.

C. (5-Amino-indan-2-yl)-carbamic acid tert-butyl ester

A solution of the title B compound (3.52 g, 12.6 mmol) in ethanol (100 mL) is degassed and 10% palladium on carbon added. The reaction is evacuated and placed under 1 atm $H_2(g)$ for 2 h. Filtration of the reaction mixture through Celite is followed by concentration of the filtrate under reduced pressure to give (5-amino-indan-2-yl)-carbamic acid tert-butyl ester as an oil which is used directly without further purification.

D. 4'-Trifluoromethyl-2-biphenylcarboxylic acid chloride

To a solution of 4'-trifluoromethyl-2-biphenylcarboxylic acid (5.15 g, 19.35 mmol) in methylene chloride (100 mL) is added oxalyl chloride (5.06 mL, 58.04 mmol) followed by 2 drops of DMF. Addition of DMF results in vigorous gas evolution. After 1.5 h, the reaction mixture is concentrated under reduced pressure to give an oil which is used as is without purification.

E. {5-[(4'-Trifluoromethylbiphenyl-2-carbonyl)-amino]-indan-2-yl}-carbamic acid tert-butyl ester To a solution of the title C compound ((5-amino-indan-2-yl)-carbamic acid tert-butyl ester; 12.5 mmol) in methylene chloride (75 mL) is added diisopropylethyl amine (3.3 g, 25 mmol) followed by a 0.5 M solution of the title D compound (4'-trifluoromethyl-2-biphenyl carboxylic acid chloride, 12.6 mmol) in methylene chloride (25.3 mL). After stirring 16 h, the reaction mixture is poured into ethyl acetate and washed with 1N HCl, 8% $NaHCO_3$ solution, and brine. The organic layer is dried ($MgSO_4$) and concentrated under reduced pressure to give a solid. Recrystallization from toluene gives {5-[(4'-trifluoromethylbiphenyl-2-carbonyl)amino]-indan-2-yl}-carbamic acid tert-butyl ester in two crops; mp 198–201° C. MS (ES+), m/z 514 (M+NH+$_4$).

F. 4'-Trifluoromethylbiphenyl-2-carboxylic acid (2-amino-indan-5-yl)-amide hydrochloride A solution of the title E compound ({5-[(4'-trifluoromethylbiphenyl-2-carbonyl)-amino]indan-2-yl}-carbamic acid tert-butyl ester, 5.19 g, 10.5 mmol) in formic acid (40 mL) is heated to 40° C. with stirring. After 3 h, the reaction mixture is cooled to room temperature and stirring is continued for 16 h. The reaction mixture is concentrated under reduced pressure and the resulting oil dissolved in ethyl acetate. The organic layer is washed with 8% $NaHCO_3$ solution until the aqueous layer remains basic at which point a precipitate forms in the organic layer. The precipitate is collected by filtration to give 4'-trifluoromethylbiphenyl-2-carboxylic acid (2-amino-indan-5-yl)-amide. The organic layer of the filtrate is dried ($MgSO_4$) and concentrated under reduced pressure to give a solid. Trituation of the solid with diethyl ether yields additional 4'-trifluoromethylbiphenyl-2-carboxylic acid (2-amino-indan-5-yl)-amide.

A small portion of free amine (0.580 mmol) is dissolved in ethyl acetate and saturated with HCl (g) to give the HCl salt as a white solid. $^1H$ NMR (MeOH-$d_4$: 250 MHz): δ 7.70–7.48 (7H, m), 7.16 (4H, q), 4.06 (1H, m), 3.38 (2H, dd), 2.97 (2H, d). MS (ES+), m/z 397 (M+H).

G. 4'-Trifluoromethylbiphenyl-2-carboxylic acid (2-benzenesulfonylamino-indan-5-yl)-amide To a solution of the title F compound (4'-trifluoromethylbiphenyl-2-carboxylic acid (2-amino-indan-5-yl)-amide, 0.100 g, 0.250 mmol) in methylene chloride (10 mL) is added diisopropylethyl amine (0.036 g, 0.280 mmol) followed by benzenesulfonyl chloride (0.046 g, 0.260 mmol). After 1 h, the reaction mixture is poured into ethyl acetate and washed with 1 N HCl, 8% $NaHCO_3$ solution, water, and brine. The organic layer is dried ($MgSO_4$) and concentrated under reduced pressure to give an oil which is purified by silica gel chromatography. Drying under vacuum at 60° C. gives 4'-trifluoromethyl-biphenyl-2-carboxylic acid (2-benzenesulfonylamino-indan-5-yl)-amide as a non-crystalline solid; mp 96° C. sinters. MS (ES+), m/z 537 (M+1), 554 (M+$NH_4^+$).

EXAMPLE 2

The following compounds are prepared similarly to Example 1 using the title F compound of Example 1 (4'-trifluoromethylbiphenyl-2-carboxylic acid (2-amino-indan-5-yl)-amide and the appropriate N-derivatizing agent (e.g., a sulfonyl chloride, an acid chloride, an isocyanate, a sulfamoyl chloride).

| Compound | Structure | MS[m/z] | MP (° C.) |
|---|---|---|---|
| (a) | 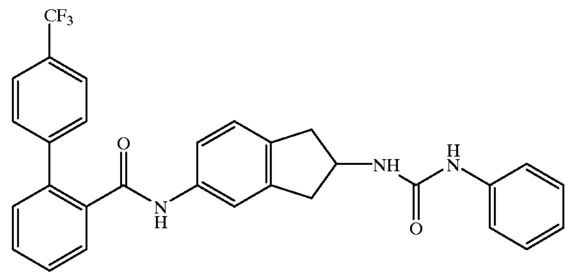 | | 149–155 |
| (b) | 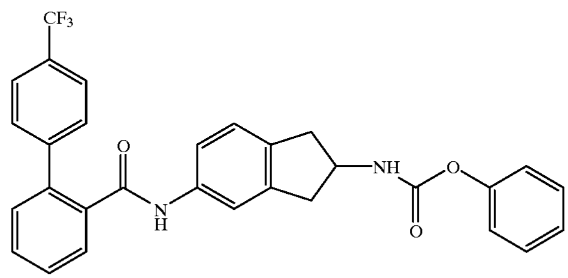 | 534 [M + NH$_4^+$] | 178–181 |
| (c) | 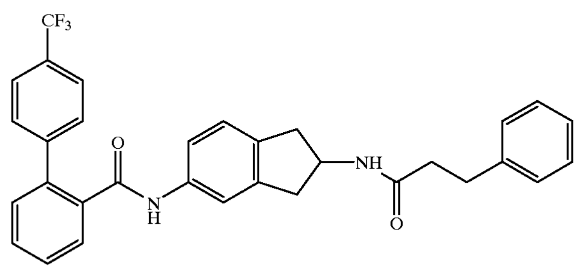 | 546 [M + NH$_4^+$] | 180–182 |
| (d) | 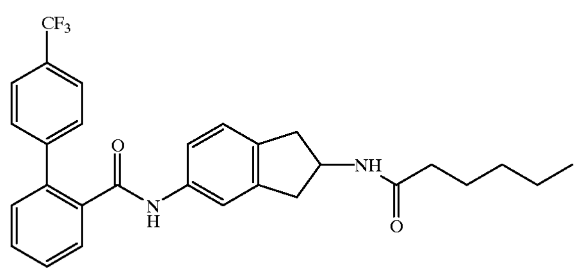 | 512 [M + NH$_4^+$] | 190–193 |
| (e) | 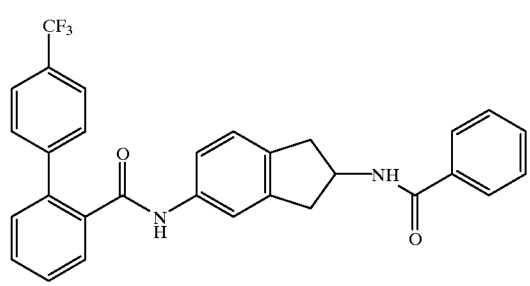 | 518 [M + NH$_4^+$] | 253–255 |

-continued

| Compound | Structure | MS[m/z] | MP (° C.) |
|---|---|---|---|
| (f) | 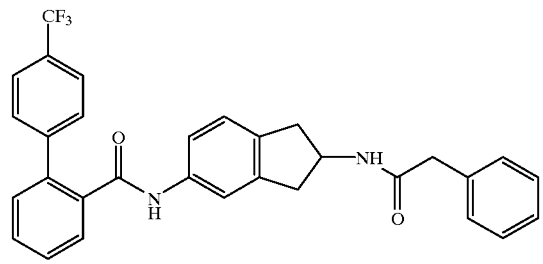 | 515[M + 1] | 209–213 |
| (g) | 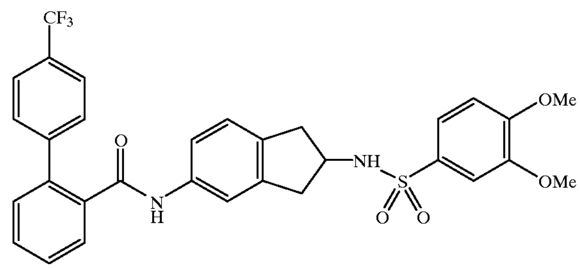 | 614 [M + NH$_4^+$] | 98–112 |
| (h) | 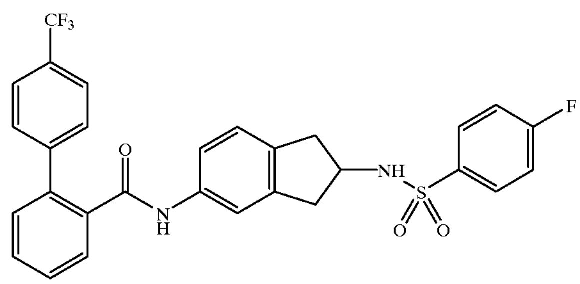 | 572 [M + NH$_4^+$] | 97–105 |
| (i) | 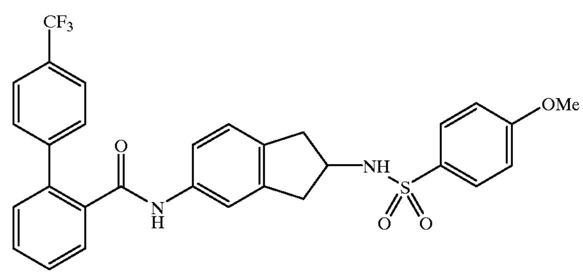 | 584 [M + NH$_4^+$] | 97–108 |
| (j) | 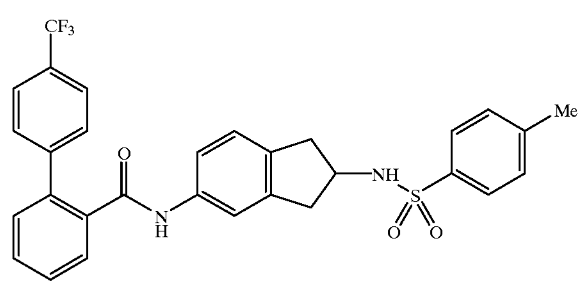 | 568 [M + NH$_4^+$] | 98–112 |

-continued

| Compound | Structure | MS[m/z] | MP (° C.) |
|---|---|---|---|
| (k) | 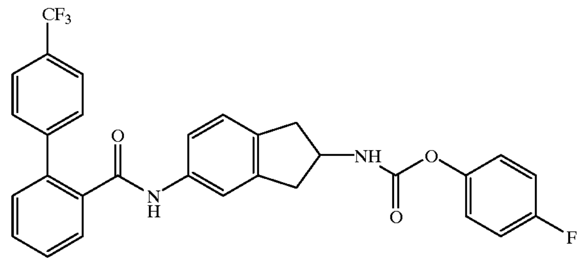 | 552 [M + NH$_4^+$] | 202–206 |
| (l) | 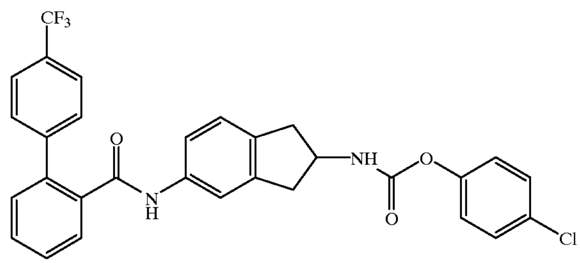 | 568 [M + NH$_4^+$] 570 [M + NH$_4^+$] | 205–211 |
| (m) | 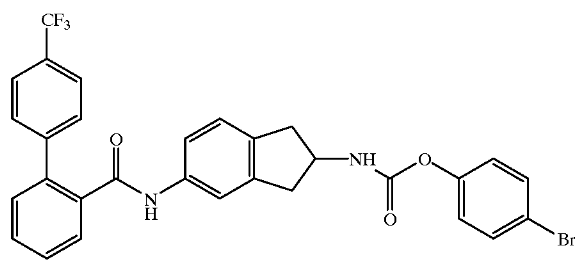 | 612 [M + NH$_4^+$] 614 [M + NH$_4^+$] | 203–208 |
| (n) | 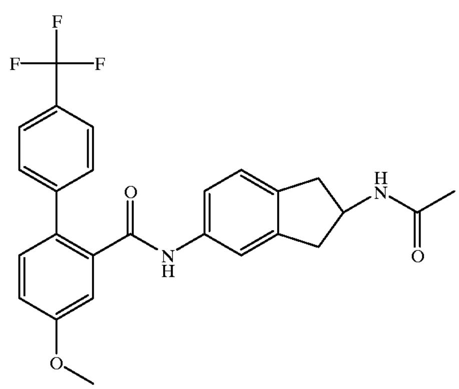 | 469[M + 1] | 102–104 |

| Compound | Structure | MS[m/z] | MP (° C.) |
|---|---|---|---|
| (o) | 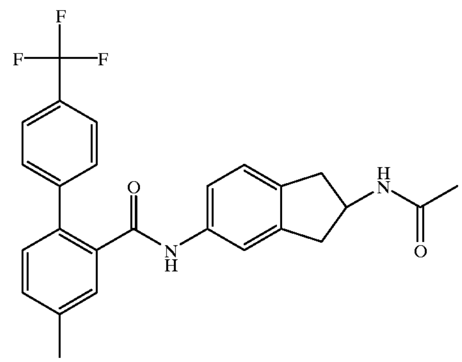 | 453[M + 1] | 91–93 |
| (p) | 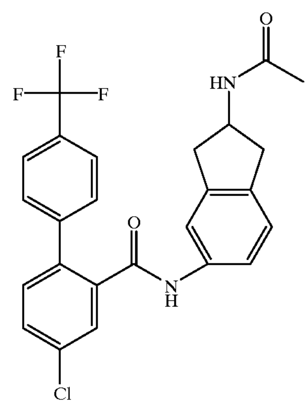 | 473[M + 1] | 119–121 |
| (q) | 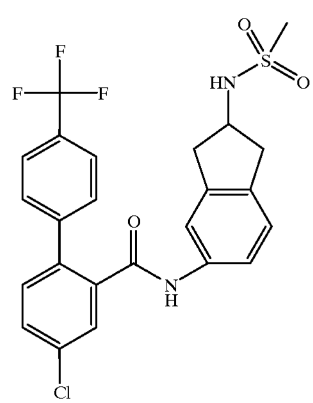 | 509[M + 1] | 190–191 |
| (r) | 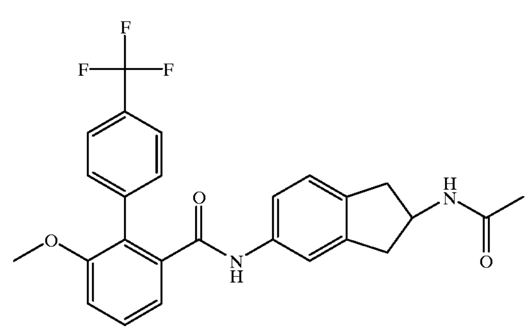 | 469[M + 1] | 185–186 |

-continued

| Compound | Structure | MS[m/z] | MP (° C.) |
|---|---|---|---|
| (s) | 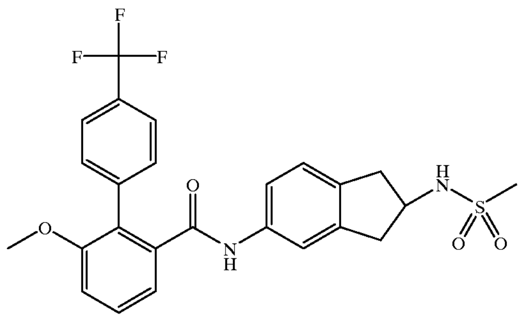 | 505[M + 1] | 96–98 |
| (t) | 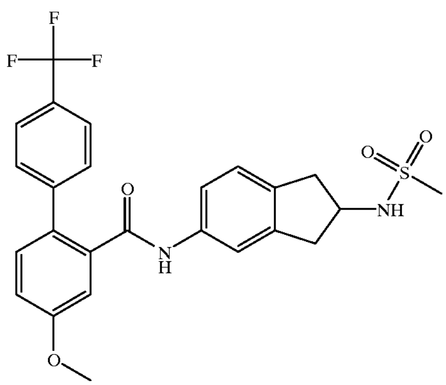 | 504[M + 1] | foam |
| (u) | 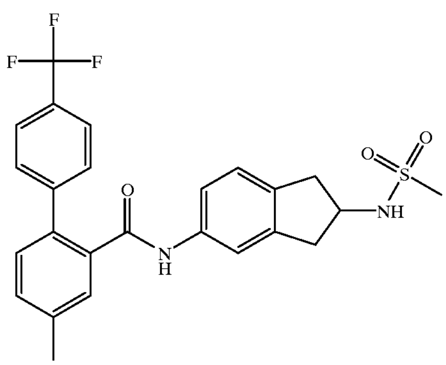 | 489[M + 1] | 71–75 |
| (v) | 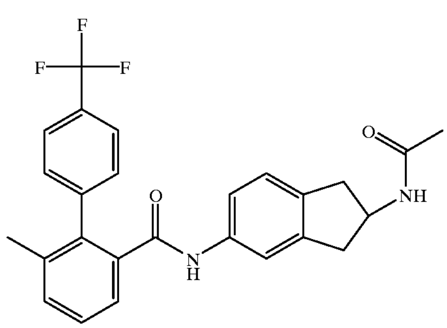 | 453[M + 1] | 114–117 |

-continued
| Compound | Structure | MS[m/z] | MP (° C.) |
|---|---|---|---|
| (w) | 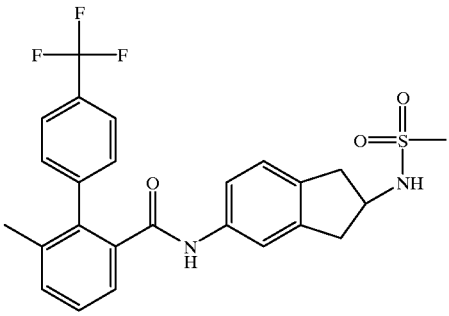 | 489[M + 1] | 94–99 |
| (x) | 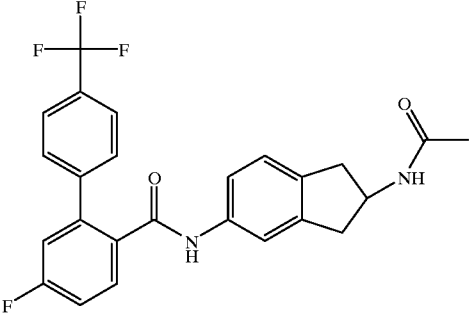 | 457[M + 1] | 110–116 |
| (y) | 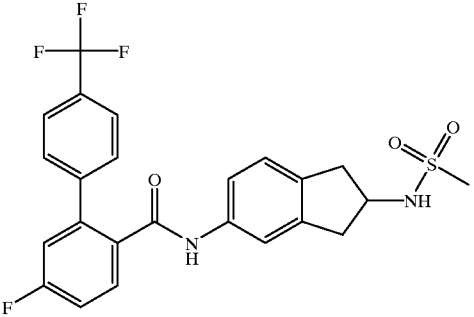 | 493[M + 1] | 186–187 |
| (z) | 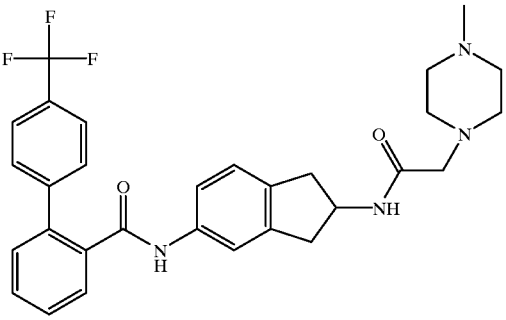 | 537[M + 1] | foam |

-continued

| Compound | Structure | MS[m/z] | MP (° C.) |
|---|---|---|---|
| (aa) | 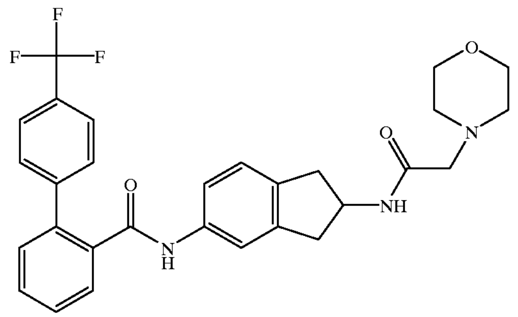 | 524[M + 1] | foam |
| (ab) | 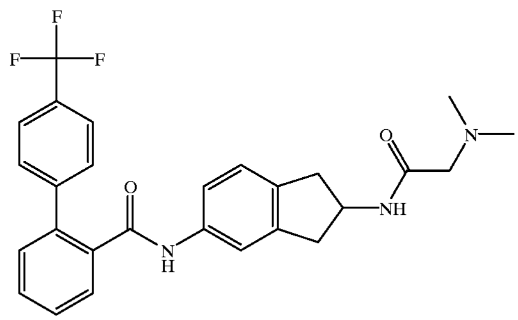 | 482[M + 1] | foam |
| (ac) | 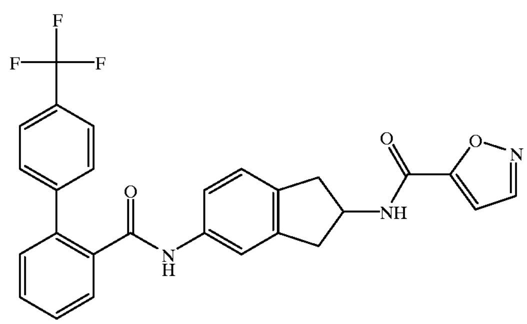 | 492[M + 1] | 227–228 |
| (ad) | 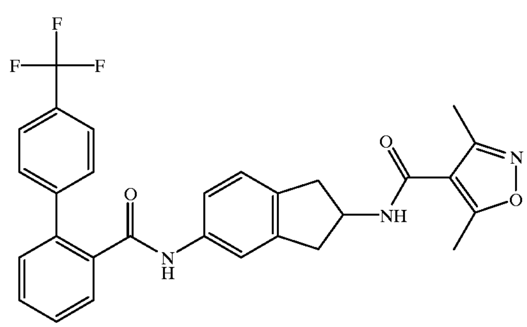 | 520[M + 1] | 216–218 |

-continued

| Compound | Structure | MS[m/z] | MP (° C.) |
| --- | --- | --- | --- |
| (ae) | 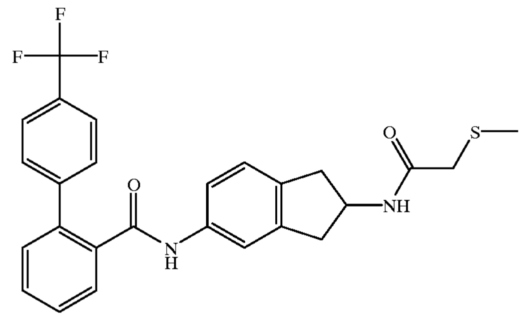 | 485[M + 1] | 184–186 |
| (af) | 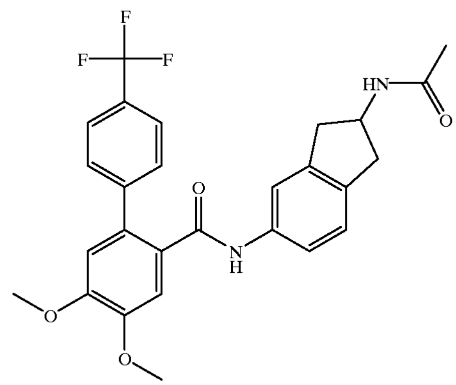 | 499[M + 1] | 122–124 |
| (ag) | 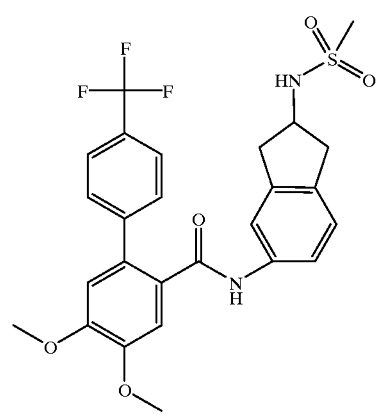 | 535[M + 1] | 106–108 |
| (ah) | 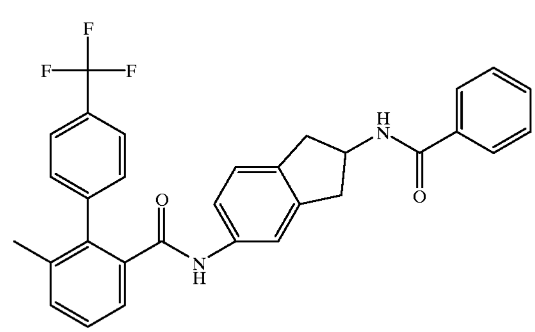 | 515[M + 1] | 245–249 |

-continued
| Compound | Structure | MS[m/z] | MP (° C.) |
|---|---|---|---|
| (ai) | 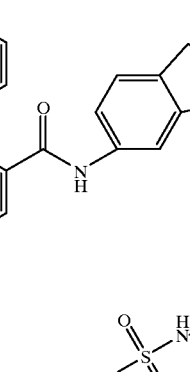 | 551[M + 1] | foam |
| (aj) | 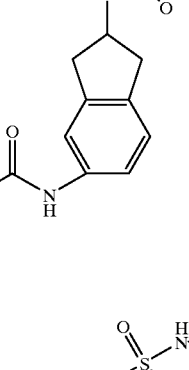 | 558[M + 1] | 158–159 |
| (ak) | 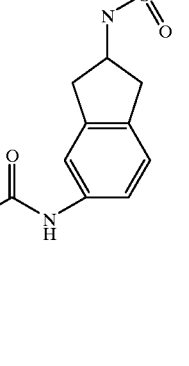 | 518[M + 1] | 182–183 |
| (al) | 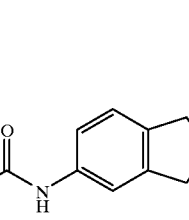 | 531[M + 1] | 161–164 |

-continued
| Compound | Structure | MS[m/z] | MP (° C.) |
|---|---|---|---|
| (am) | 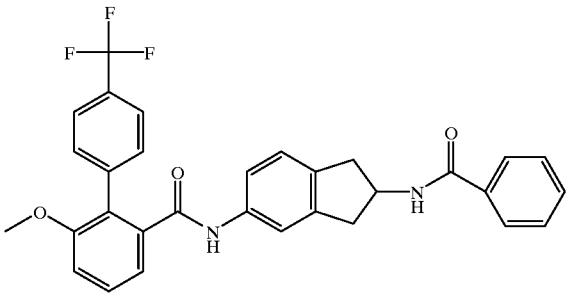 | 531[M + 1] | 239–240 |
| (an) | 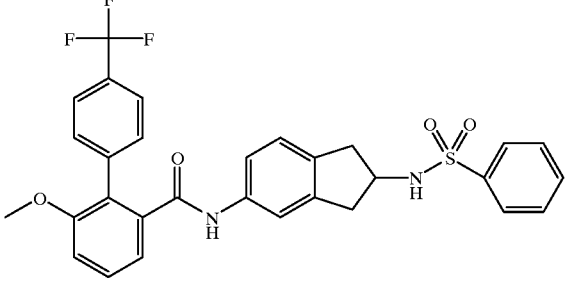 | 567[M + 1] | foam |
| (ao) | 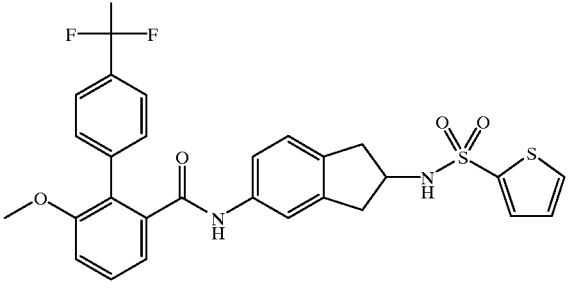 | 573[M + 1] | 167–170 |
| (ap) | 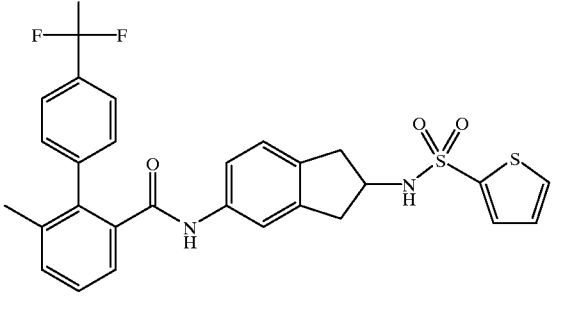 | 557[M + 1] | foam |

-continued
| Compound | Structure | MS[m/z] | MP (° C.) |
|---|---|---|---|
| (aq) | 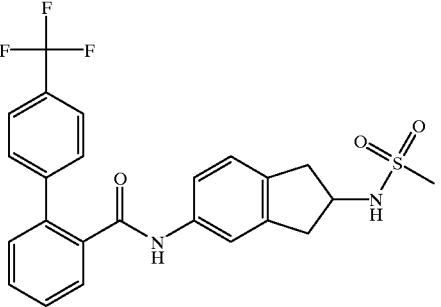 | 492[M + 1] | 195–197 |
| (ar) | 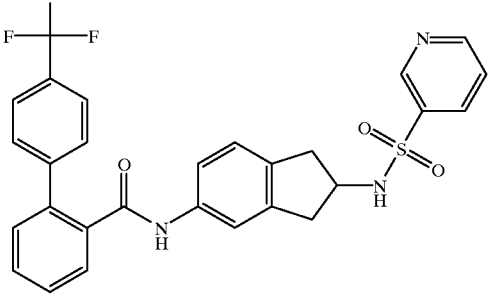 | 538[M + 1] | foam |
| (as) | 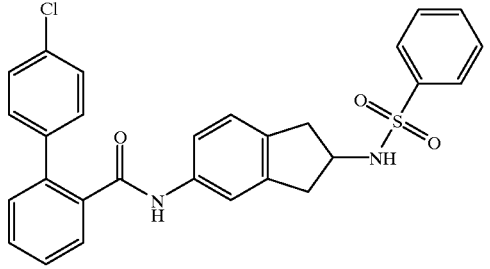 | 520 [M + NH$_4^+$] | foam |
| (at) | 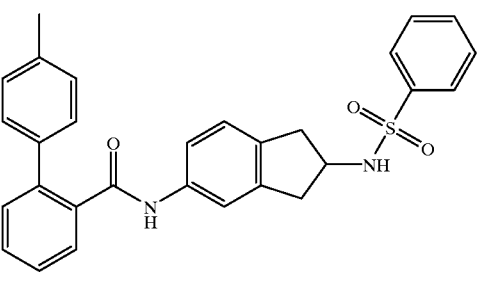 | 483[M + 1] | 92–105 |
| (au) | 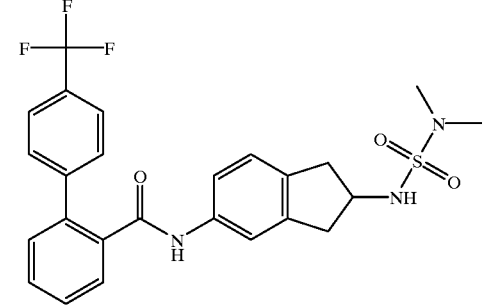 | 504[M + 1] | 193–196 |

-continued

| Compound | Structure | MS[m/z] | MP (° C.) |
|---|---|---|---|
| (av) | 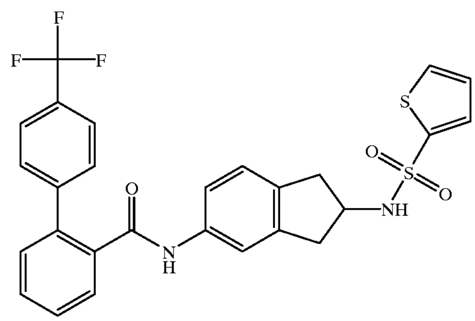 | 543[M + 1] | foam |
| (aw) | 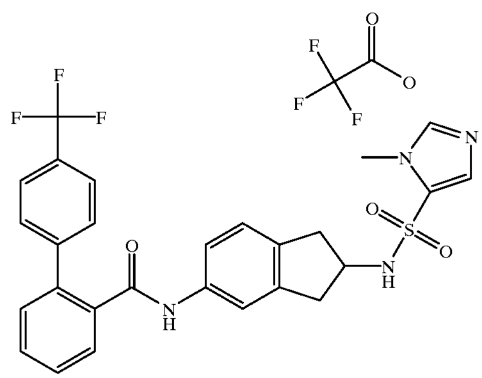 | 541[M + 1] | |
| (ax) | 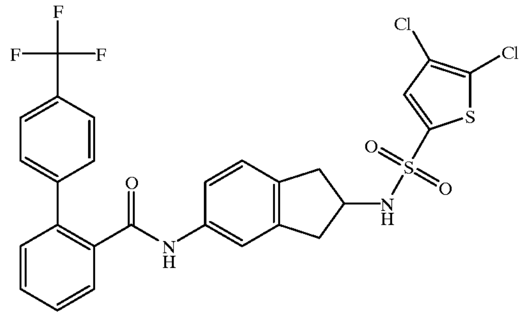 | 611[M + 1] | |
| (ay) | 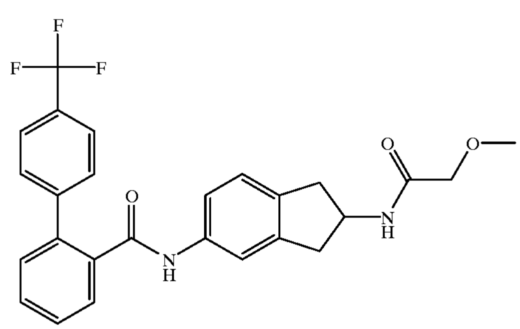 | 469[M + 1] | foam |

-continued

| Compound | Structure | MS[m/z] | MP (° C.) |
|---|---|---|---|
| (az) | 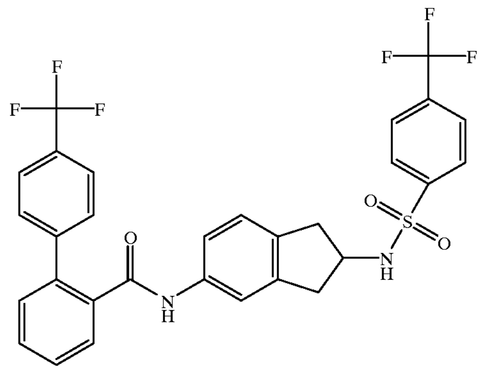 | 605[M + 1] | |
| (ba) | 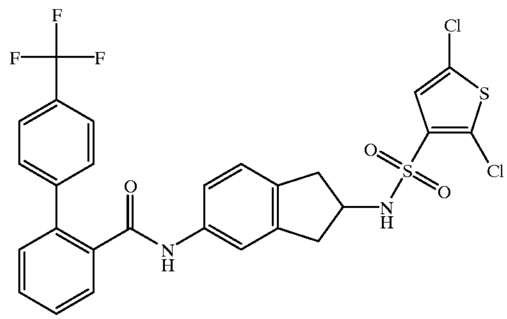 | 611[M + 1] | |
| (bb) | 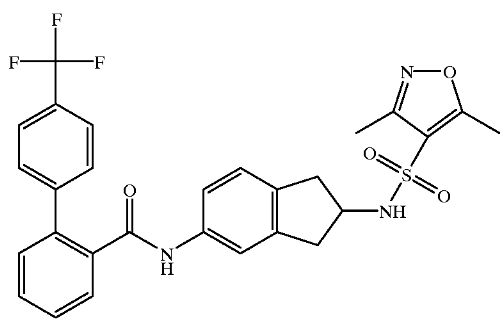 | 556[M + 1] | |
| (bc) | 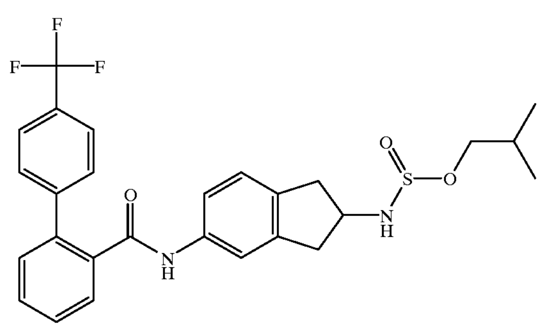 | 497[M + 1] | |

| Compound | Structure | MS[m/z] | MP (° C.) |
|---|---|---|---|
| (bd) | 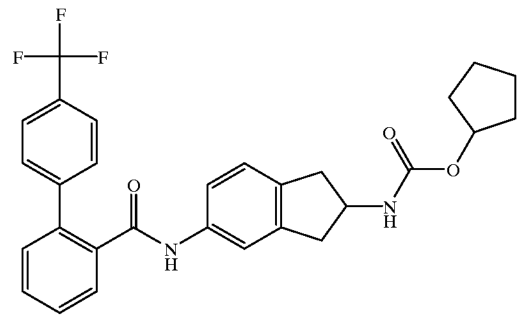 | 509[M + 1] | |
| (be) | 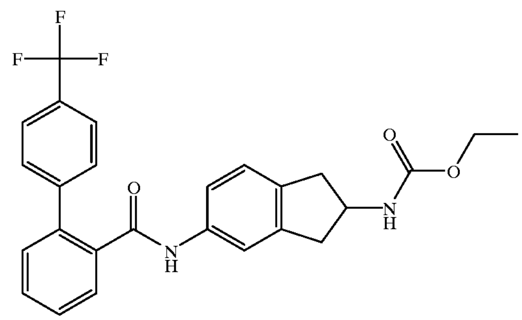 | 469[M + 1] | |
| (bf) | 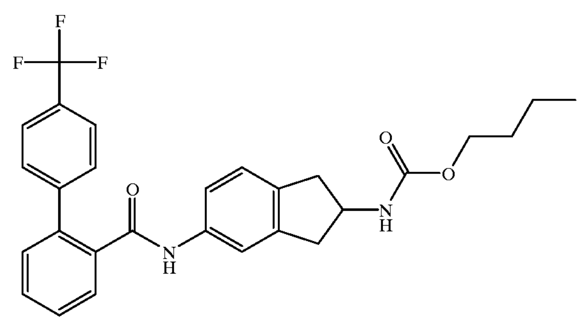 | 497[M + 1] | |
| (bg) | 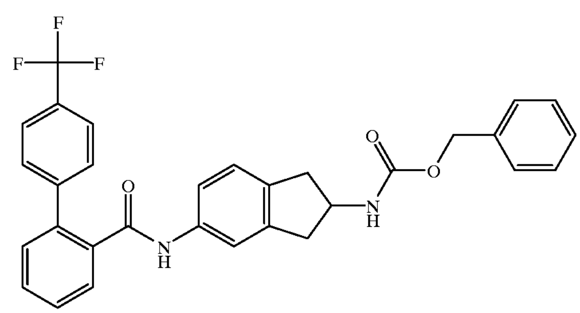 | 531[M + 1] | |

-continued

| Compound | Structure | MS[m/z] | MP (° C.) |
|---|---|---|---|
| (bh) | 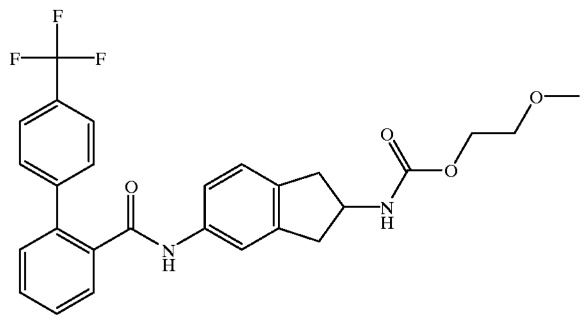 | 499[M + 1] | |
| (bi) | 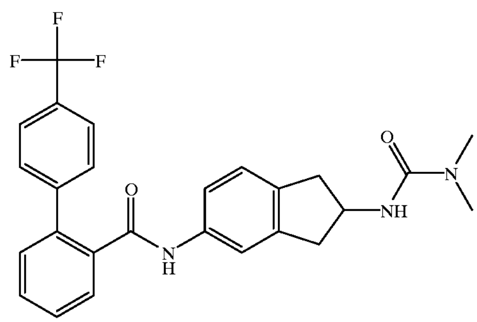 | 468[M + 1] | |
| (bj) | 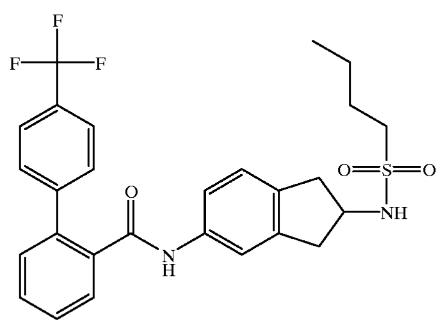 | 517[M + 1] | |
| (bk) | 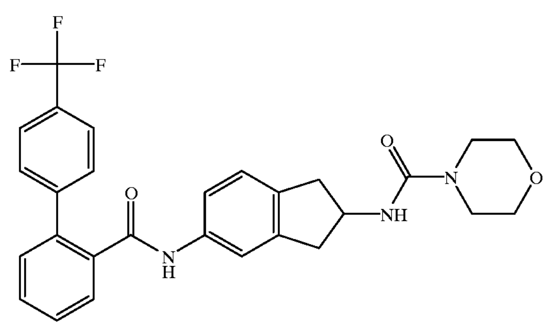 | 510[M + 1] | |

-continued
| Compound | Structure | MS[m/z] | MP (° C.) |
|---|---|---|---|
| (bl) | 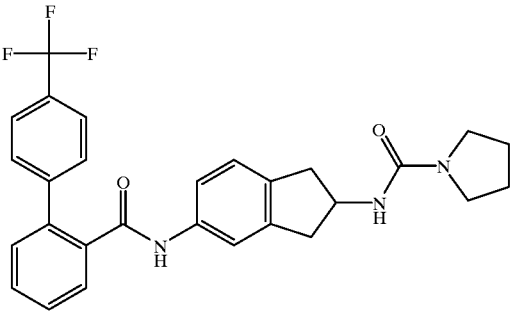 | 494[M + 1] | |
| (bm) | 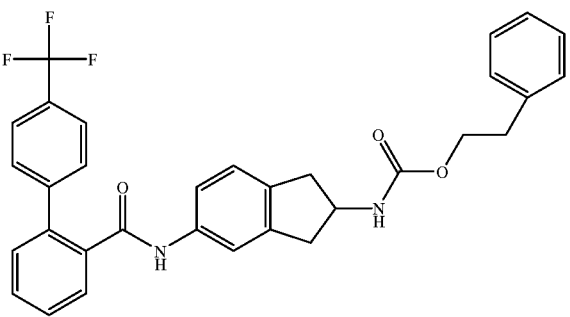 | 545[M + 1] | |
| (bn) | 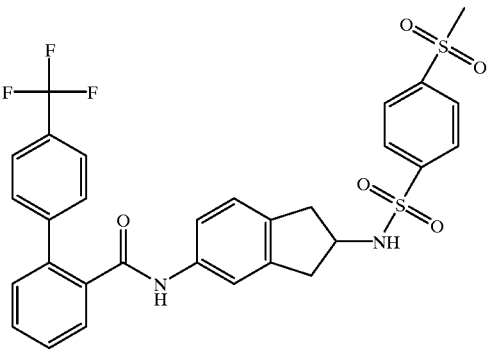 | 615[M + 1] | |
| (bo) | 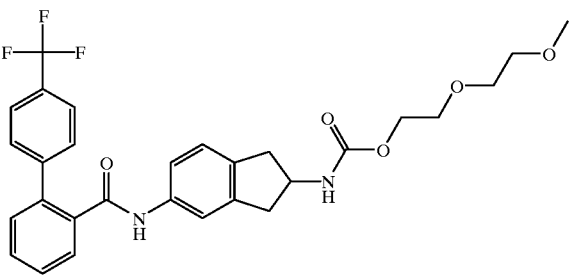 | 543[M + 1] | |

-continued

| Compound | Structure | MS[m/z] | MP (° C.) |
|---|---|---|---|
| (bp) | 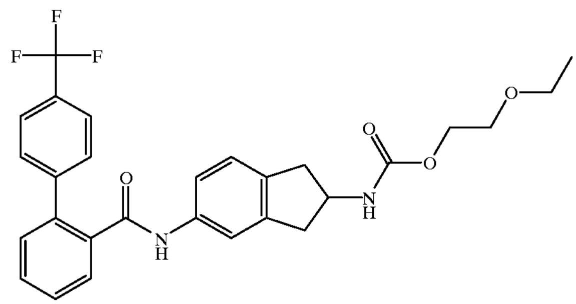 | 513[M + 1] | |
| (bq) | 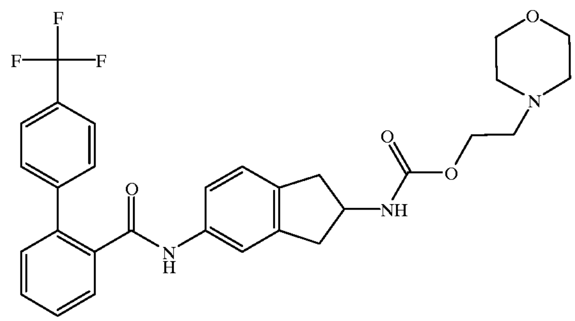 | 554[M + 1] | |
| (br) | 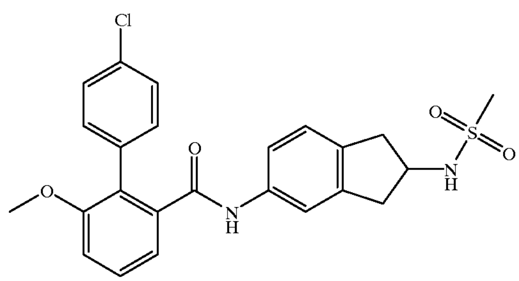 | 471[M + 1] | 99–102 |
| (bs) | 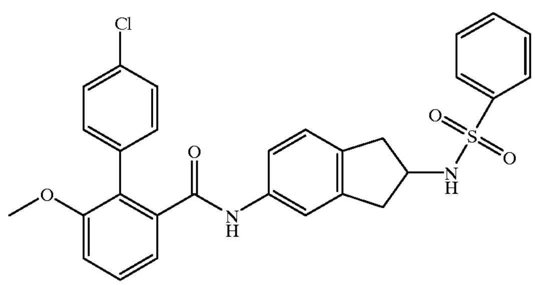 | 534[M + 1] | 95–97 |
| (bt) | 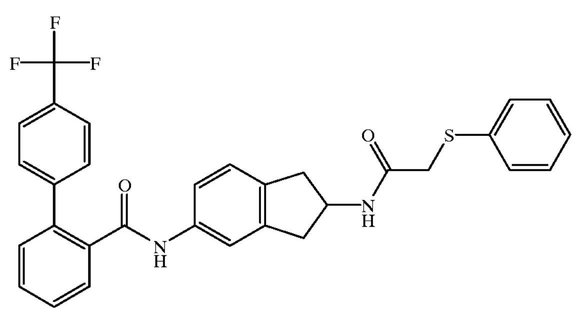 | 547[M + 1] | 218–219 |

-continued
| Compound | Structure | MS[m/z] | MP (° C.) |
|---|---|---|---|
| (bu) | 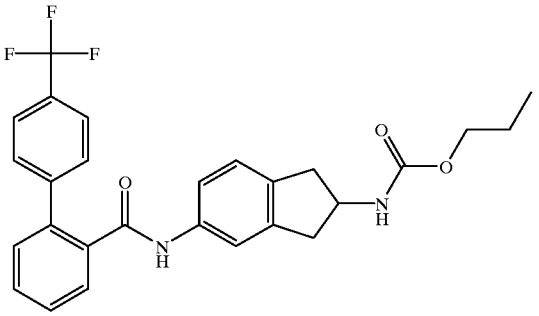 | 483[M + 1] | |
| (bv) | 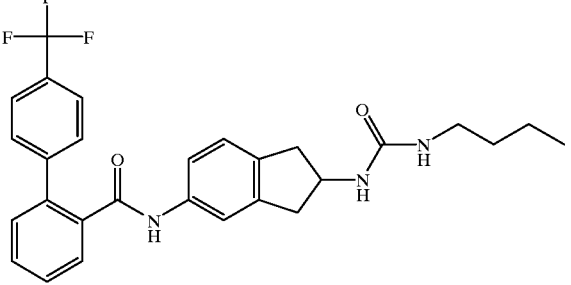 | 499[M + 1] | |
| (bw) | 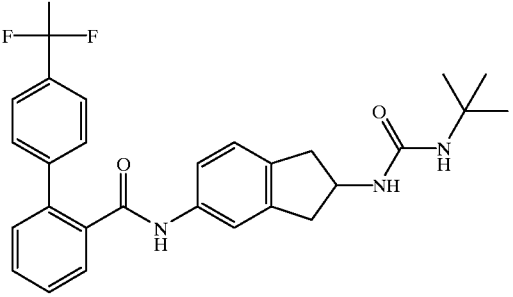 | 496[M + 1] | |
| (bx) | 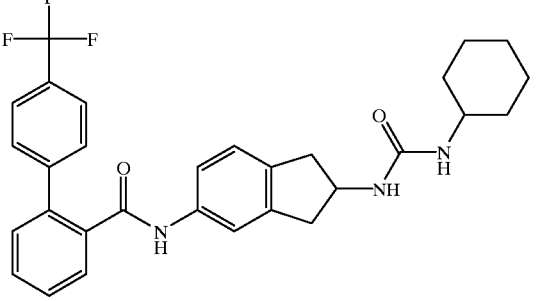 | 496[M + 1] | |

-continued
| Compound | Structure | MS[m/z] | MP (° C.) |
|---|---|---|---|
| (by) | 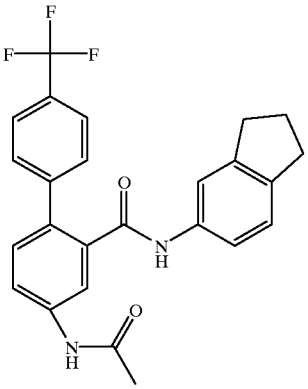 | 439[M + 1] | |
| (bz) | 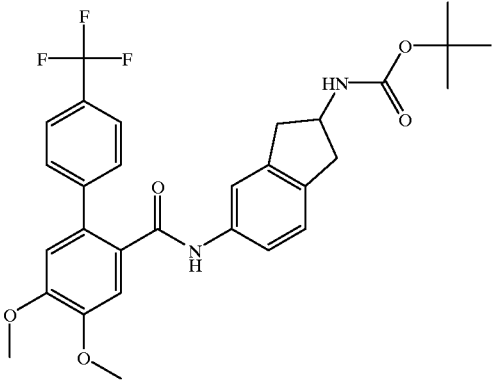 | 557[M + 1] | 207–208 |
| (ca) | 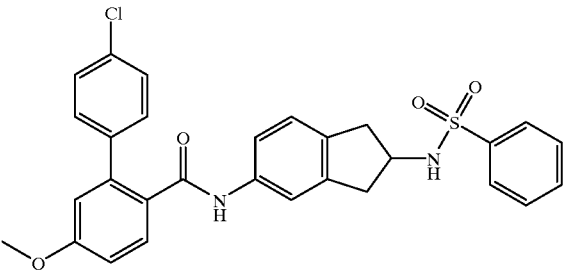 | 533[M + 1] | 95–125 |
| (cb) | 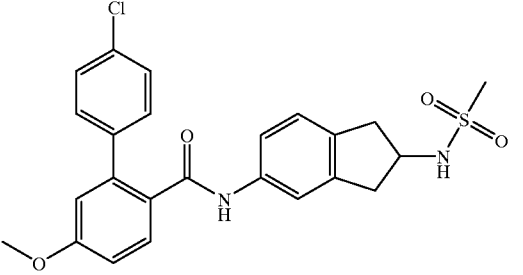 | 471[M + 1] | 132–134 |

-continued

| Compound | Structure | MS[m/z] | MP (° C.) |
|---|---|---|---|
| (cc) | 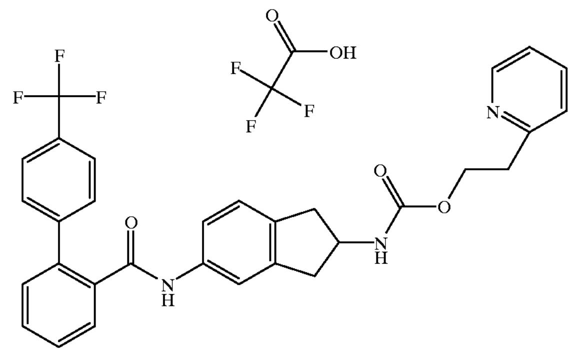 | 546[M + 1] | |
| (cd) | 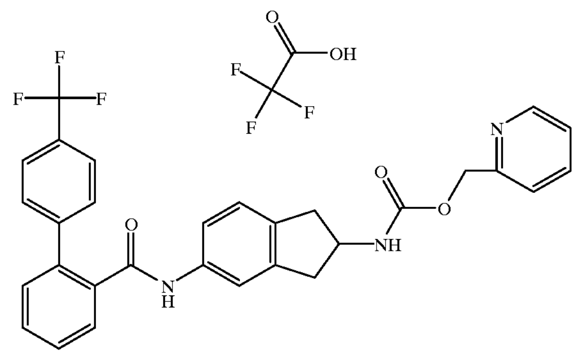 | 532[M + 1] | |
| (ce) | 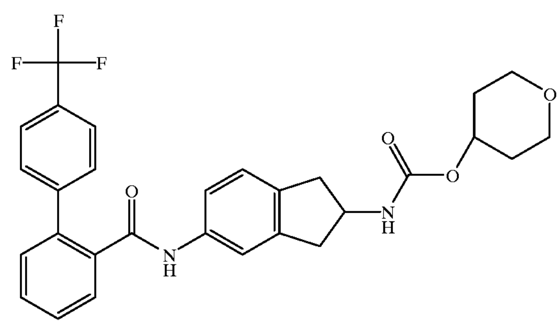 | 525[M + 1] | |
| (cf) | 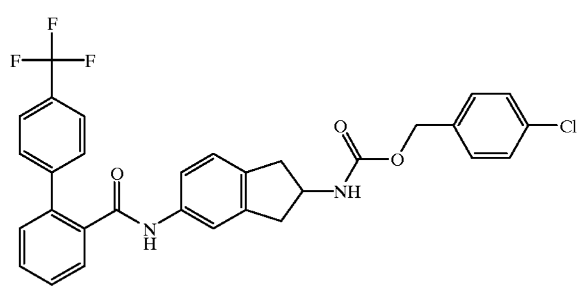 | 565[M + 1] | |

-continued

| Compound | Structure | MS[m/z] | MP (° C.) |
|---|---|---|---|
| (cg) | 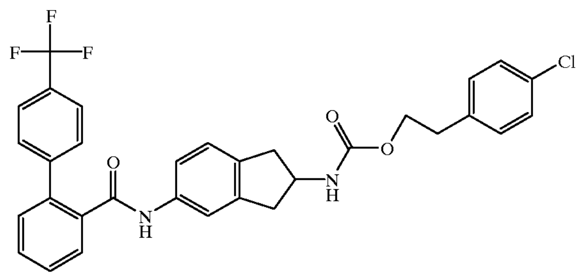 | 579[M + 1] | |
| (ch) | 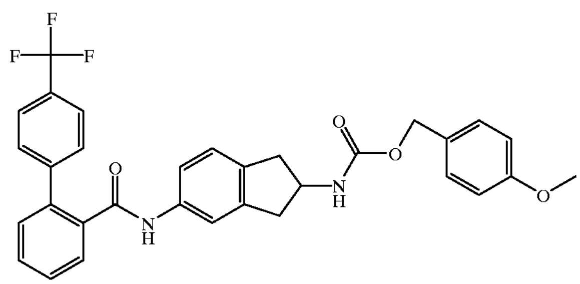 | 561[M + 1] | |
| (ci) | 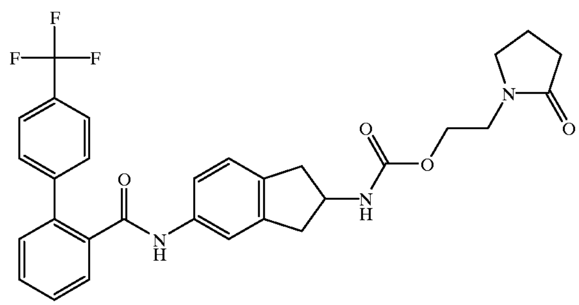 | 552[M + 1] | |
| (cj) | 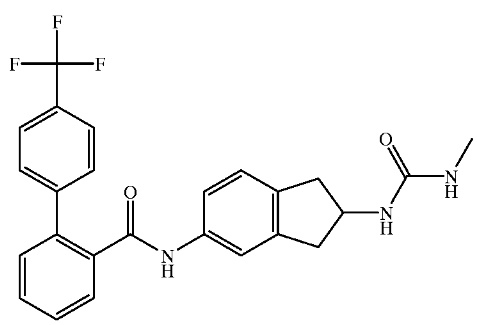 | 454[M + 1] | |
| (ck) | 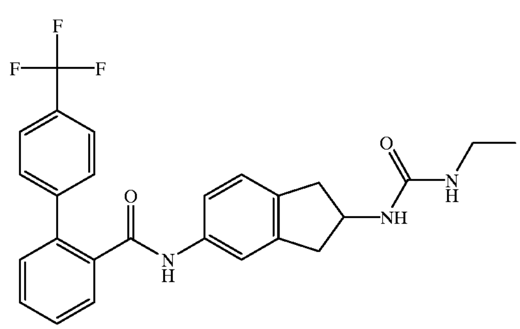 | 468[M + 1] | |

-continued
| Compound | Structure | MS[m/z] | MP (° C.) |
|---|---|---|---|
| (cl) | 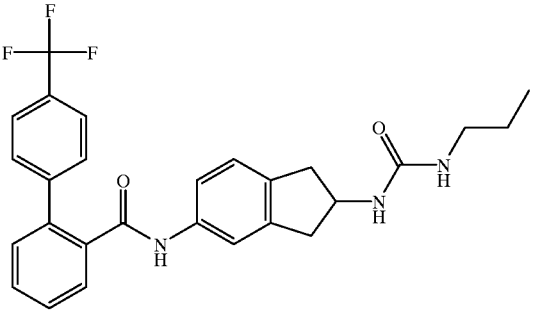 | 482[M + 1] | |
| (cm) | 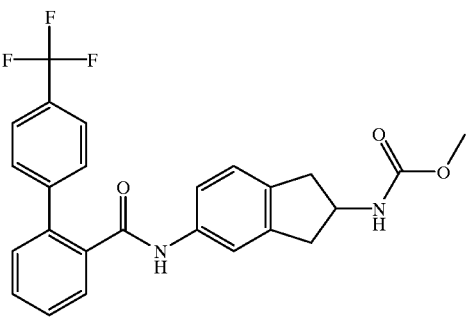 | 455[M + 1] | |
| (cn) | 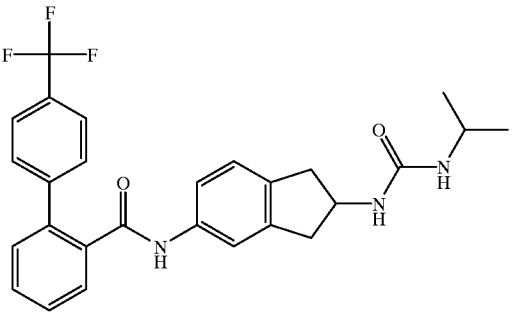 | 482[M + 1] | |
| (co) | 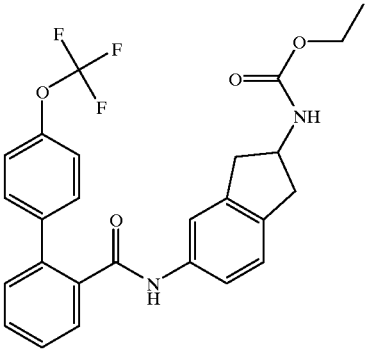 | 502 [M + NH₄⁺] | 144–145 |

-continued

| Compound | Structure | MS[m/z] | MP (° C.) |
|---|---|---|---|
| (cp) | 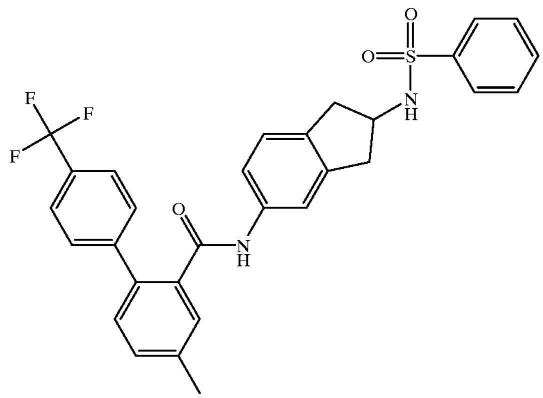 | 551[M + 1] | 83–101 |
| (cq) | 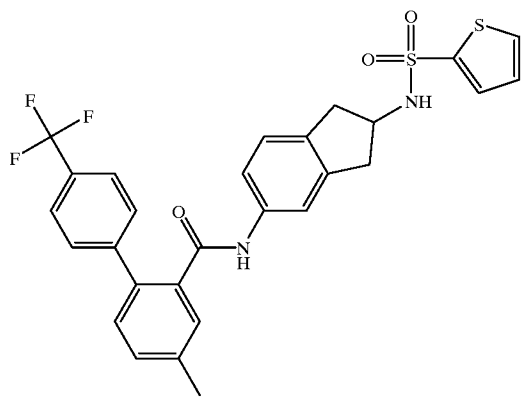 | 557[M + 1] | 83–99 |
| (cr) | 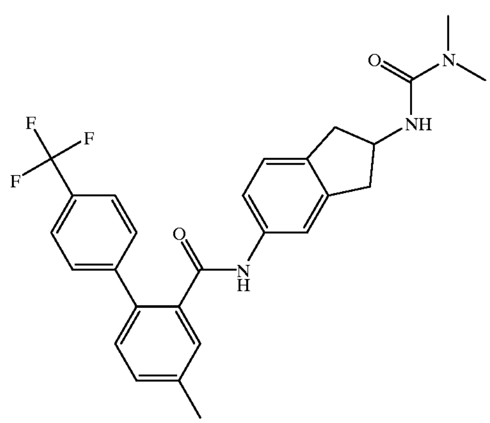 | 482[M + 1] | 102–110 |

-continued

| Compound | Structure | MS[m/z] | MP (° C.) |
|---|---|---|---|
| (cs) | 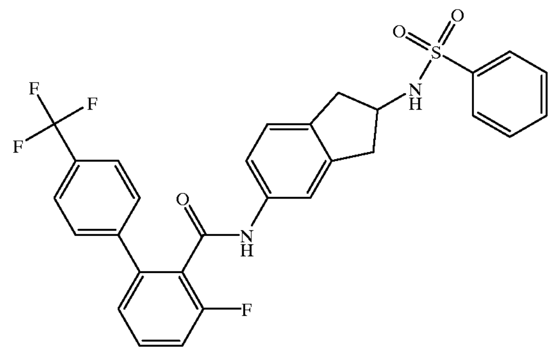 | 555[M + 1] | 196–200 |
| (ct) | 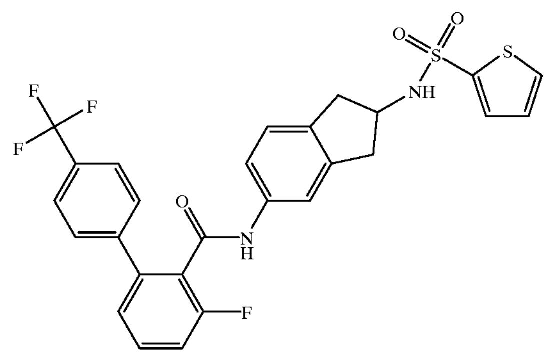 | 561[M + 1] | 75–89 |
| (cu) | 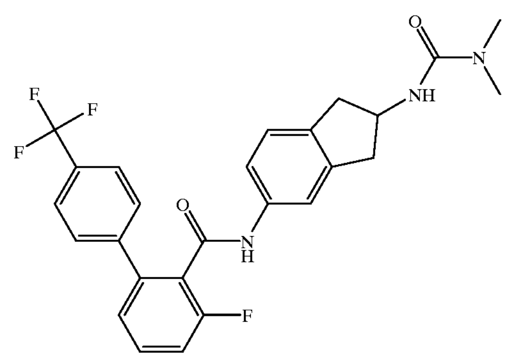 | 486[M + 1] | >230 |
| (cv) | 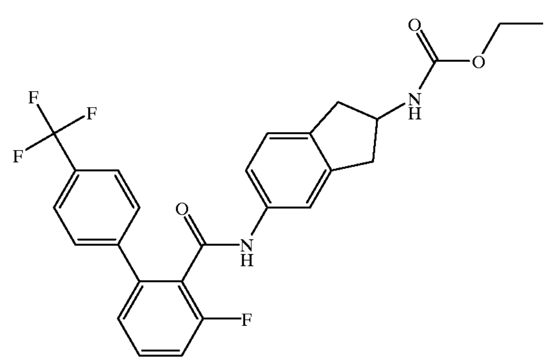 | 487[M + 1] | 90–100 |

-continued
| Compound | Structure | MS[m/z] | MP (° C.) |
|---|---|---|---|
| (cw) | 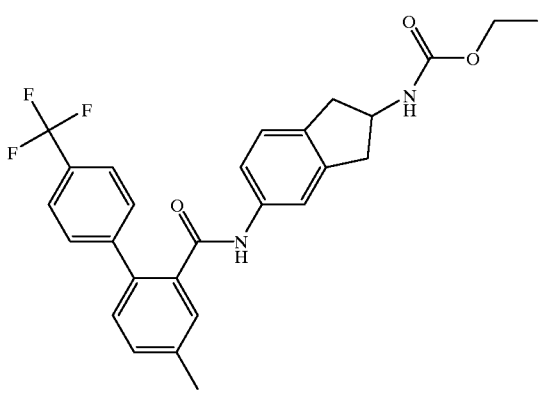 | 483[M + 1] | 80–88 |
| (cx) | 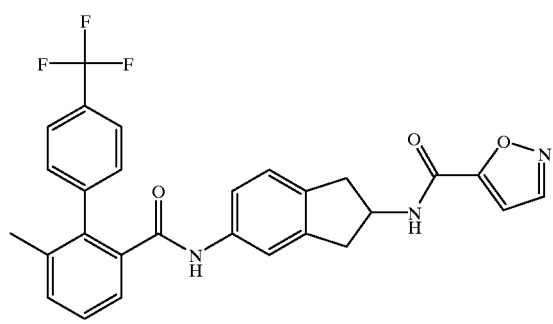 | 506[M + 1] | 105–115 |
| (cy) | 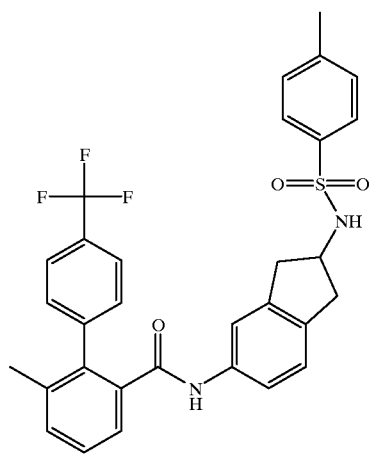 | 565[M + 1] | 104–108 |
| (cz) | 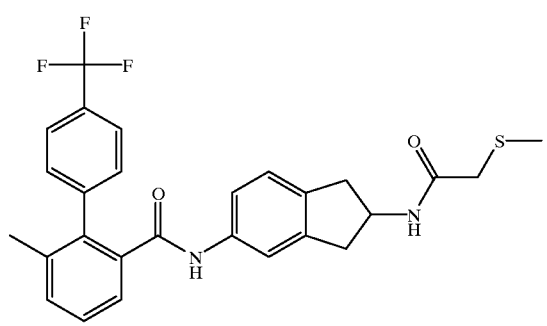 | 499[M + 1] | 189–191 |

-continued

| Compound | Structure | MS[m/z] | MP (° C.) |
|---|---|---|---|
| (da) | 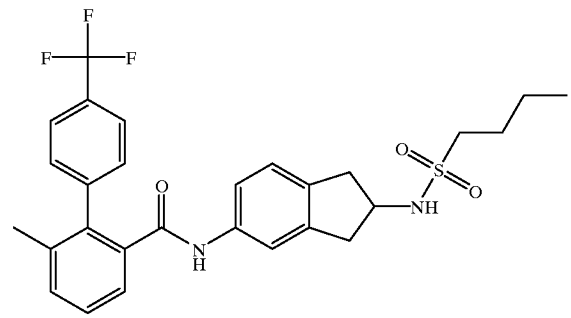 | 531[M + 1] | 209–211 |
| (db) | 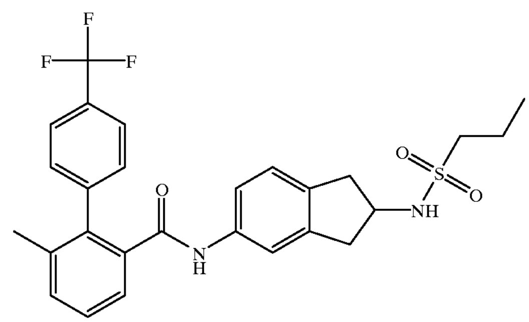 | 517[M + 1] | 2208–213 |
| (dc) | 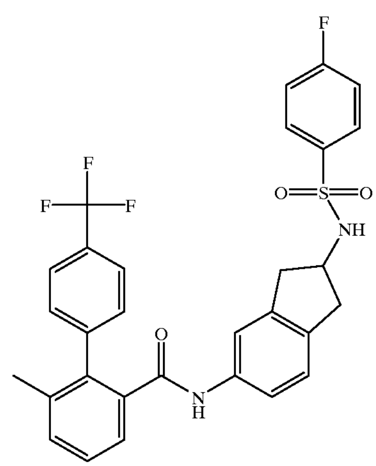 | 569[M + 1] | foam |
| (dd) | 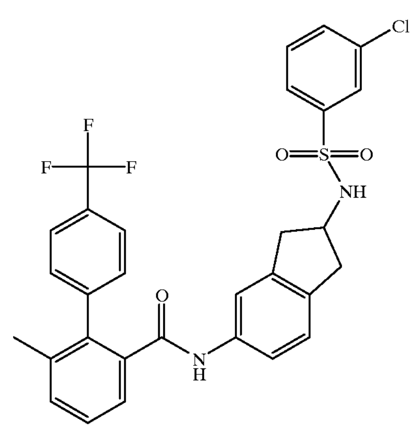 | 585[M + 1] | 101–104 |

| Compound | Structure | MS[m/z] | MP (° C.) |
|---|---|---|---|
| (de) | 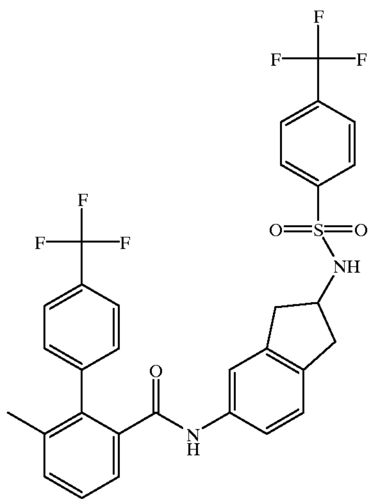 | 619[M + 1] | 95–99 |
| (df) | 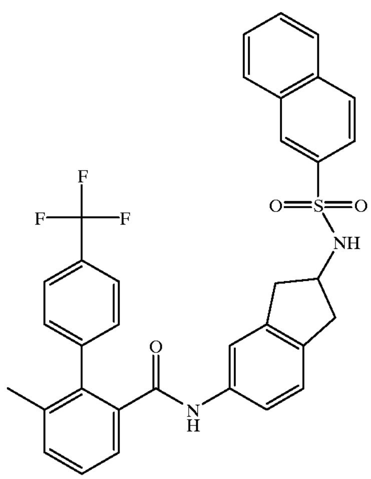 | 501[M + 1] | 102–105 |
| (dg) | 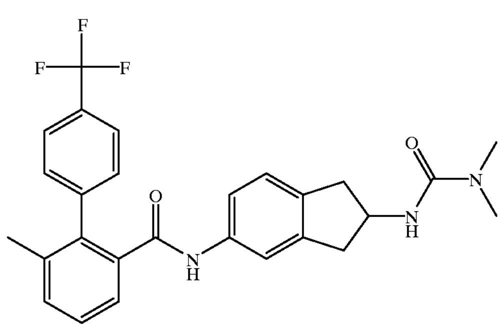 | 482[M + 1] | 243–248 |

-continued
| Compound | Structure | MS[m/z] | MP (° C.) |
|---|---|---|---|
| (dh) | 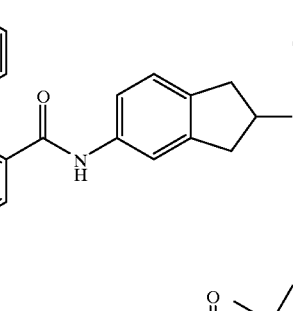 | 483[M + 1] | 167–170 |
| (di) | 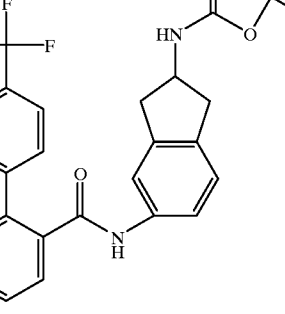 | 544 [M + NH$_4^+$] | 162–163 |
| (dj) | 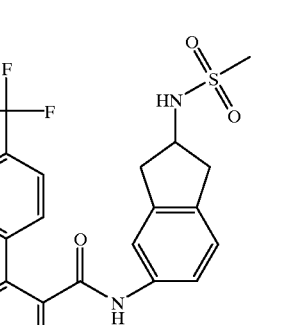 | 505[M + 1] | 95–98 |
| (dk) | 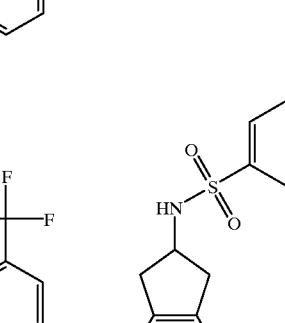 | 567[M + 1] | 197–198 |

-continued
| Compound | Structure | MS[m/z] | MP (° C.) |
|---|---|---|---|
| (dl) | 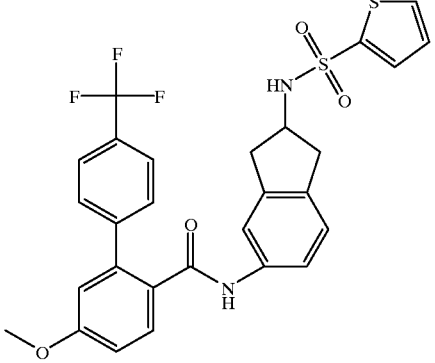 | 573[M + 1] | 192–193 |
| (dm) | 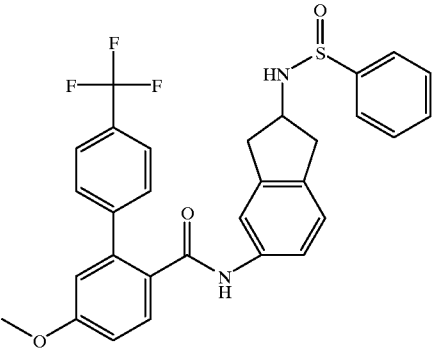 | 531[M + 1] | 218–219 |
| (dn) | 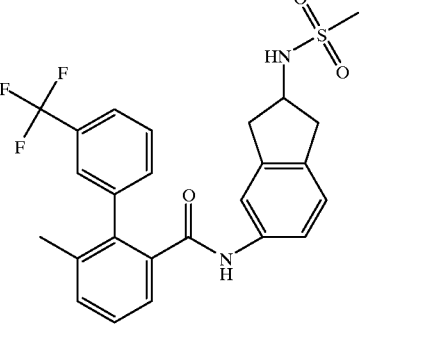 | 489[M + 1] | 111–114 |
| (do) | 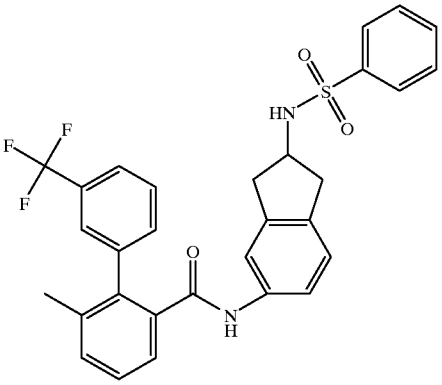 | 551[M + 1] | 105–108 |

-continued

| Compound | Structure | MS[m/z] | MP (° C.) |
|---|---|---|---|
| (dp) | 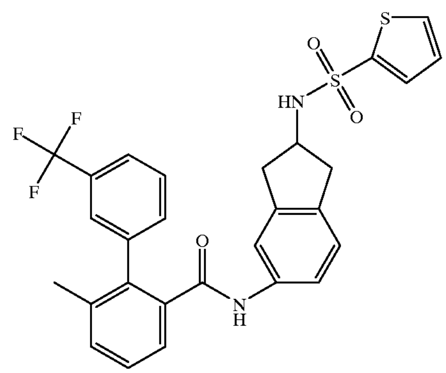 | 557[M + 1] | 100–103 |
| (dq) | 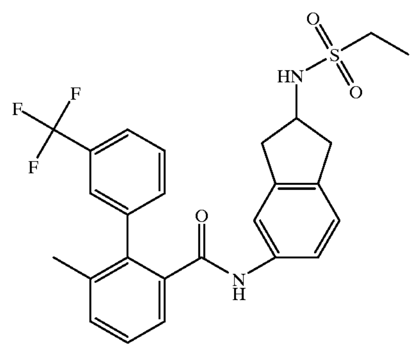 | 520[M + 1] | 90–93 |
| (dr) | 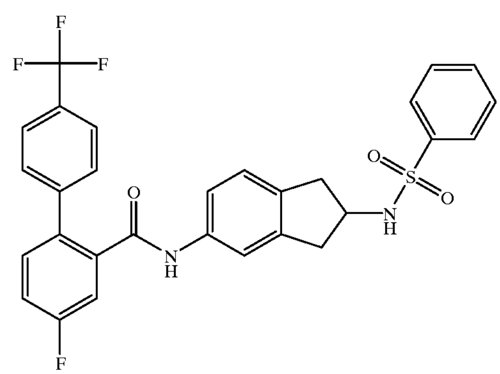 | 572[M + 1] | 95–110 |
| (ds) | 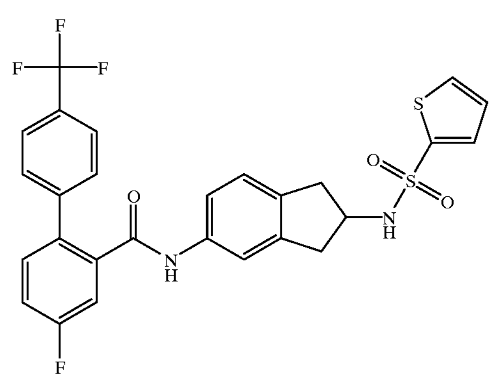 | 578[M + 1] | 95–105 |

-continued

| Compound | Structure | MS[m/z] | MP (° C.) |
|---|---|---|---|
| (dt) | 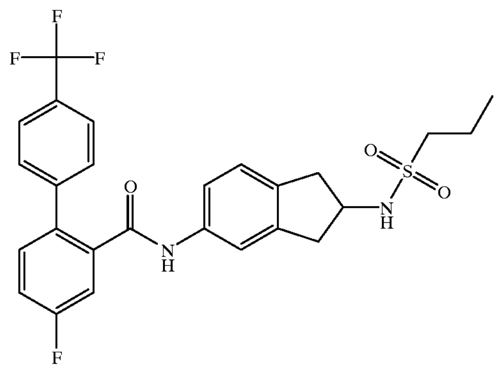 | 521[M + 1] | 141–146 |
| (du) | 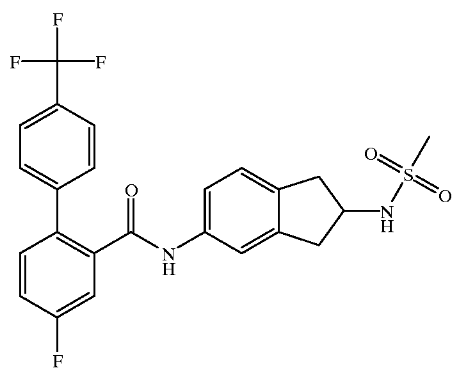 | 510[M + 1] | 155–157 |
| (dv) | 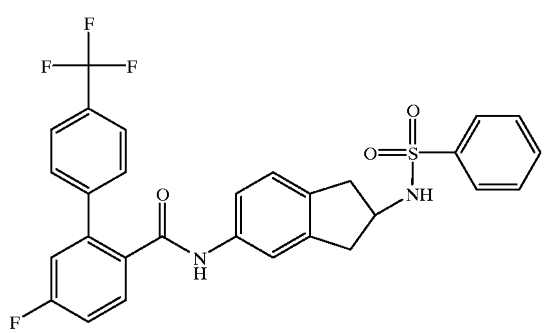 | 572 [M + NH$_4^+$] | 176–181 |
| (dw) | 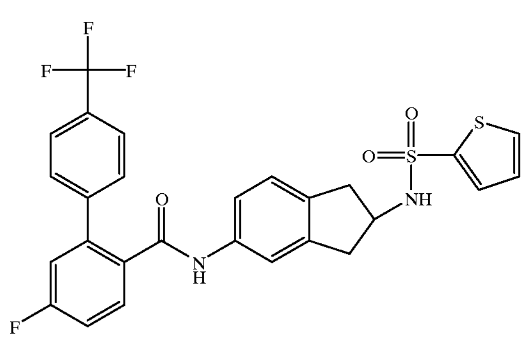 | 578 [M + NH$_4^+$] | 105–115 |

-continued

| Compound | Structure | MS[m/z] | MP (° C.) |
|---|---|---|---|
| (dx) | 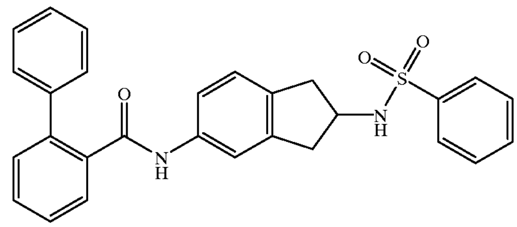 | 469[M + 1] | 100–103 |
| (dy) | 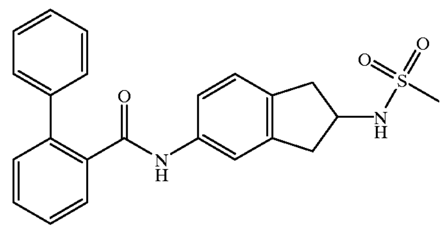 | 407[M + 1] | 171–173 |
| (dz) | 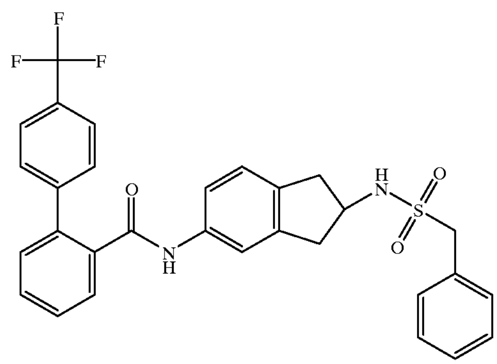 | 551[M + 1] | 165–167 |
| (ea) | 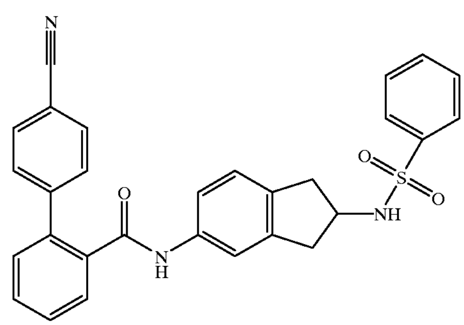 | 494[M + 1] | 98–102 |
| (eb) | 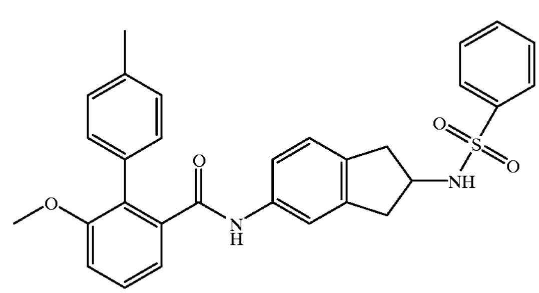 | 513[M + 1] | 147–150 |

-continued
| Compound | Structure | MS[m/z] | MP (° C.) |
|---|---|---|---|
| (ec) | 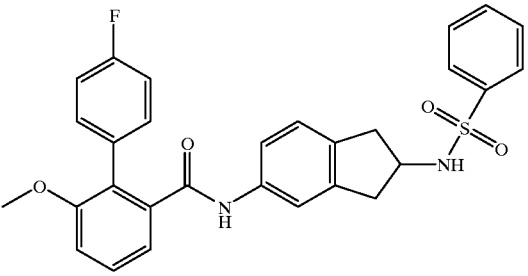 | 517[M + 1] | 193–195 |
| (ed) | 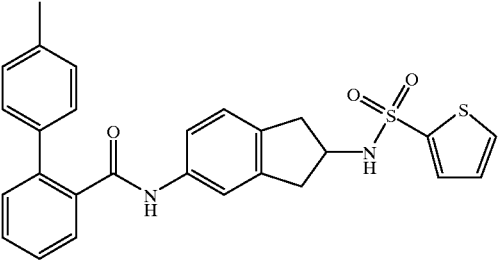 | 489[M + 1] | 92–103 |
| (ee) | 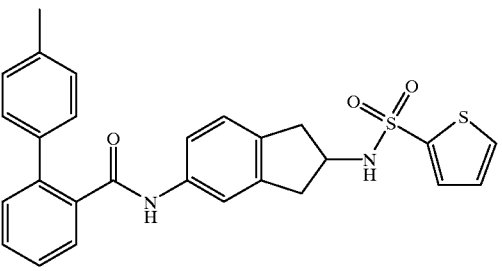 | 518[M + 1] | 224–226 |
| (ef) | 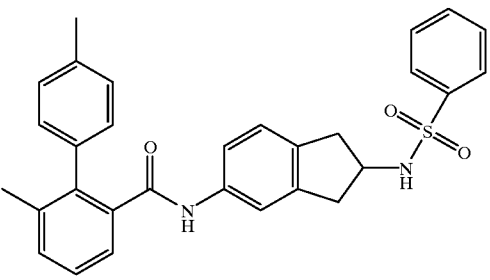 | 497[M + 1] | 104–107 |
| (eg) | 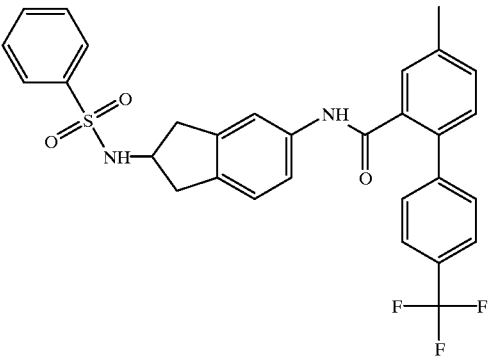 | 551[M + 1] | 83–101 |

|Compound|Structure|MS[m/z]|MP (° C.)|
|---|---|---|---|
|(eh)| 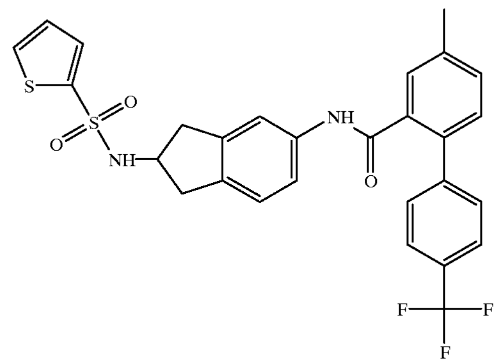 |557[M + 1]|83–99|
|(ei)| 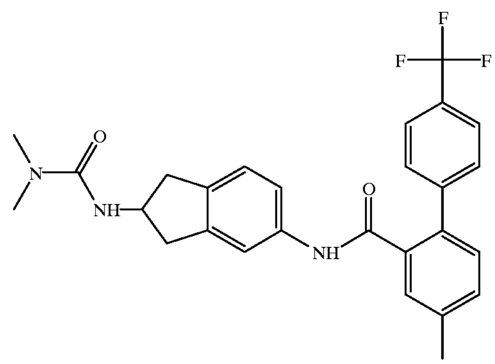 |482[M + 1]|102–110|
|(ej)| 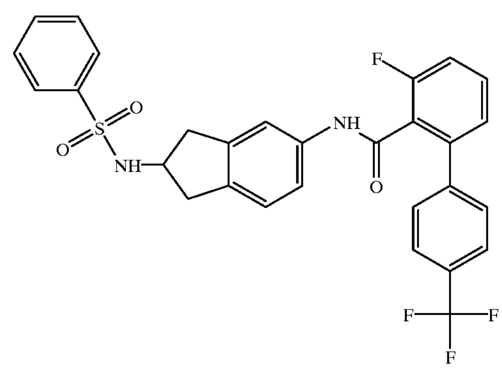 |555[M + 1]|196–200|
|(ek)| 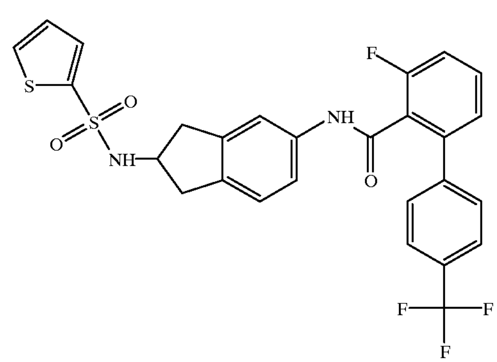 |561[M + 1]|75–89|

-continued
| Compound | Structure | MS[m/z] | MP (° C.) |
|---|---|---|---|
| (el) | 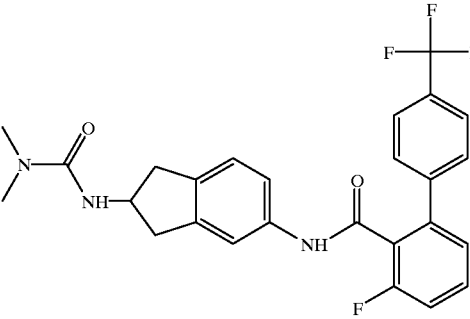 | 486[M + 1] | >230 |
| (em) | 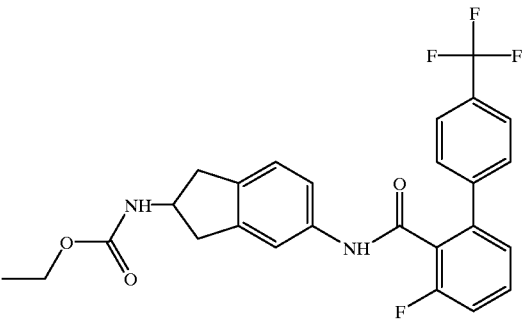 | 487[M + 1] | 90–100 |
| (en) | 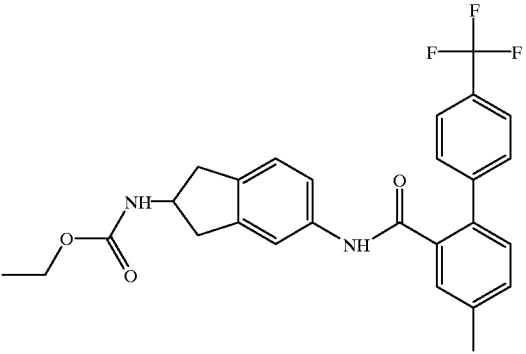 | 483[M + 1] | 80–88 |
| (eo) | 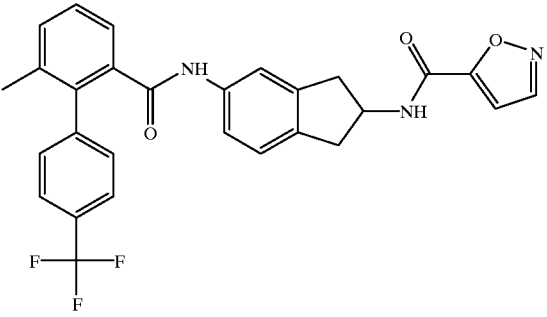 | 506[M + 1] | 105–115 |

-continued
| Compound | Structure | MS[m/z] | MP (° C.) |
|---|---|---|---|
| (ep) | 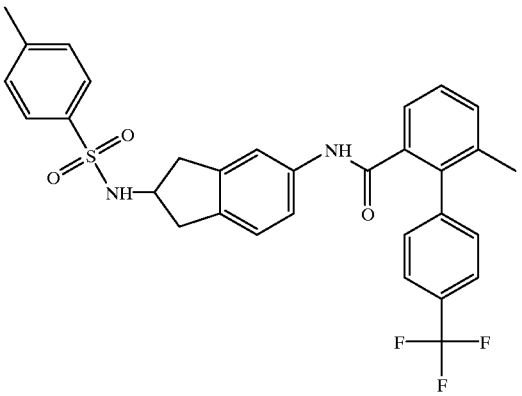 | 565[M + 1] | 90–95 |
| (eq) | 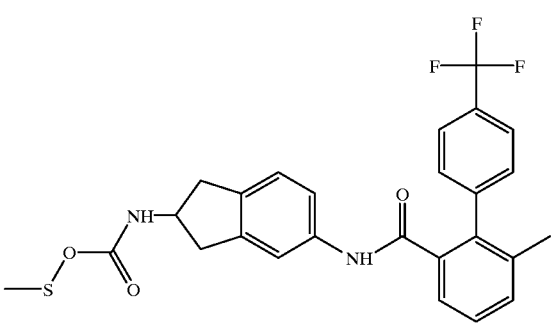 | 499[M + 1] | 189–191 |
| (er) | 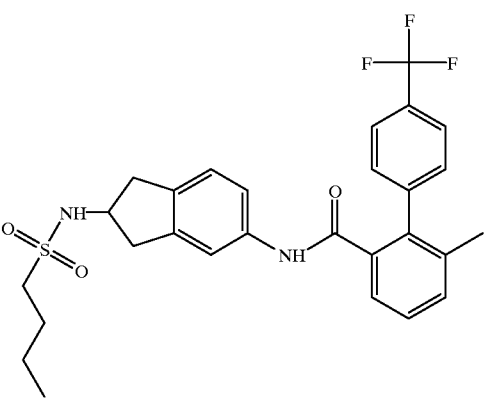 | 531[M + 1] | 209–211 |
| (es) | 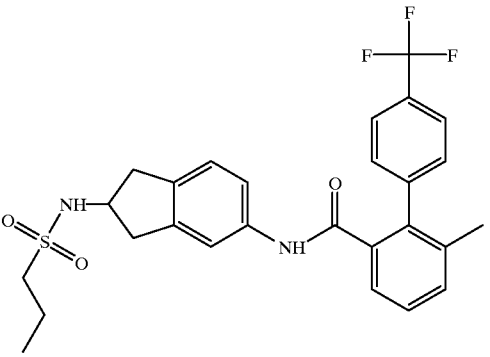 | 517[M + 1] | 208–213 |

-continued
| Compound | Structure | MS[m/z] | MP (° C.) |
|---|---|---|---|
| (et) | 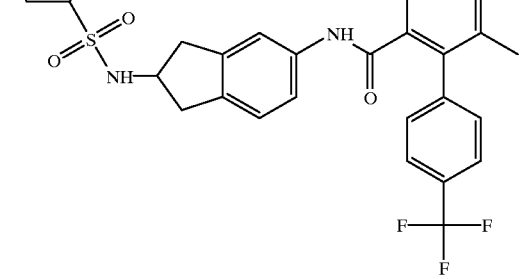 | 569[M + 1] | 176–178 |
| (eu) | 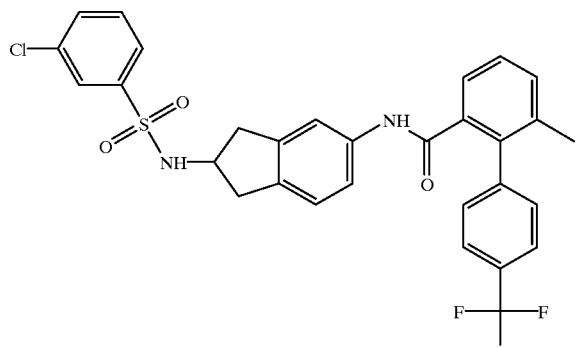 | 585[M + 1] | 99–101 |
| (ev) | 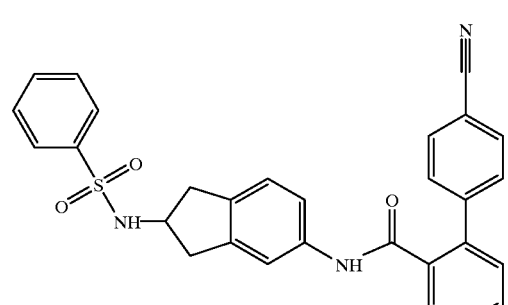 | 494[M + 1] | 98–102 |
| (ew) | 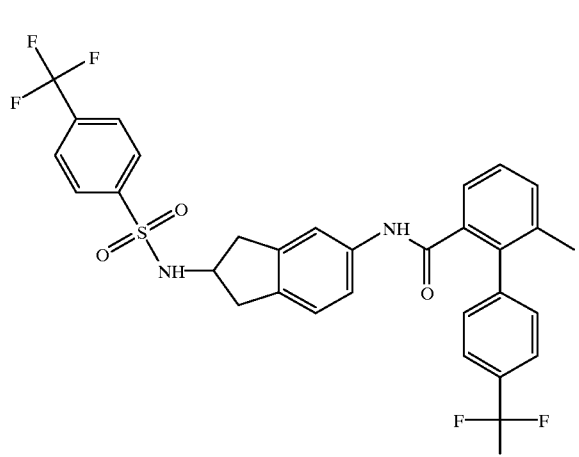 | | 98–100 |

-continued
| Compound | Structure | MS[m/z] | MP (° C.) |
|---|---|---|---|
| (ex) | 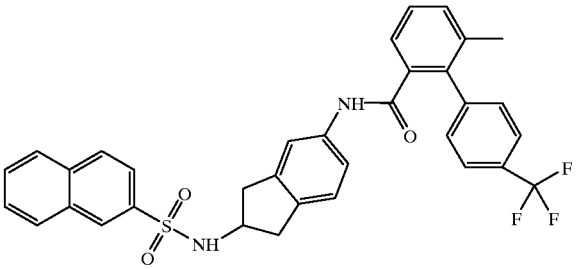 | 601[M + 1] | |
| (ey) | 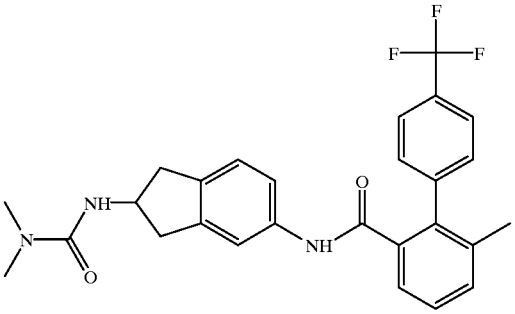 | 482[M + 1] | 243–248 |
| (ez) | 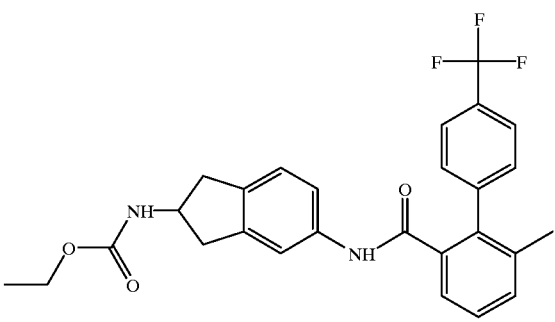 | 483[M + 1] | 167–170 |
| (fa) | 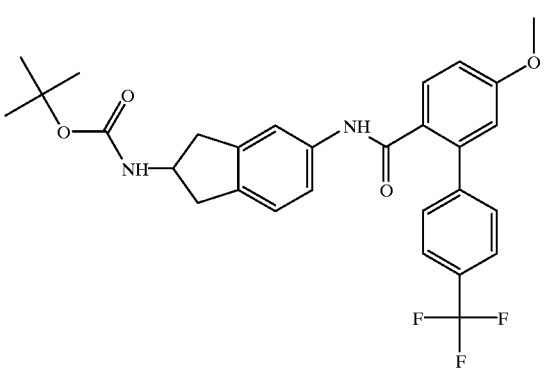 | 544 [M + NH$_4^+$] | 162–163 |

-continued

| Compound | Structure | MS[m/z] | MP (° C.) |
|---|---|---|---|
| (fb) | 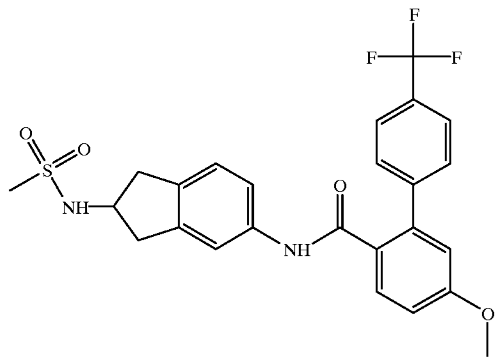 | 505[M + 1] | 92–94 |
| (fc) | 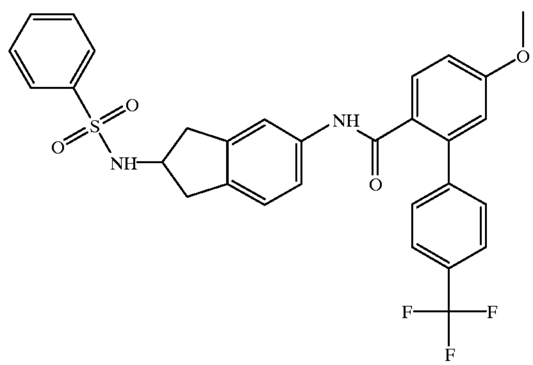 | 567[M + 1] | 196–197 |
| (fd) | 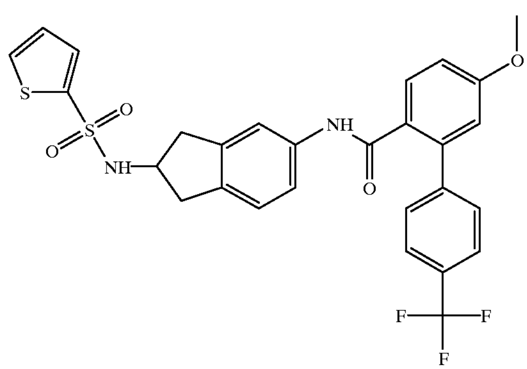 | 573[M + 1] | 194–195 |
| (fe) | 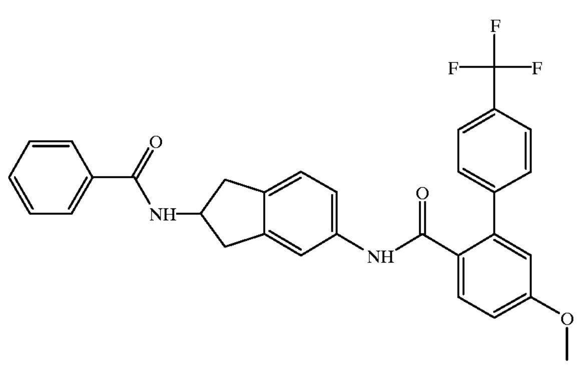 | 531[M + 1] | 219–220 |

-continued

| Compound | Structure | MS[m/z] | MP (° C.) |
|---|---|---|---|
| (ff) | 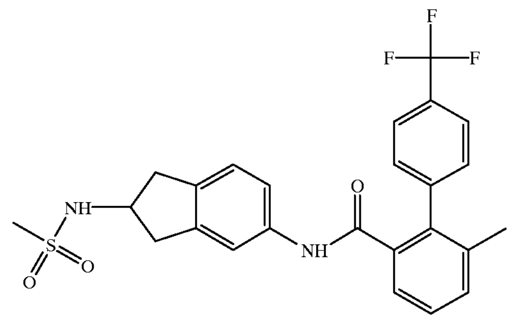 | 489[M + 1] | 169–174 |
| (fg) | 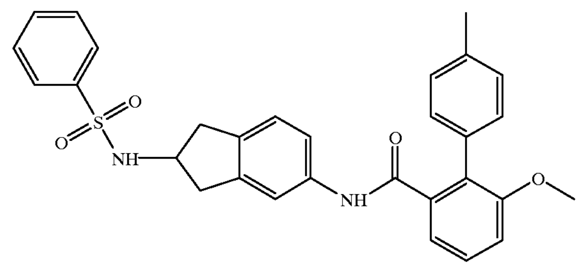 | 513[M + 1] | 147–150 |
| (fh) | 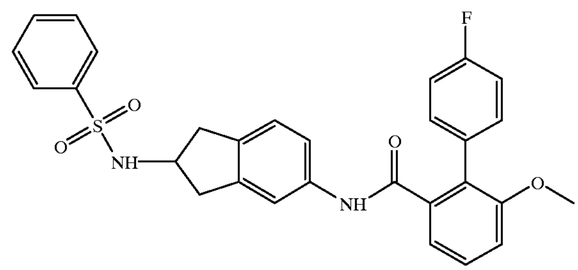 | 517[M + 1] | 193–195 |
| (fi) | 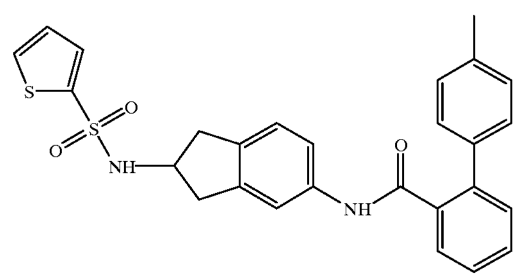 | 489[M + 1] | 92–103 |
| (fj) | 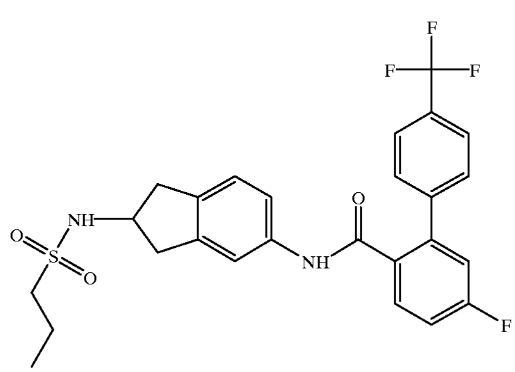 | 538 [M + NH$_4^+$] | 199–200 |

-continued

| Compound | Structure | MS[m/z] | MP (° C.) |
|---|---|---|---|
| (fk) | 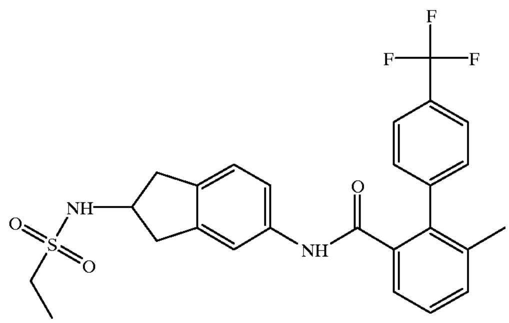 | 503[M + 1] | 177–194 |
| (fl) | 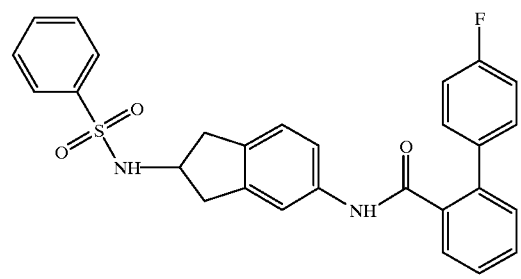 | 487[M + 1] | 98–115 |
| (fm) | 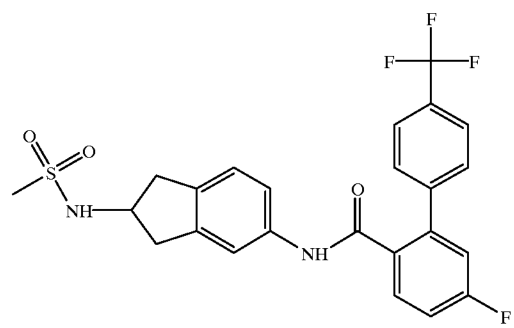 | 510 [M + NH$_4^+$] | 180–183 |
| (fn) | 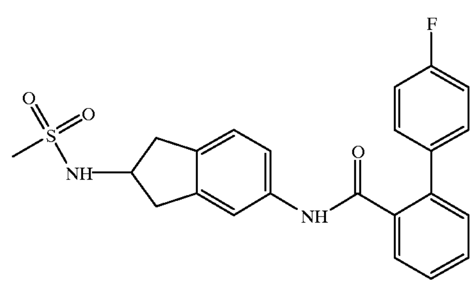 | 425[M + 1] | 187–189 |
| (fo) | 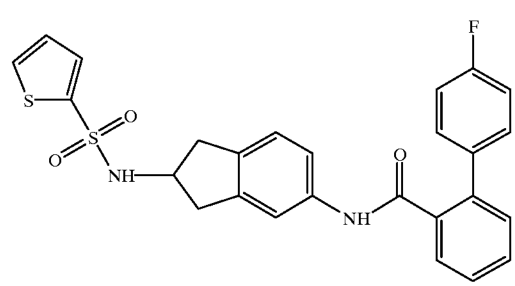 | 493[M + 1] | 101–111 |

-continued

| Compound | Structure | MS[m/z] | MP (° C.) |
| --- | --- | --- | --- |
| (fp) | 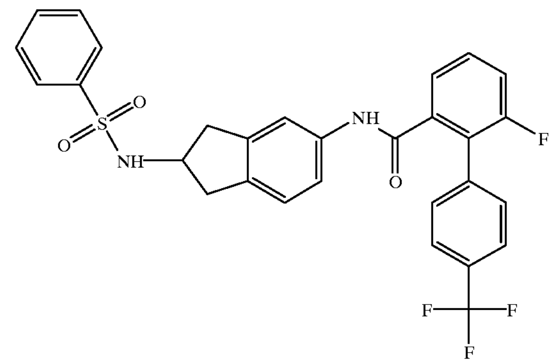 | 555[M + 1] | 188–189 |
| (fq) | 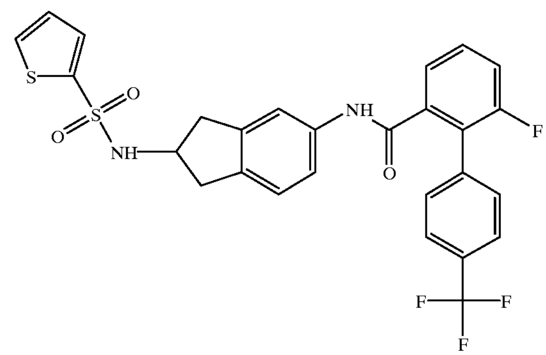 | 561[M + 1] | 181–182 |
| (fr) | 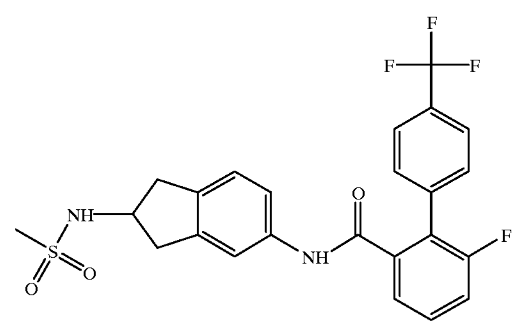 | 493[M + 1] | 196–197 |
| (fs) | 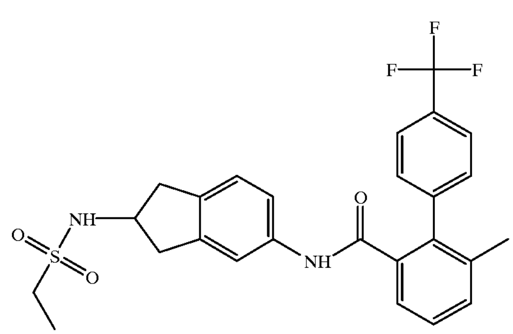 | 503[M + 1] | 195–199 |

-continued

| Compound | Structure | MS[m/z] | MP (° C.) |
|---|---|---|---|
| (ft) | 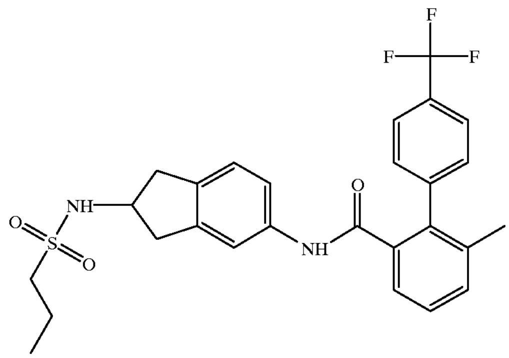 | 517[M + 1] | 208–210 |
| (fu) | 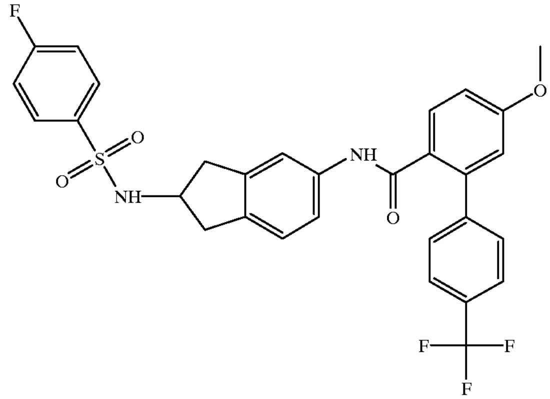 | 585[M + 1] | 97–100 |
| (fv) | 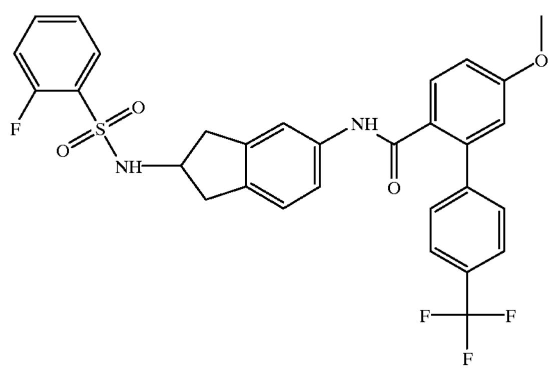 | 585[M + 1] | 92–96 |
| (fw) | 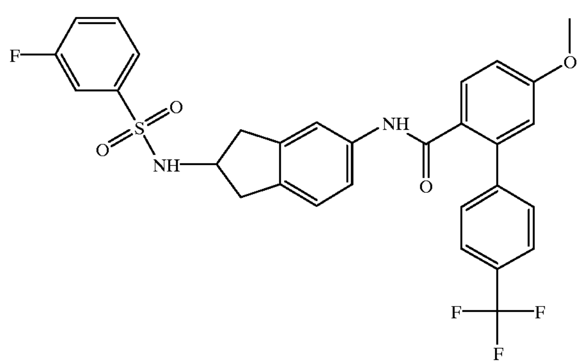 | 585[M + 1] | 98–102 |

-continued
| Compound | Structure | MS[m/z] | MP (° C.) |
|---|---|---|---|
| (fx) | 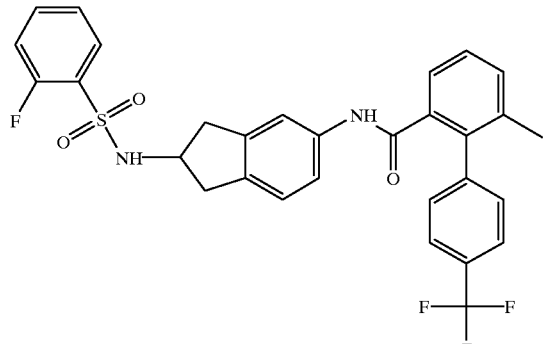 | 569[M + 1] | 98–101 |
| (fy) | 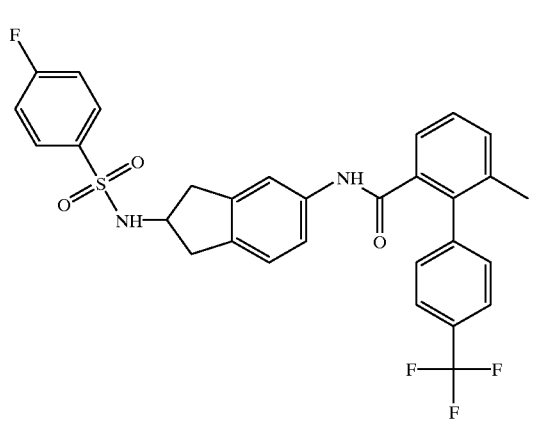 | 569[M + 1] | 181–182 |
| (fz) | 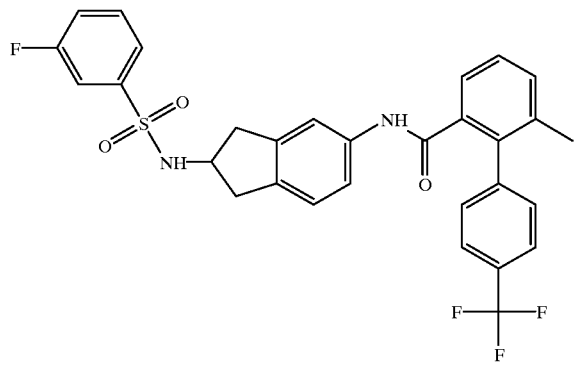 | 569[M + 1] | 101–104 |
| (ga) | 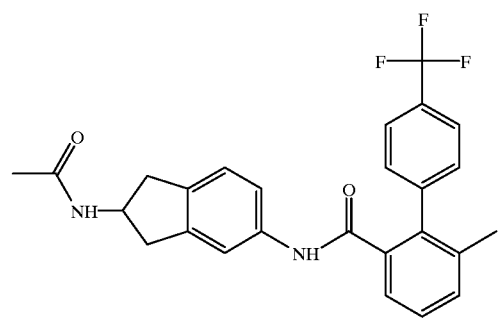 | 453[M + 1] | 196–197 |

-continued

| Compound | Structure | MS[m/z] | MP (° C.) |
|---|---|---|---|
| (gb) | 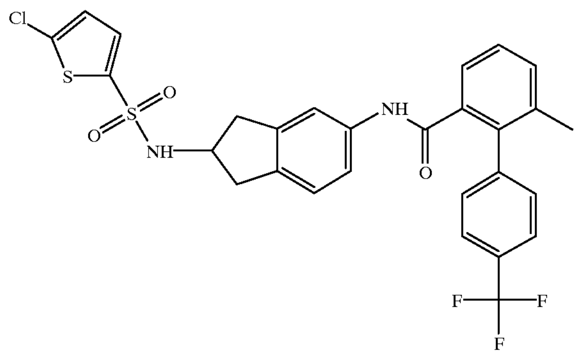 | 591[M + 1] | 97–100 |
| (gc) | 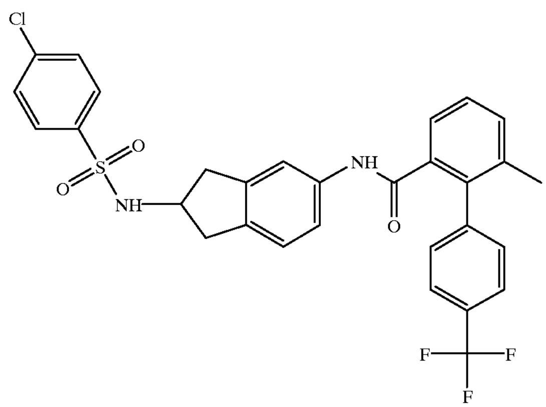 | 585[M + 1] | 105–108 |
| (gd) | 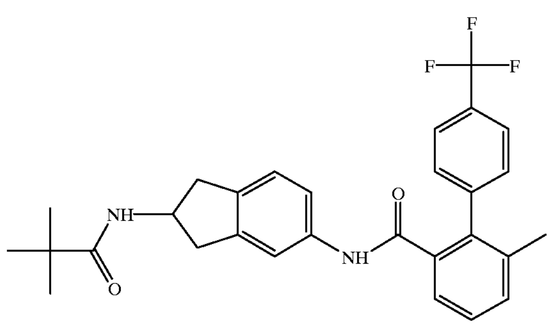 | 495[M + 1] | 212–213 |
| (ge) | 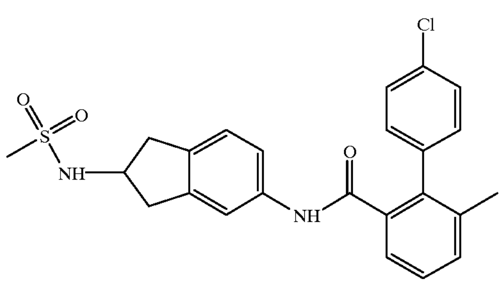 | 455[M + 1] | 160–163 |

-continued

| Compound | Structure | MS[m/z] | MP (° C.) |
|---|---|---|---|
| (gf) | 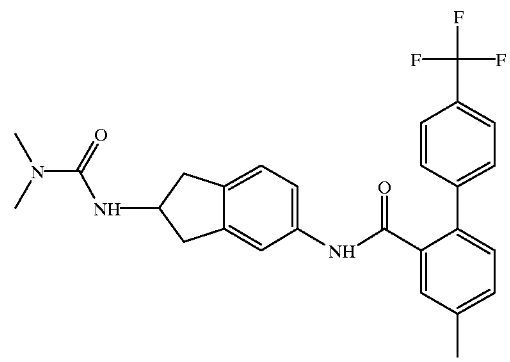 | 482[M + 1] | 89–96 |
| (gg) | 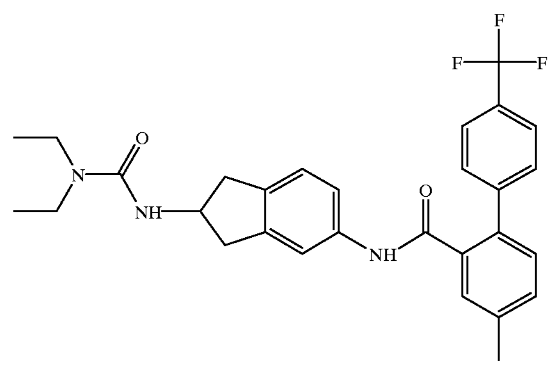 | 510[M + 1] | oil |
| (gh) | 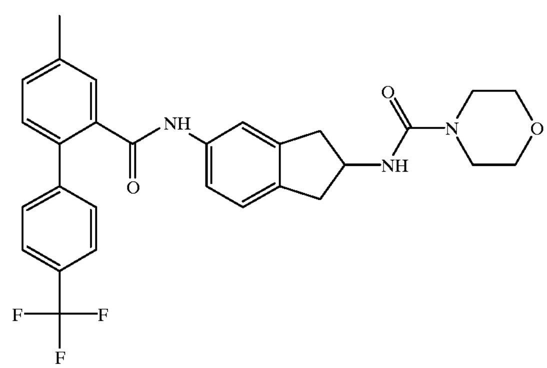 | 524[M + 1] | 175–182 |
| (gi) | 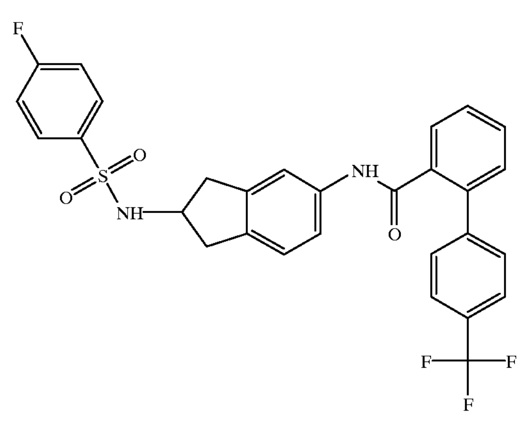 | 572 [M + NH$_4^+$] | 188–189 |

-continued

| Compound | Structure | MS[m/z] | MP (° C.) |
|---|---|---|---|
| (gj) | 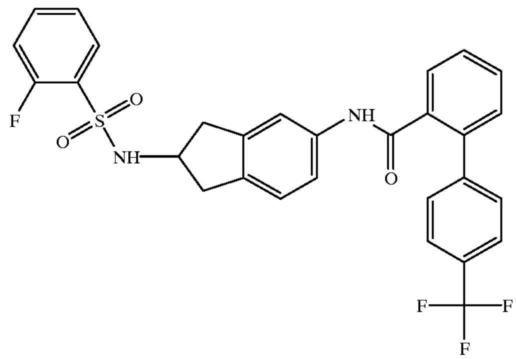 | 572 [M + NH$_4^+$] | 171–172 |
| (gk) | 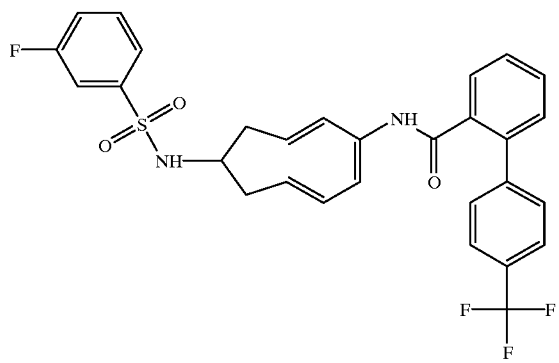 | 572 [M + NH$_4^+$] | 173–174 |
| (gl) | 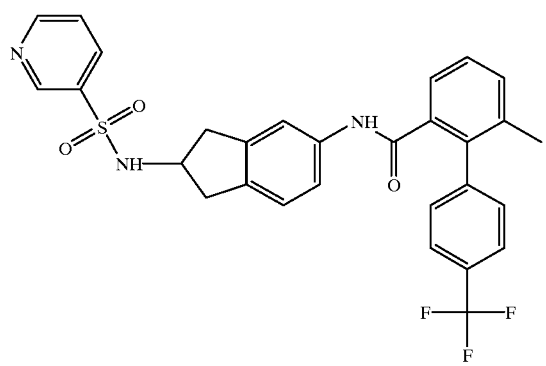 | 552[M + 1] | 109–119 |
| (gm) | 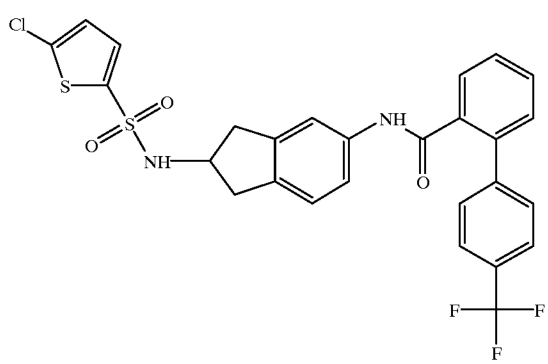 | 594 [M + NH$_4^+$] | 93–95 |

-continued

| Compound | Structure | MS[m/z] | MP (° C.) |
|---|---|---|---|
| (gn) | 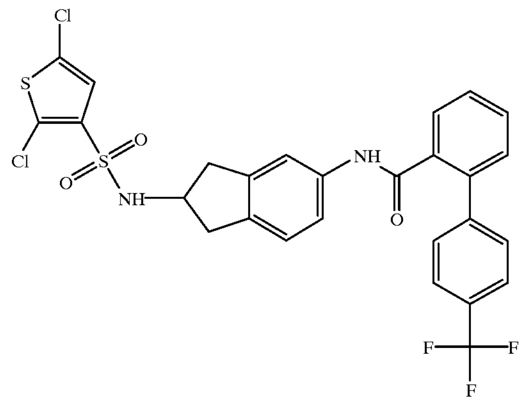 | 628 [M + NH$_4^+$] | 102–104 |
| (go) | 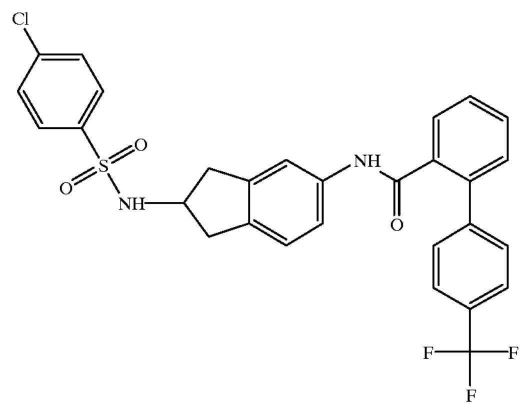 | 588 [M + NH$_4^+$] | 210–211 |
| (gp) | 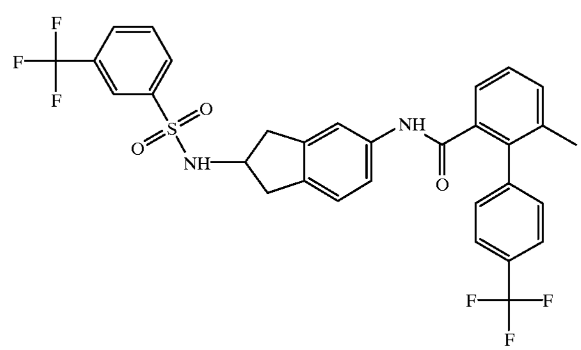 | 636 [M + NH$_4^+$] | 90–93 |

-continued
| Compound | Structure | MS[m/z] | MP (° C.) |
|---|---|---|---|
| (gq) | 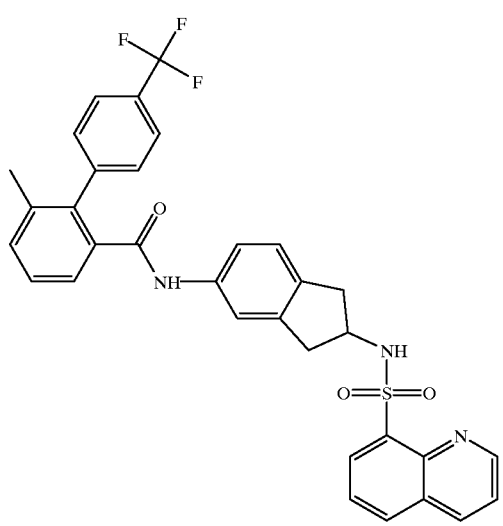 | 602[M + 1] | 119–119 |
| (gr) | 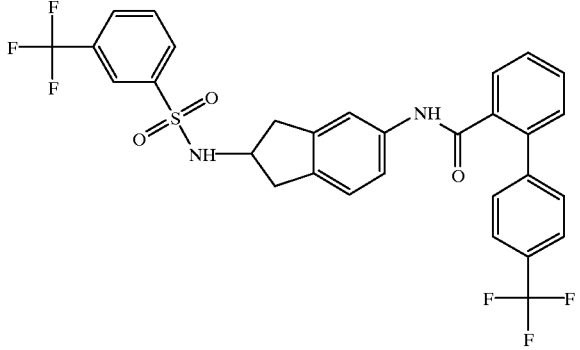 | 622 [M + NH$_4^+$] | 94–97 |
| (gs) | 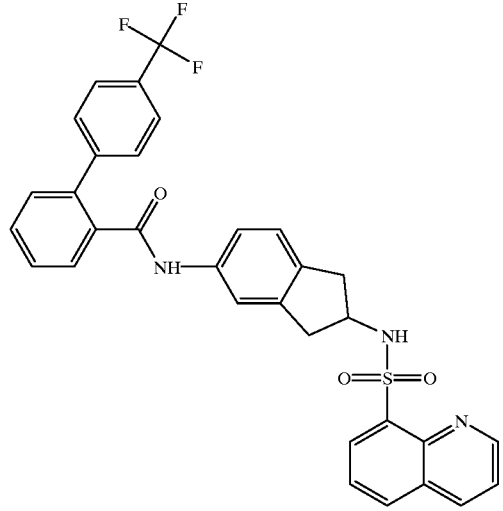 | 588[M + 1] | 125–127 |

-continued
| Compound | Structure | MS[m/z] | MP (° C.) |
|---|---|---|---|
| (gt) | 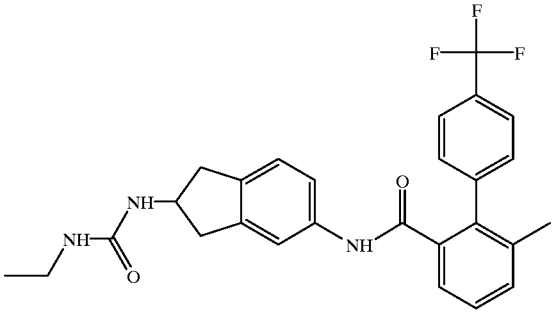 | 482[M + 1] | 254–255 |
| (gu) | 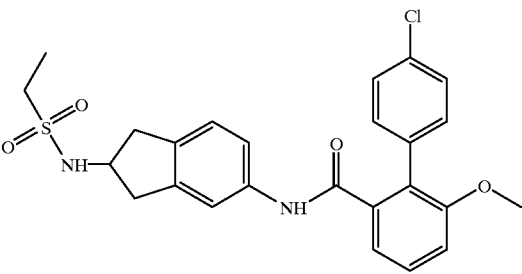 | 486[M + 1] | 99–102 |
| (gv) | 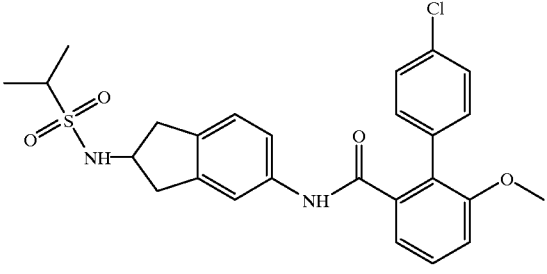 | 500[M + 1] | 207–210 |
| (gw) | 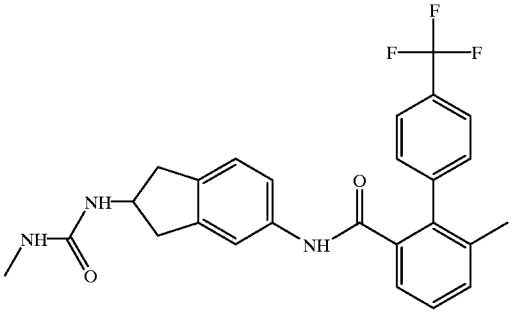 | 468[M + 1] | 251–252 |
| (gx) | 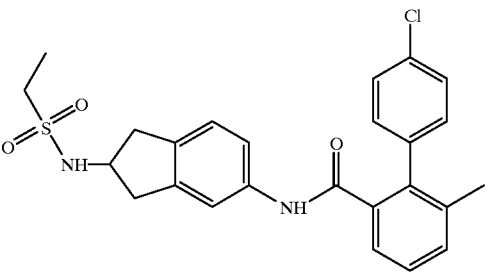 | 470[M + 1] | 182–186 |

-continued

| Compound | Structure | MS[m/z] | MP (° C.) |
|---|---|---|---|
| (gy) | 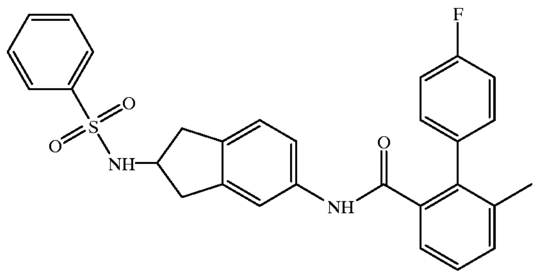 | 501[M + 1] | 192–195 |
| (gz) | 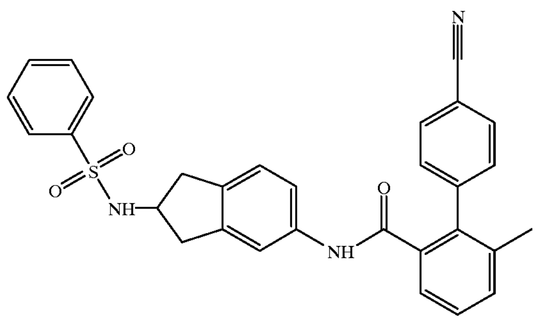 | 508[M + 1] | 133–136 |
| (ha) | 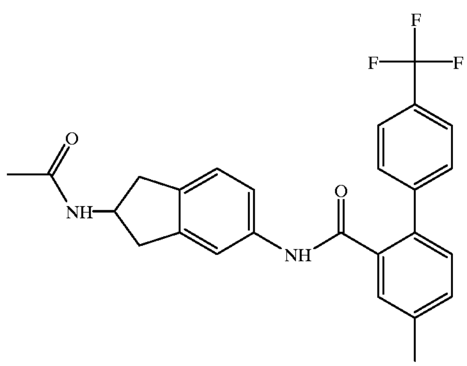 | 453[M + 1] | 180–181 |
| (hb) | 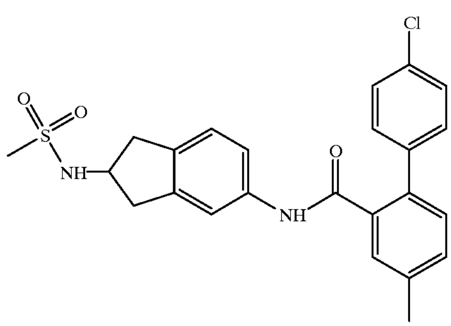 | 455[M + 1] | 190–192 |

-continued

| Compound | Structure | MS[m/z] | MP (° C.) |
|---|---|---|---|
| (hc) | 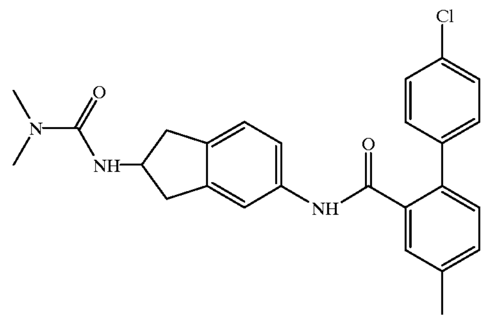 | 448[M + 1] | 203–204 |
| (hd) | 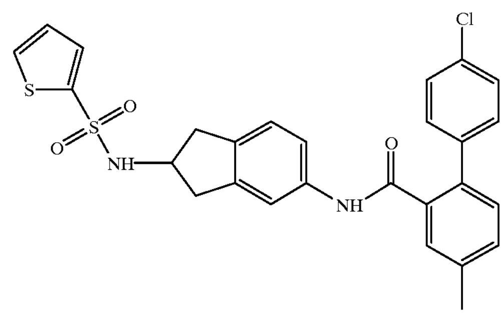 | 525[M + 1] | 110–114 |
| (he) | 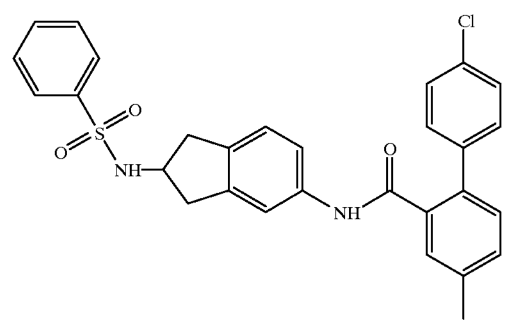 | 518[M + 1] | 80 foam |
| (hf) | 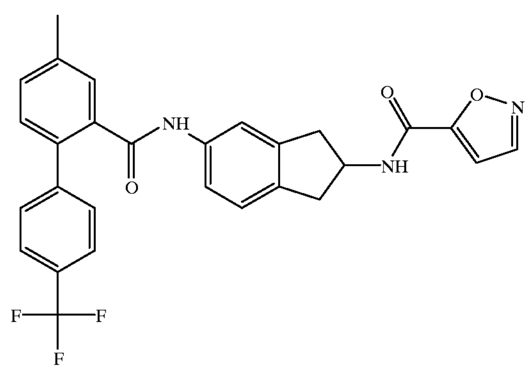 | 506[M + 1] | 100–108 |

-continued

| Compound | Structure | MS[m/z] | MP (° C.) |
|---|---|---|---|
| (hg) | 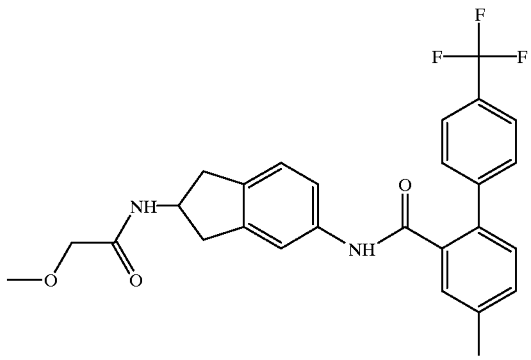 | 483[M + 1] | 80–86 |
| (hh) | 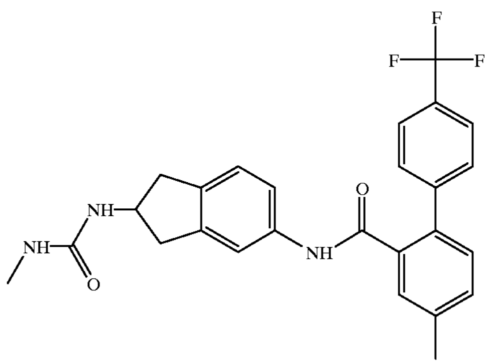 | 468[M + 1] | 243–248 |
| (hi) | 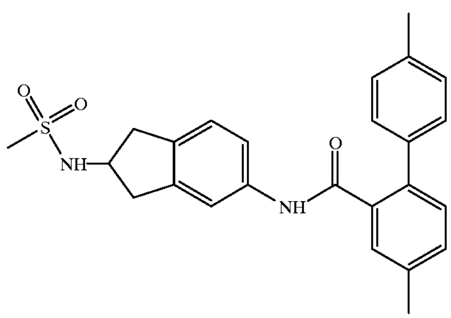 | 435[M + 1] | 203–205 |
| (hj) | 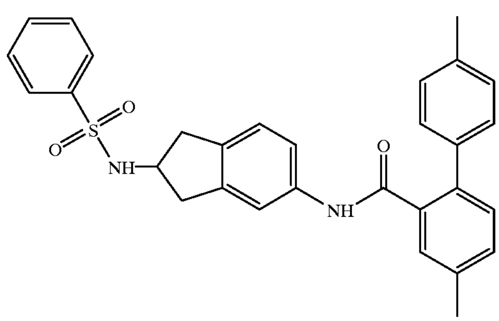 | 497[M + 1] | 102–105 |

-continued
| Compound | Structure | MS[m/z] | MP (° C.) |
|---|---|---|---|
| (hk) | 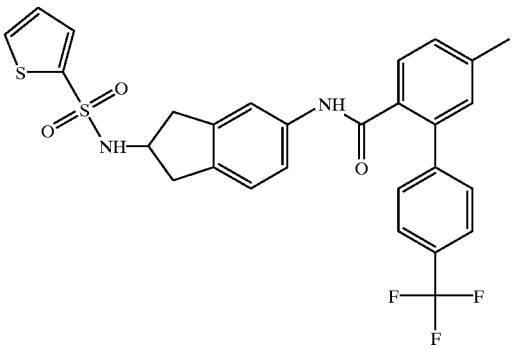 | 557[M + 1] | 184–188 |
| (hl) | 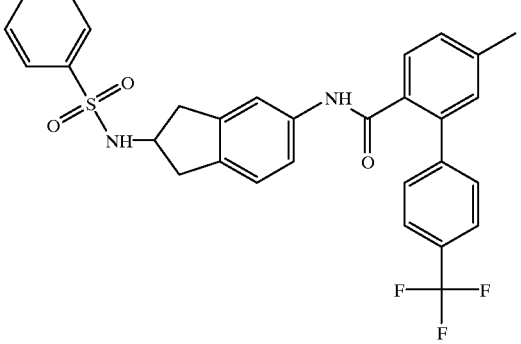 | 551[M + 1] | 198–203 |
| (hm) | 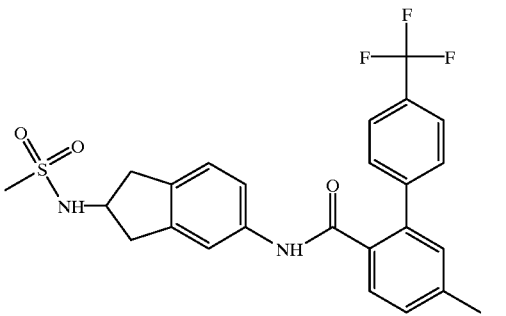 | 489[M + 1] | 168–174 |
| (hn) | 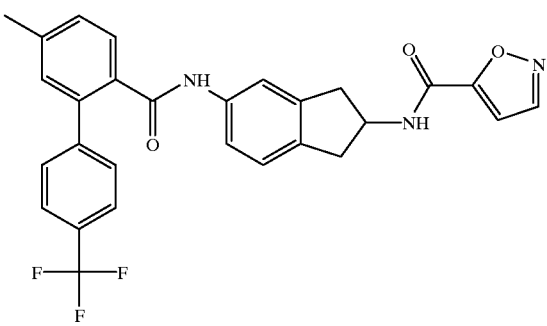 | 506[M + 1] | 110–120 |

-continued
| Compound | Structure | MS[m/z] | MP (° C.) |
| --- | --- | --- | --- |
| (ho) | 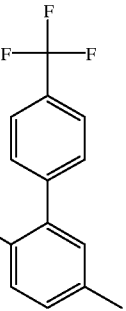 | 482[M + 1] | 229–232 |
| (hp) | 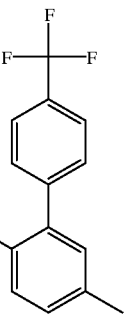 | 483[M + 1] | 176–180 |
| (hq) | 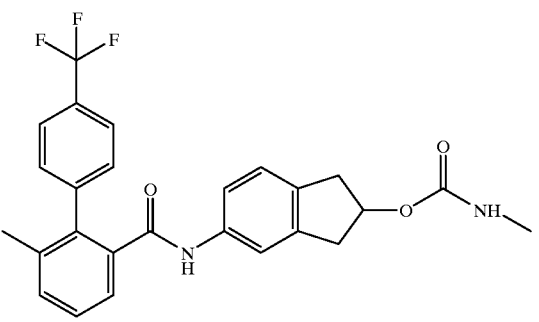 | 469[M + 1] | foam |
| (hr) | 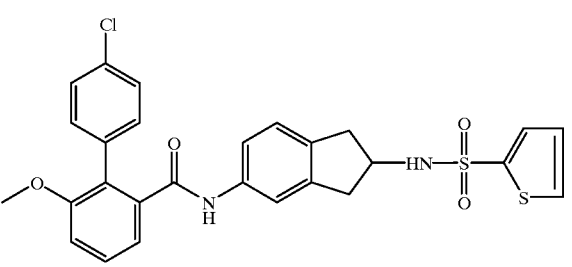 | 540[M + 1] | 172–173 |
| (hs) | 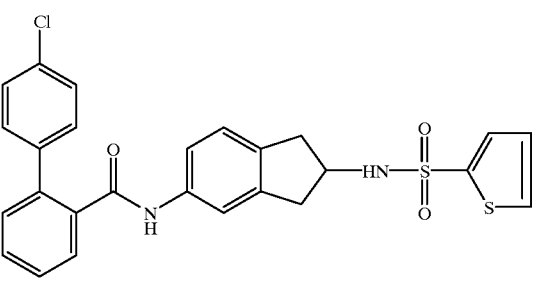 | 510[M + 1] | 155–158 |

-continued

| Compound | Structure | MS[m/z] | MP (° C.) |
|---|---|---|---|
| (ht) | 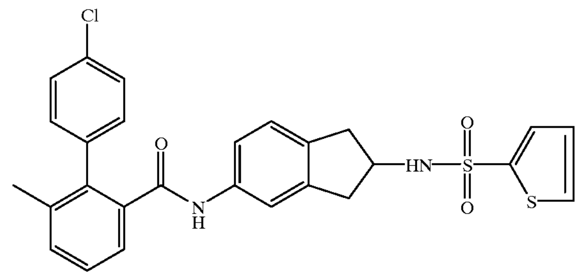 | 524[M + 1] | 217–219 |
| (hu) | 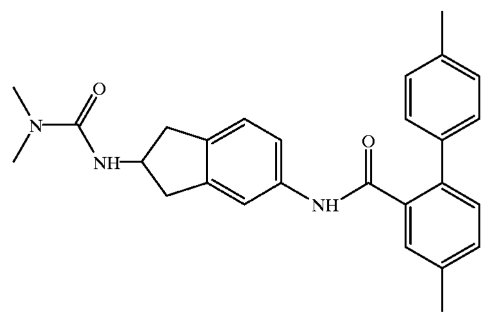 | 428[M + 1] | 191–194 |
| (hv) | 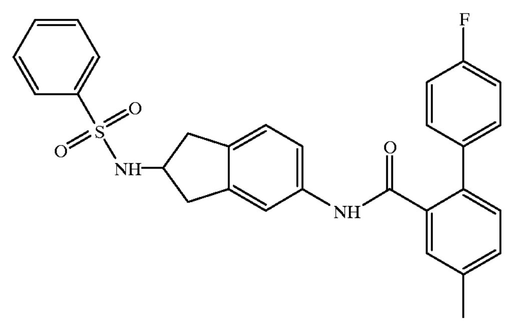 | 501[M + 1] | 107–118 |
| (hw) | 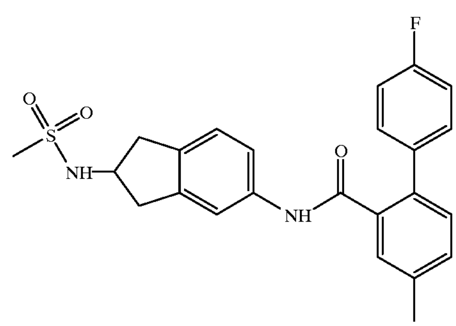 | 439[M + 1] | 189–190 |

-continued

| Compound | Structure | MS[m/z] | MP (° C.) |
|---|---|---|---|
| (hx) | 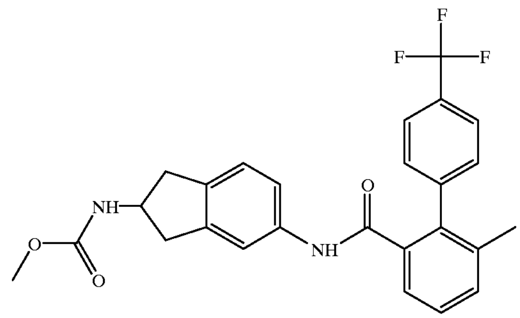 | 469[M + 1] | 112–115 |
| (hy) | 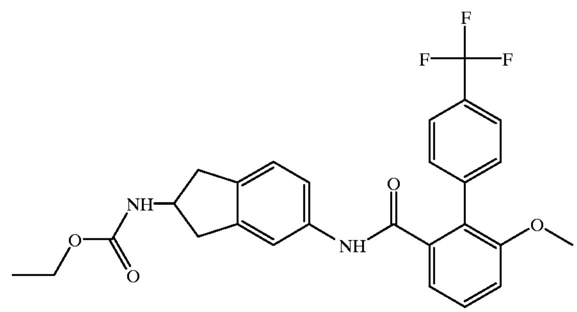 | 499[M + 1] | 77–86 |
| (hz) | 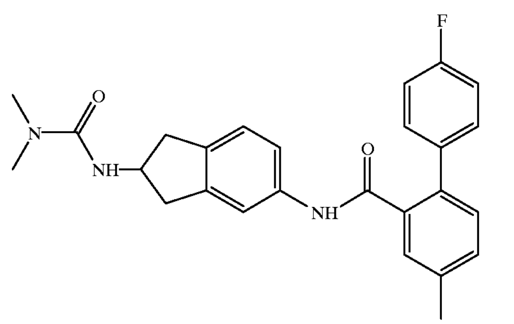 | 432[M + 1] | 191–196 |
| (ia) | 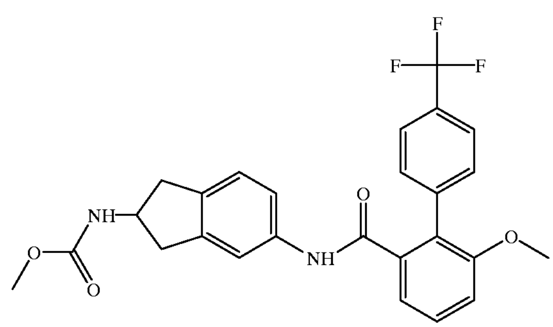 | 485[M + 1] | 77–86 |

-continued

| Compound | Structure | MS[m/z] | MP (° C.) |
|---|---|---|---|
| (ib) | 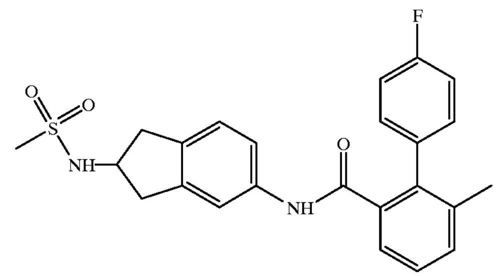 | 439[M + 1] | 208–210 |
| (ic) | 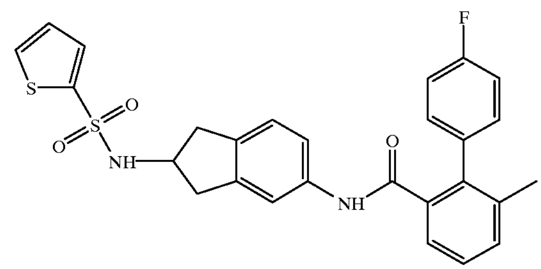 | 506[M + 1] | 104–115 |
| (id) | 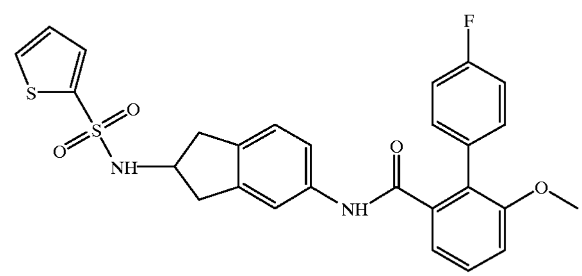 | 523[M + 1] | 193–197 |
| (ie) | 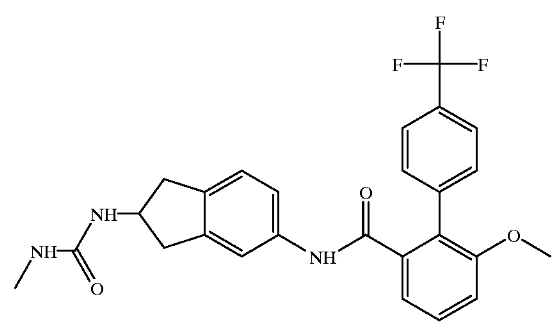 | 484[M + 1] | 251–253 |
| (if) | 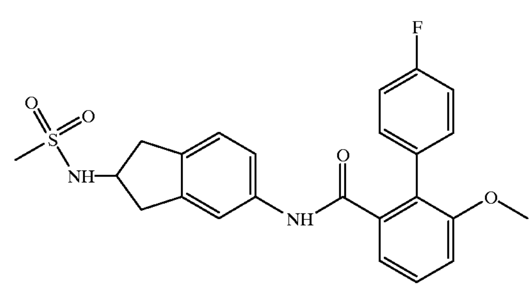 | 455[M + 1] | 170–177 |

-continued

| Compound | Structure | MS[m/z] | MP (° C.) |
|---|---|---|---|
| (ig) | 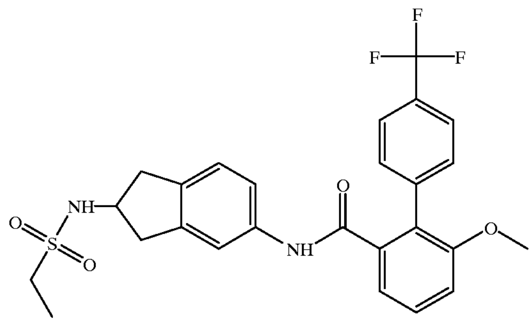 | 536 [M + NH₄⁺] | 106–109 |
| (ih) | 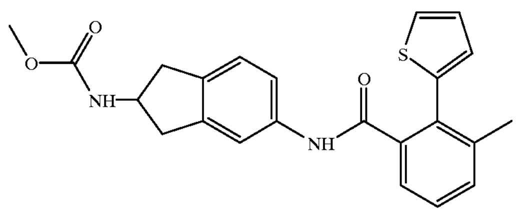 | 407[M + 1] | 66–70 |
| (ii) | 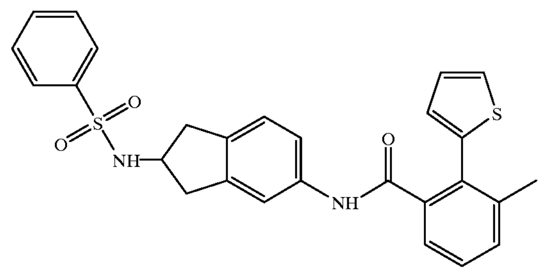 | 489[M + 1] | 79–88 |
| (ij) | 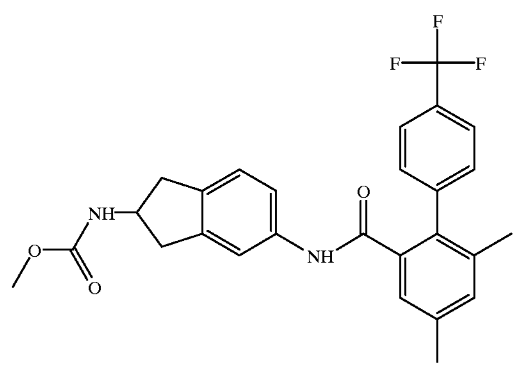 | 483[M + 1] | 149–150 |
| (ik) | 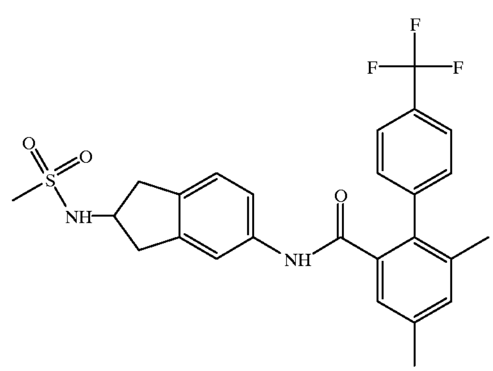 | 503[M + 1] | 100–102 |

-continued
| Compound | Structure | MS[m/z] | MP (° C.) |
|---|---|---|---|
| (il) | 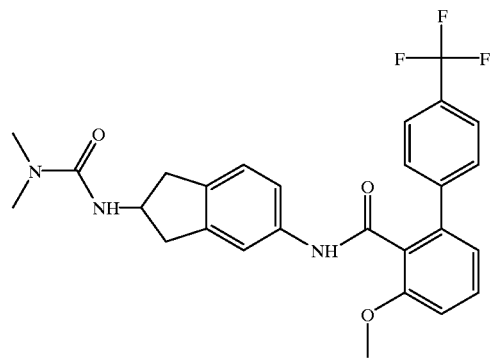 | 498[M + 1] | 250–257 |
| (im) | 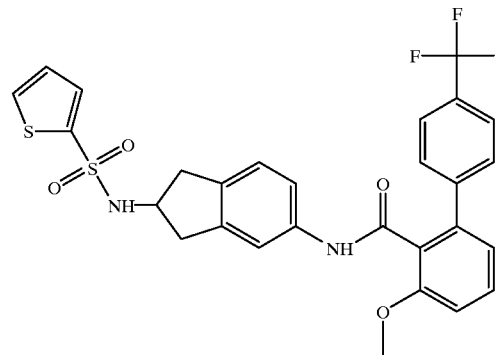 | 573[M + 1] | 85–98 |
| (in) | 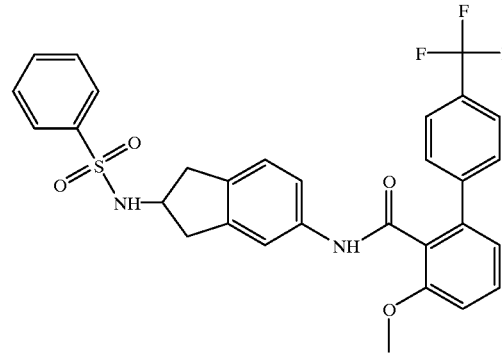 | 567[M + 1] | 59–67 |
| (io) | 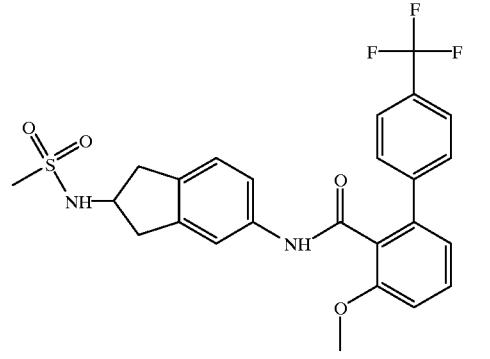 | 505[M + 1] | 65–71 |

-continued

| Compound | Structure | MS[m/z] | MP (° C.) |
|---|---|---|---|
| (ip) | 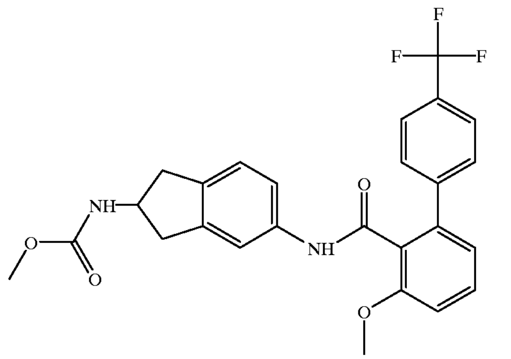 | 485[M + 1] | 94–102 |
| (iq) | 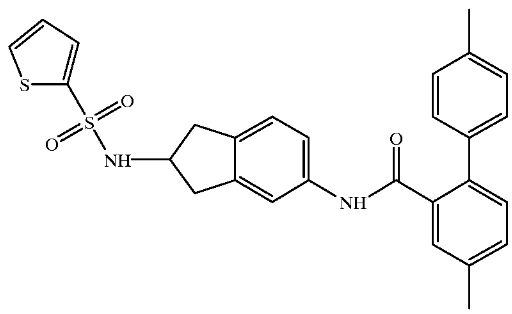 | 503[M + 1] | 99–102 |
| (ir) | 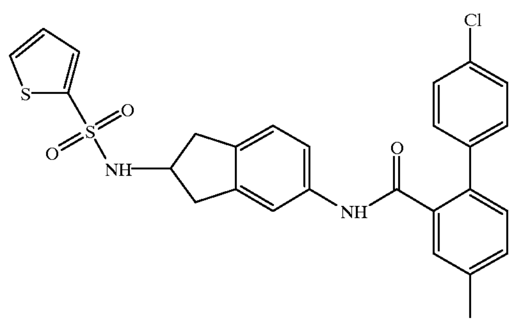 | 523[M + 1] | 110–114 |
| (is) | 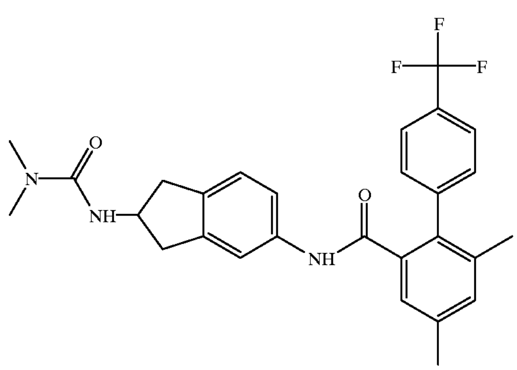 | 496[M + 1] | 196–198 |

-continued

| Compound | Structure | MS[m/z] | MP (° C.) |
|---|---|---|---|
| (it) | 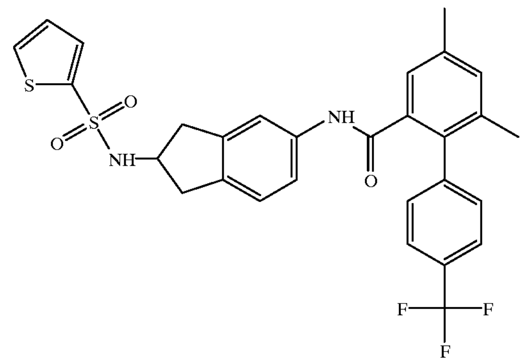 | 571[M + 1] | 104–109 |
| (iu) | 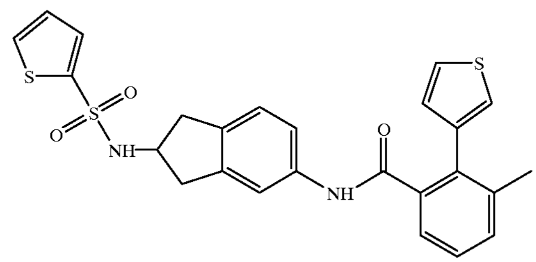 | 495[M + 1] | 88–94 |
| (iv) | 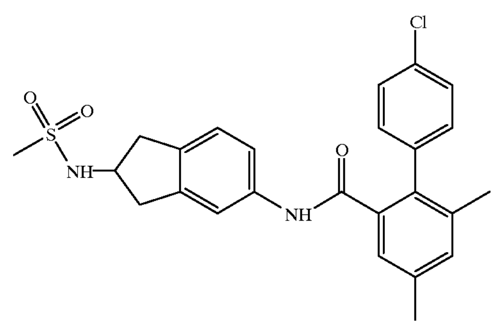 | 486 [M + NH$_4^+$] | 110–115 |
| (iw) | 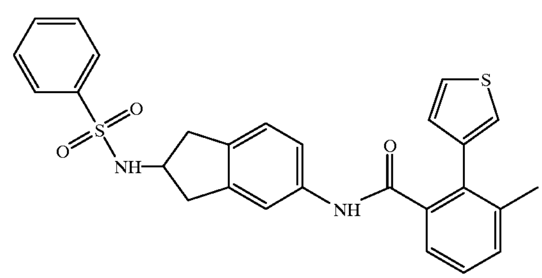 | 489[M + 1] | 85–90 |
| (ix) | 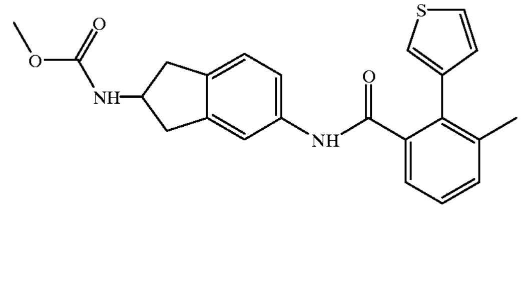 | 407[M + 1] | 80–85 |

-continued

| Compound | Structure | MS[m/z] | MP (° C.) |
|---|---|---|---|
| (iy) | 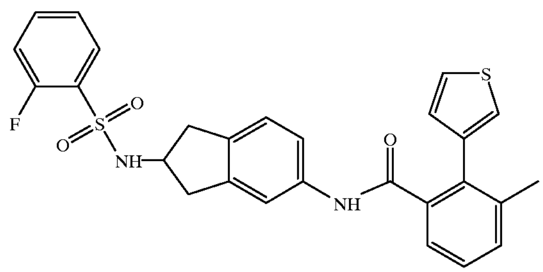 | 524 [M + NH₄⁺] | 88–91 |
| (iz) | 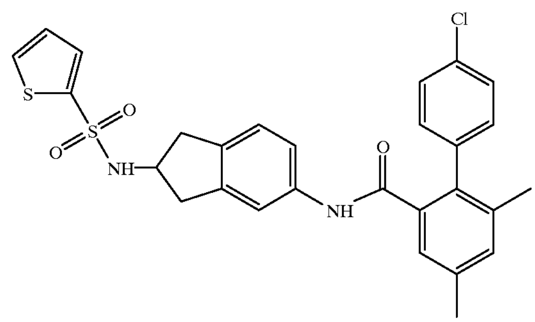 | 537[M + 1] | 90–92 |
| (ja) | 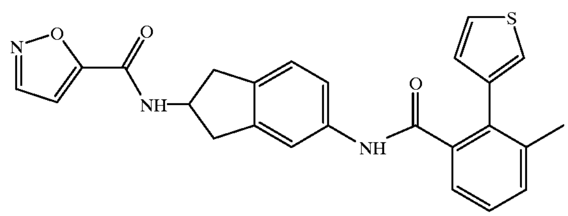 | 461 [M + NH₄] | 93–99 |
| (jb) | 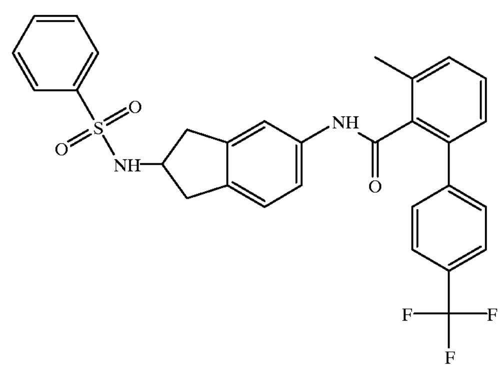 | 568 [M + NH₄⁺] | 215–216 |
| (jc) | 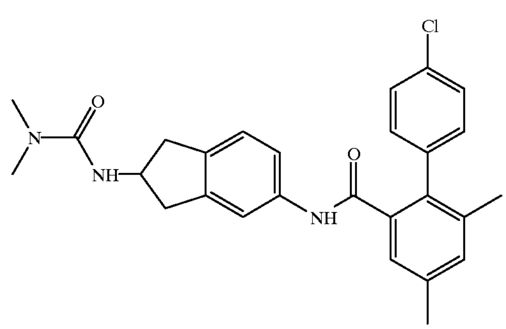 | 462[M + 1] | 115–125 |

-continued

| Compound | Structure | MS[m/z] | MP (° C.) |
|---|---|---|---|
| (jd) | 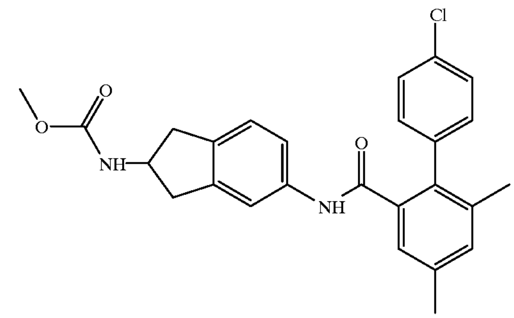 | 449[M + 1] | 136–138 |

EXAMPLE 3

4'-Fluorobiphenyl-2-carboxylic acid (2-acetylamino-indan-5-yl)-amide

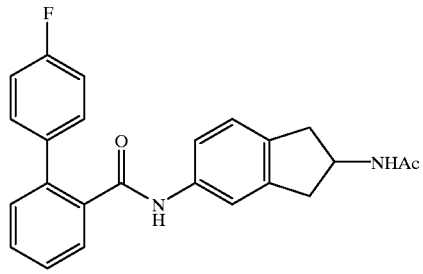

A. N-(5-Amino-indan-2-yl)-acetamide

A solution of N-(5-nitro-indan-2-yl)-acetamide (Bigge, C. F.; Retz, D. M. WO 9617832 A1) (0.37 g, 1.68 mmol) in ethanol (10 mL) is degassed and 10% palladium on carbon added (0.05 g). The reaction mixture is evacuated and placed under 1 atm $H_2(g)$ for 2 h. Fitration of the reaction mixture through Celite is followed by concentration of the filtrate under reduced pressure to give N-(5-amino-indan-2-yl)-acetamide as a white solid which is used directly without further purification. $^1$H NMR (DMSO-$d_6$, 300 MHz) δ 8.05 (1H, d), 6.82 (1H, d), 6.40 (1H, s), 6.35 (1H, d), 4.81 (2H, bs), 4.38 (1H, m), 2.98 (2H, m), 2.58 (2H, m), 1.81 (3H, s).

B. 2-Bromobenzoyl Chloride

2-Bromobenzoyl chloride is prepared as described for 4-trifluoromethyl-2-biphenyl-carboxylic acid chloride (the title D compound of Example 1) and used as is without purification.

C. N-(2-Acetylamino-indan-5-yl)-2-bromobenzamide

The title compound is prepared as described for {5-[(4'-trifluoromethylbiphenyl-2-carbonyl)-amino]-indan-2-yl}-carbamic acid tert-butyl ester (the title E compound of Example 1) using N-(5-amino-indan-2-yl)-acetamide (the title A compound; 1.05 g, 5.50 mmol) and 2-bromo-benzoyl chloride (the title B compound; 1.21 g, 5.50 mmol) to give the product, mp 216–217° C. MS (ES+), m/z 373 (M+H), 375 (M+H).

D. To a solution of N-(2-acetylamino-indan-5-yl)-2-bromo-benzamide (the title C compound; 0.150 g, 0.40 mmol) and 4-fluorobenzeneboronic acid (0.0.84 g, 0.60 mmol) in DME (7 mL) is added $PdCl_2(dppf)$ (0.010 g, 0.012 mmol) followed by $K_3PO_4$ (0.25 g, 1.20 mmol). The reaction mixture is degassed and heated at reflux under $N_2$ atmosphere for 16 h. After cooling to room temperature, the reaction mixture is diluted with water and extracted with ethyl acetate. The organic layer is dried ($MgSO_4$) and concentrated under reduced pressure to give a tan solid. Trituration with ethyl acetate gives 4'-fluorobiphenyl-2-carboxylic acid (2-acetylamino-indan-5-yl)-amide as a grey solid, mp 218–220° C. MS (ES+), m/z 389 (M+1).

EXAMPLE 4

The following compounds are prepared similarly to Examples 1 or 3.

5

| Compound | 1. Structure | MS [m/z] | MP (° C.) |
|---|---|---|---|
| (a) | *structure: 4-methoxybiphenyl-2-carboxamide of 2-acetamidoindan-5-yl* | 401 [M + 1] | 223–225 |
| (b) | *structure: 3,5-bis(trifluoromethyl)biphenyl-2-carboxamide of 2-acetamidoindan-5-yl* | 507 [M + 1] | 200–202 |
| (c) | *structure: 4-methylbiphenyl-2-carboxamide of 2-acetamidoindan-5-yl* | 385 [M + 1] | 105–108 |
| (d) | *structure: 4-chlorobiphenyl-2-carboxamide of 2-acetamidoindan-5-yl* | 405 [M + 1] | 222–224 |
| (e) | *structure: 4-(trifluoromethyl)biphenyl-2-carboxamide of indan-5-yl* | 382 [M + 1] | 211–212 |
| (f) | | 314 [M + 1] | |

EXAMPLE 5

5-Amino-2-(thiophen-2-yl)-N-(indan-5-yl)-benzamide

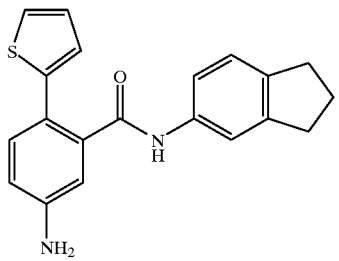

A. 2-Bromo-5-nitrobenzoyl chloride

To a solution of 2-bromo-5-nitrobenzoic acid (1.00 g, 4.06 mmol) in methylene chloride (15 mL) is added oxalyl chloride (1.42 mL, 16.24 mmol) followed by 1 drop DMF. Addition of DMF results in vigorous gas evolution. After 1.5 h, the reaction mixture is concentrated under reduced pressure to give an oil which is used as is without purification.

B. 2-Bromo-N-(indan-5-yl)-5-nitro-benzamide

2-Bromo-N-indan-5-yl-5-nitro-benzamide is prepared similarly to the title E compound of Example 1 using the title A compound, 2-bromo-5-nitrobenzoyl chloride (1.07 g, 4.06 mmol) and 5-aminoindan (0.54 g, 4.06 mmol). $^1$H NMR (DMSO-d$_6$, 300 MHz): δ 10.52 (1H, s), 8.34 (1H, d), 8.21 (1H, dd), 8.03 (1H, d), 7.60 (1H, s), 7.38 (1H, d), 7.19 (1H, d), 2.85 (4H, m), 2.02 (2H, m).

C. N-(Indan-5-yl)-5-nitro-2-(thiophen-2-yl)-benzamide

N-(Indan-5-yl)-5-nitro-2-(thiophen-2-yl)-benzamide is prepared similarly to the title compound of Example 3 using the title B compound, 2-bromo-N-(indan-5-yl)-5-nitro-benzamide (0.137 g, 0.380 mmol) and 2-thiopheneboronic acid (0.073 9, 0.570 mmol). $^1$H NMR (DMSO-d$_6$, 300 MHz): δ 10.59 (1H, s), 8.38 (1H, dd), 8.30 (1H, d), 7.81 (1H, d), 7.73 (1H, d), 7.06 (1H, s), 7.46 (1H, d), 7.30 (1H, d), 7.18 (2H, m), 2.83 (4H, q), 2.01 (2H, m).

D. 5-Amino-2-(thiophen-2-yl)-(N-indan-5-yl)-benzamide

A solution of the compound of Example 5, N-(indan-5-yl)-5-nitro-2-thiophen-2-yl-benzamide (0.083 g, 0.228 mmol) in ethyl acetate (10 mL) is degassed and 10% palladium on carbon added. The reaction mixture is evacuated and placed under 1 atm H$_2$(g) for 16 h. Filtration of the reaction mixture through Celite is followed by concentration of the filtrate under reduced pressure to give 5-amino-N-(indan-5-yl)-2-(thiophen-2-yl)-benzamide as an oil which foams to a solid on treatment with diethyl ether. mp 62–67° C. MS (ES+), m/z 335 (M+1).

EXAMPLE 6

The following compounds are prepared similarly to the compound of Example 5 by reduction of the corresponding nitro compounds.

| Compound | 2. Structure | MS [m/z] | MP (° C.) |
|---|---|---|---|
| (a) | | 329 [M + 1] | 160–162 |
| (b) | | 397 [M + 1] | 149–150 |

EXAMPLE 7

N-(Indan-5-yl)-2-(4-trifluoromethyl-phenyl)-nicotinamide hydrochloride

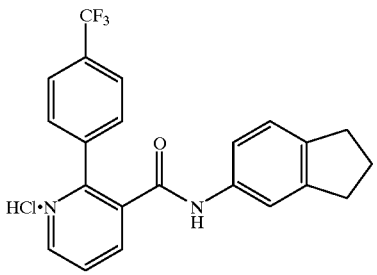

A. 2-Chloronicotinic acid methyl ester

To a solution of 2-chloronicotinic acid (2.00 g, 12.69 mmol) in DMF (40 mL) at 0° C. is added cesium carbonate (4.96 g, 15.23 mmol) followed by iodomethane (0.95 mL, 15.23 mmol). The reaction mixture is warmed to room temperature and stirred 16 h. Dilution with ethyl acetate is followed by washing with water, 8% NaHCO$_3$ solution and brine. The organic layer is dried (MgSO$_4$) and concentrated under reduced pressure to give 2-chloronicotinic acid methyl ester as an oil: $^1$H NMR (CDCl$_3$, 300 MHz): δ 8.55 (1H, dd), 8.18 (1H, dd), 7.33 (1H, dd), 3.97 (3H, s).

B. 2-(4-Trifluoromethyl-phenyl)-nicotinic acid methyl ester 2-(4-Trifluoromethyl-phenyl)-nicotinic acid methyl ester is prepared similarly to the title compound of Example 3 using 2-chloronicotinic acid methyl ester (1.45 g, 8.45 mmol) and 4-trifluoromethylbenzeneboronic acid (2.41 g, 12.68 mmol) to give the product as an oil: $^1$H NMR (CDCl$_3$, 300 MHz): δ 8.80 (1H, dd), 8.19 (1H, dd), 7.67 (4H, q), 7.40 (1H, dd), 3.70 (3H, s). MS (ES+) m/z 282 (M+1).

C. 2-(4-Trifluoromethyl-phenyl)-nicotinoyl chloride

To a solution of the title B compound, 2-(4-trifluoromethyl-phenyl)-nicotinic acid methyl ester (0.626 g, 2.228 mmol) in 1:1 THF:H$_2$O (10 mL) is added LiOH.H$_2$O (0.187 g, 4.456 mmol). After 3.5 h, the reaction mixture is concentrated to dryness under reduced pressure. To a slurry of the crude lithium salt in methylene chloride (10 mL) is added oxalyl chloride (0.78 mL, 8.91 mmol) followed by a few drops DMF. After stirring 16 h, the reaction mixture is concentrated to dryness under reduced pressure and used as is without purification.

D. N-(Indan-5-yl)-2-(4-trifluoromethyl-phenyl)-nicotinamide hydrochloride

The title compound is prepared in a manner similar to that described for the title E compound of Example 1 using 2-(4-trifluoromethyl-phenyl)-nicotinoyl chloride (2.228 mmol) and 5-aminoindan (0.296 g, 2.228 mmol) to give the product as the free base. The hydrochloride salt is prepared by bubbling HCl(g) through an ethyl acetate solution of the free base and trituation of the salt with diethyl ether; mp 190–205° C. MS (ES+) m/z 383 (M+1).

EXAMPLE 8

The following compounds are prepared similarly to the compound of Example 7.

| Compound | 3. Structure | MS [m/z] | MP (° C.) |
|---|---|---|---|
| (a) | | 505 [M + 1] | 110–125 |

-continued

| Compound | 3. Structure | MS [m/z] | MP (° C.) |
|---|---|---|---|
| (b) | | 536 [M + 1] | 189–192 |
| (c) | | 440 [M + 1] | 208–211 |
| (d) | | 484 [M + 1] | 105–123 |
| (e) | | 583 [M + 1] | 115–118 |
| (f) | | 539 [M + 1] | foam |

EXAMPLE 9

The following compounds are prepared by the method of Abdel-Magid, A. F. et al (J. Org. Chem. 1996, 61, 3849) using the title F compound of Example 1 (4'-Trifluoromethyl-biphenyl-2-carboxylic acid (2-amino-indan-5-yl)-amide hydrochloride) and the appropriate aldehyde.

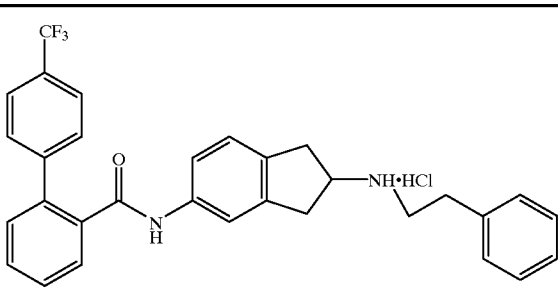

| Example 4. Structure | MS [m/z] | MP (° C.) |
|---|---|---|
| (a) | 501 [M + 1] | 220 dec |
| (b) | 487 [M + 1] | 179–183 |

EXAMPLE 10

N-[2-(N-methyl-N-methanesulfonylamino)-indan-5-yl]-2-4'-trifluoromethybiphenyl-2-carboxamide

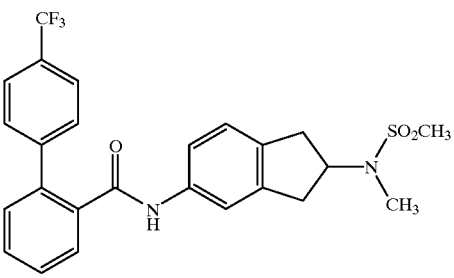

A. N-Methyl-2-aminoindane

Under a nitrogen atmosphere, a solution of the carbamate 2-(ethoxycarbonyl-amino)indane (6.07 g, 29.6 mmol) in $Et_2O$ (100 mL) is added slowly to a mixture of $LiAlH_4$ (1.70 g, 44.7 mmol) in $Et_2O$ (100 ml) chilled at 0°. The resulting mixture is stirred for 18 h and allowed to warm to 20°. The reaction mixture is re-chilled to 0° and treated cautiously with $H_2O$ (1.7 mL), 15% NaOH (1.7 mL) and again $H_2O$ (5.1 mL). The mixture is stirred for 20 minutes, warming slowly to 20°. The precipitate is vacuum filtered and the filtrate extracted into 1N HCl. The acid solution is washed with fresh $Et_2O$, then basified with cold 1N NaOH. The cloudy mixture is extracted with $Et_2O$, washed with saturated brine, dried over $Na_2SO_4$, is filtered and concentrated to an oil.

B. N-(Indan-2-yl)-N-methyl-methanesulfonamide

Under a nitrogen atmosphere, a solution of methanesulfonyl chloride (1.08 g, 9.5 mmol) in $CH_2Cl_2$ (10 mL) is added slowly to a solution of the title A compound (1.35 g, 9.2 mmol) and ethyldiisopropylamine (4.75 g, 36.8 mmol) in $CH_2Cl_2$ (50 mL) and stirred at 20° for 18 hr. The reaction mixture is concentrated to dryness and the residue is re-dissolved into $Et_2O$. The solution is washed sequentially with 8% $NaHCO_3$, $H_2O$ 1N HCl, $H_2O$ and finally saturated brine, and is dried over $Na_2SO_4$, filtered and concentrated to dryness to yield the product.

C. N-(-5-Nitro-indan-2-yl)-N-methyl-methanesulfonamide

Fuming $HNO_3$ (2.0 mL, 50.4 mmol) is added very slowly to a solution of the title B compound (1.80 g, 8.0 mmol) in TFA (25 ml) chilled at 0°. The reaction mixture is stirred at 0° for 3 hr., then the solvent evaporated at 20°. The residue is treated with ice and extracted into EtOAc. The EtOAc solution is washed with 8% $NaHCO_3$, $H_2O$ and saturated brine and then dried over $Na_2SO_4$. The solution is filtered and the solvent evaporated to yield a solid product which is recrystalized from cold EtOAc.

D. N-(5-Amino-indan-2-yl)-N-methyl-methanesulfonamide

A mixture of the title C compound (1.10 g, 4.1 mmol) and 10% palladium on carbon (0.11 g) are in EtOAc (50 mL) is stirred under hydrogen (1 atmosphere) at 20° for 3 hr. The catalyst is filtered off and the filtrate concentrated to yield the title product as a solid.

E. N-[2-(N-methyl-N-methanesulfonylamino)-indan-5-yl]-2-(4'-trifluoromethylbiphenyl-2-carboxamide Under a nitrogen atmosphere, a solution of 4'-trifluoromethyl-2-biphenylcarboxylic acid chloride (0.23 g, 0.80 mmol) in $CH_2Cl_2$ (5 mL) is slowly added to a solution of the title D compound (0.18 g, 0.74 mmol) and ethyldiisopropyl amine (0.38 g, 2.94 mmol) in $CH_2Cl_2$ (10 mL). The mixture is stirred at room temperature for 18 hrs, concentrated in vacuo and the residue is dissolved into EtOAc. The solution is washed with 8% NaHCO₃ (twice), then with water, and then with 1N HCl, and then with saturated brine solution, and dried over Na₂SO₄. The solution is filtered and concentrated to dryness in vacuo. The residue is dried to yield the title product, mp 163–165°.

EXAMPLE 11

Prepared similarly to Example 10, is N-[2-(N-methyl-N-acetylamino)indan-5-yl]-2-4'-trifluoromethylbiphenyl-2-carboxamide of the formula

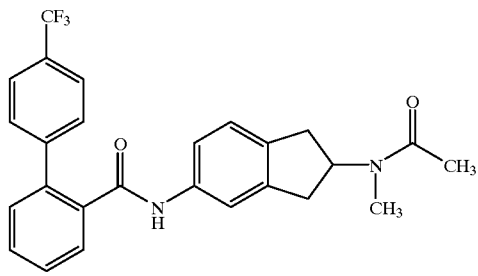

mp 195–198°; MS: 453 (M+1).

EXAMPLE 12

(a) (S)-4'-Trifluoromethylbiphenyl-2-carboxylic acid (2-methoxycarbonylamino-indan-5-yl)-amide

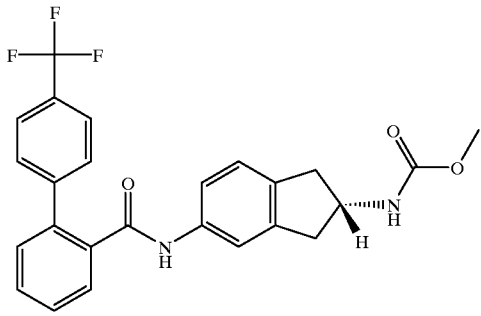

A. The alcohol, (1-hydroxy-indan-2-yl)-carbamic acid methyl ester (1S-trans) prepared from L-phenylalanine (18.7 g, 0.09 mol) (J. Org. Chem. 1983, 48, 2675–2679) is suspended in methylene chloride and cooled to 0° C. Pyridine (10.7 g, 0.135 mol) is added followed by acetyl chloride (10.5 g, 0.135 mol). The mixture is stirred for 1 h. and then washed with sodium bicarbonate, 1N HCl and saturated sodium chloride. The organic layer is dried over Na₂SO₄, filtered and evaporated under reduced pressure to give (1-acetyloxy-indan-2-yl)-carbamic acid methyl ester (1S-trans).

B. To 90% HNO₃ (55.1 g, 0.8 mol) under nitrogen at −30° C. is added 100 mL of trifluoroacetic acid followed by the addition of trifluoroacetic anhydride (100 g, 0.476 mol) over 5 minutes. The above carbamate (1-acetyloxy-indan-2-yl)-carbamic acid methyl ester (1S-trans)) (20.0 g, 0.08 mol) in 34 mL of methylene chloride is added slowly (over 90 min.) keeping the temperature between −30 and −35° C. The reaction is worked up by adding 100 mL of water and warmed to 0° C. to give two layers. The layers are separated and the aqueous layer extracted with methylene chloride. The combined organic extracts are washed with 100 mL of water (pH is adjusted to 8.5 with sodium bicarbonate), and with cold water. The organic layer is dried over MgSO4, filtered and evaporated to give crude product. The crude product is crystallized from ethyl acetate and further precipitated by the addition of heptane to give (1-acetyloxy-6-nitro-indan-2-yl)-carbamic acid methyl ester (1S-trans); mp 164–167° C.

C. The above acetate (16.5 g, 0.056 mol) is suspended in 275 mL of methanol at room temperature. 1N Sodium hydroxide solution (112 mL, 0.112 mol) is added and the mixture is stirred at room temperature for 15 minutes. The reaction is diluted with water and the solid is collected. The solid is reslurried in 250 mL of ice-water and pH is adjusted to 6.5–7.0 with 1N HCl. The solution is filtered and washed with water, and the product is collected and dried under vacuum to give (1-hydroxy-6-nitro-indan-2-yl)-carbamic acid methyl ester (1S-trans); mp 201–203° C.

D. The above nitro alcohol (6.0 g, 0.023 mol) is dissolved in 300 mL of acetic acid containing 3 mL of water at 50° C. The mixture is cooled to room temperature and HClO₄ (6 g, 0.042 mol) and 10% Pd/C (6 g) are added and the mixture is hydrogenated at 50 psi for two days. Fresh catalyst (3 g) is added twice during the reaction period. The reaction mixture is filtered through celite, the filtrate is concentrated and the residue is washed with ice-water, dried over MgSO4. The solution is filtered and solvent removed under reduced pressure to give (S)-(5-amino-indan-2-yl)-carbamic acid methyl ester; mp 140–142° C.

(R)-(5-aminoindan-2-yl)-carbamic acid methyl ester is similarly prepared from (1-acetyloxyindan-2-yl)-carbamic acid methyl ester (1R-trans), starting with D-phenylalanine instead of L-phenylalanine.

E. To a 0° C. solution of (S)-(5-aminoindan-2-yl)-carbamic acid methyl ester, (500 mg, 2.43 mmol) in 20 mL of methylene chloride and pyridine (0.236 mL, 2.9 mmol) is added 4'-trifluoromethyl-2-biphenylcarboxylic acid chloride (0.076 g, 2.6 mmol) in 5 mL of methylene chloride. The reaction is warmed to room temperature and stirred for 1 h. The mixture is washed with 1N HCl, sodium bicarbonate and brine. The organic layer is dried over MgSO4, filtered, concentrated, and chromatographed on silica gel eluting with ethyl acetate/hexanes (1:1) to give (S)-[5-[(4'-trifluoromethyl-biphenyl]-2-carbonyl)amino]-indan-2-yl]-carbamic acid methyl ester, the compound of example 13(d).

(b) (S)-4'-Trifluoromethylbiphenyl-2-carboxylic acid (2-benzenesulfonylamino-indan-5-yl)-amide

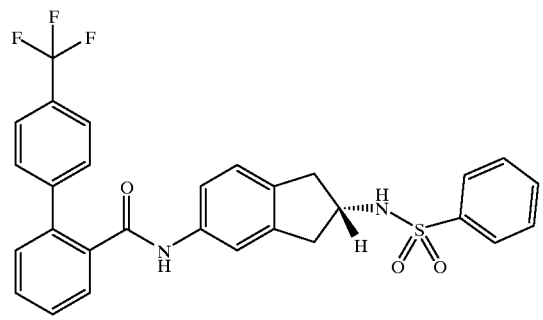

A. To a 0° C. solution of the carbamate of example 12(a) (0.96 g, 2.1 mmol) in 75 mL of acetonitrile is added trimethylsilyl iodide. The mixture is stirred for 16 h. The reaction is quenched with 2 mL of methanol and stirred for 1 h. The mixture is concentrated and the residue is redissolved in ethyl acetate. The solution is washed with sodium bicarbonate and saturated sodium chloride solution. The organic layer is dried over MgSO$_4$, filtered and concentrated under reduced pressure to give (S)-N-(2-aminoindan-5-yl)-4'-trifluoromethylbiphenyl-2-carboxamide.

B. (S)-4'-Trifluoromethylbiphenyl-2-carboxylic acid (2-benzenesulfonylaminoindan-5-yl)-amide is prepared from the amine as described in Example 1, mp 152–153° C.; [a]$_D$ –7.304 (c=10.152 mg/mL, methanol).

EXAMPLE 13

Prepared similarly to Example 12 from either (1S-trans)- or (1R-trans)-(1-acetyloxy indan-2-yl) carbamic acid methyl ester are the following compounds.

| Compound | Structure | Enantiomer | MS [m/z] | MP (° C.) |
|---|---|---|---|---|
| (a) | 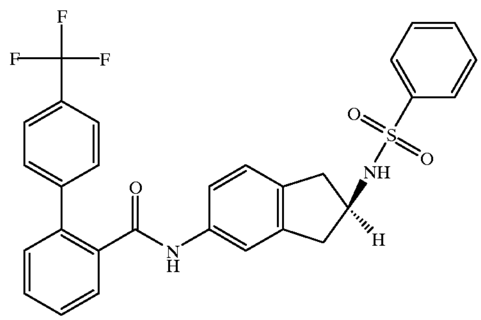 | (R) | 537 [M + 1] | 152–153 |
| (b) | 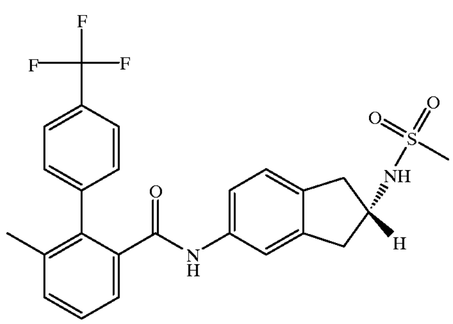 | (S) | 489 [M + 1] | 95–110 |
| (c) | 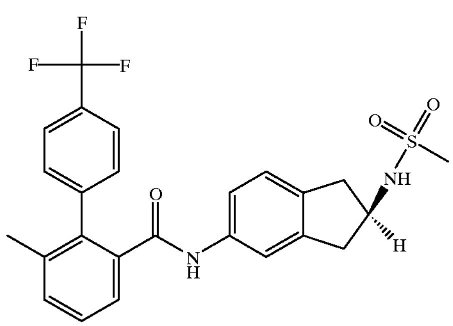 | (R) | 489 [M + 1] | 95–110 |
| (d) | 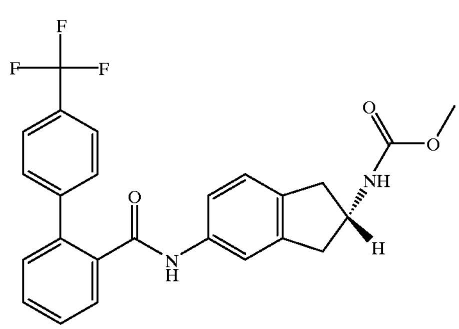 | (S) | 455 [M + 1] | 172–174 |

-continued
| Compound | Structure | Enantiomer | MS [m/z] | MP (° C.) |
|---|---|---|---|---|
| (e) | 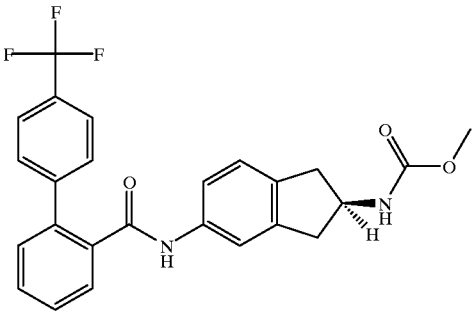 | (R) | 455 [M + 1] | 168–173 |
| (f) | 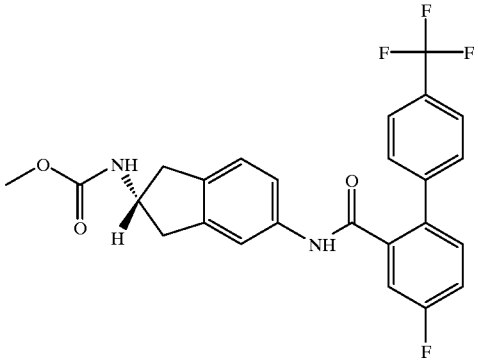 | (R) | 490 [M + 1] | 190–196 |
| (g) | 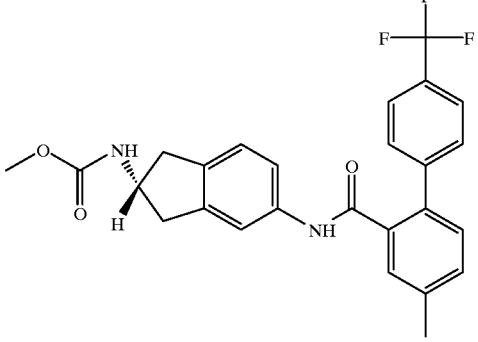 | (R) | 486 [M + 1] | 218–221 |
| (h) | 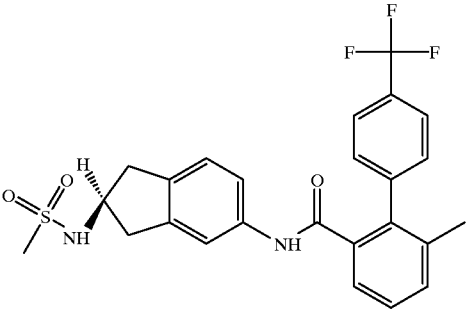 | (S) | 489 [M + 1] | 191–194 |

-continued

| Compound | Structure | Enantiomer | MS [m/z] | MP (° C.) |
|---|---|---|---|---|
| (i) | 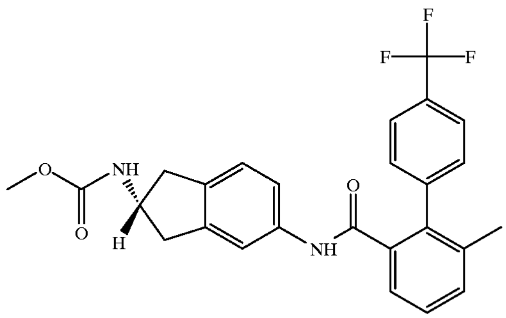 | (R) | 469 [M + 1] | 95–100 |
| (j) | 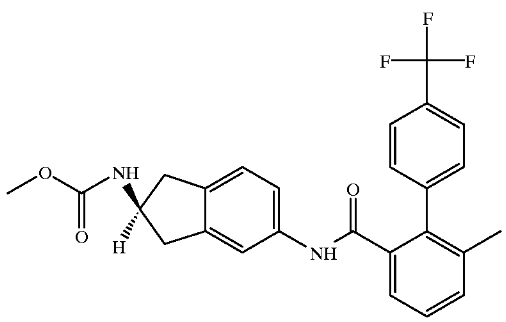 | (S) | 469 [M + 1] | 85–88 |
| (k) | 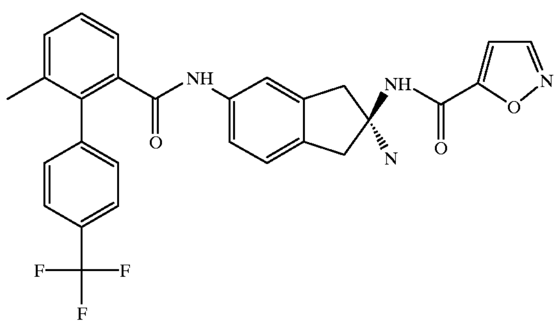 | (S) | 506 [M + 1] | 108–115 |
| (l) | 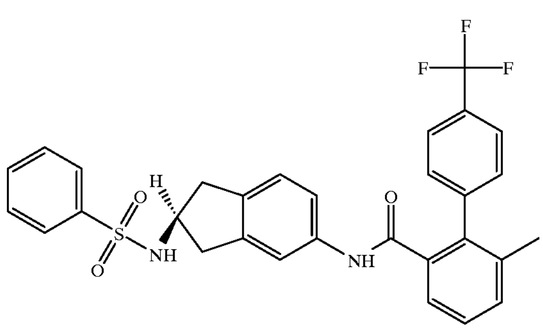 | (S) | 568 [M + NH$_4^+$] | 97–120 |

-continued

| Compound | Structure | Enantiomer | MS [m/z] | MP (° C.) |
|---|---|---|---|---|
| (m) | 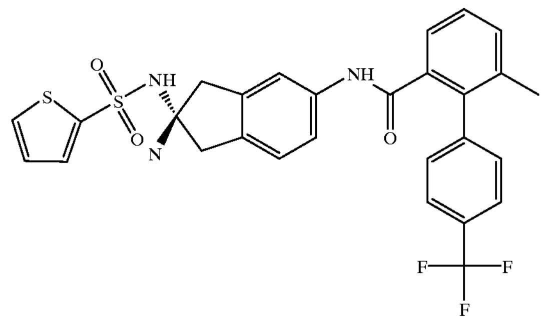 | (S) | 557 [M + 1] | 105–140 |
| (n) | 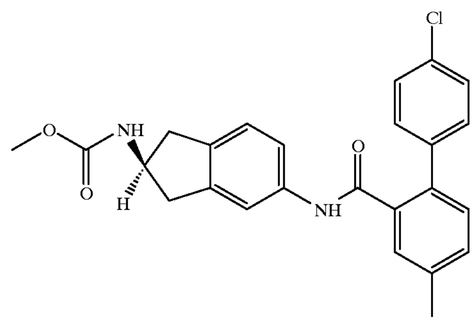 | (S) | 435 [M + 1] | 238–239 |
| (o) | 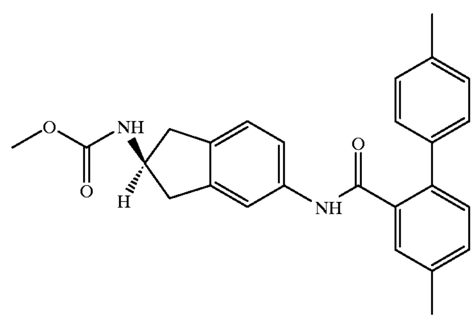 | (S) | 414 [M + 1] | 233–236 |
| (p) | 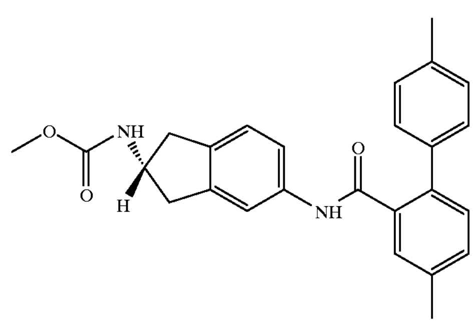 | (R) | 415 [M + 1] | 236–239 |

-continued

| Compound | Structure | Enantiomer | MS [m/z] | MP (° C.) |
|---|---|---|---|---|
| (q) | 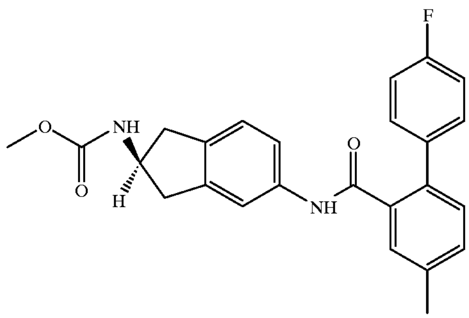 | (S) | 419 [M + 1] | 189–191 |
| (r) | 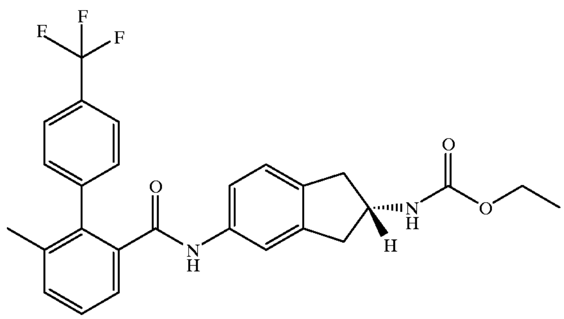 | (S) | 483 [M + 1] | 190–115 |
| (s) | 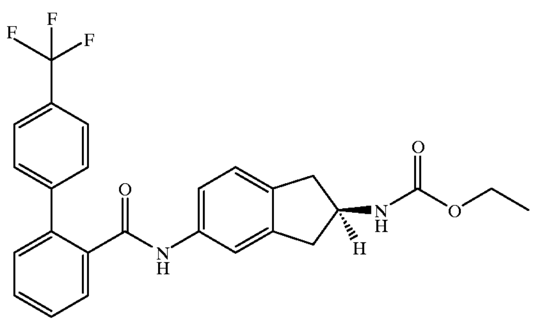 | (R) | 483 [M + 1] | 90–110 |
| (t) | 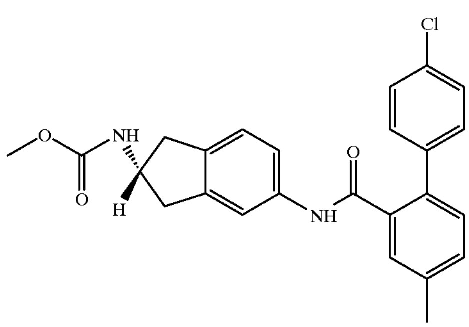 | (R) | 435 [M + 1] | 237–239 |

-continued

| Compound | Structure | Enantiomer | MS [m/z] | MP (° C.) |
|---|---|---|---|---|
| (u) | 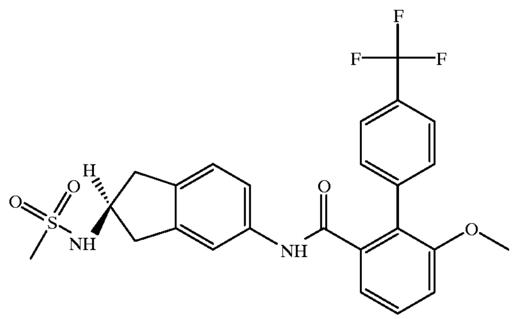 | (S) | 505 [M + 1] | 157–158 |
| (v) | 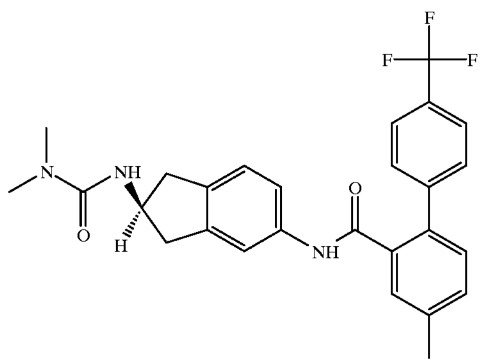 | (S) | 482 [M + 1] | 249–252 |
| (w) | 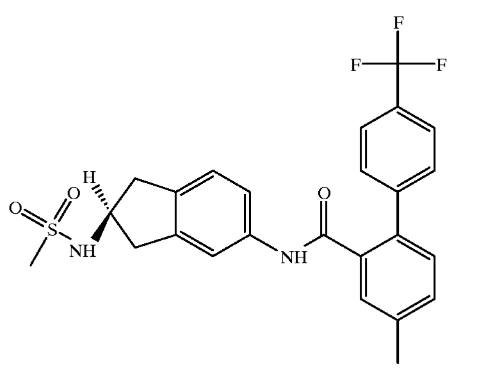 | (S) | 489 [M + 1] | 187–198 |
| (x) | 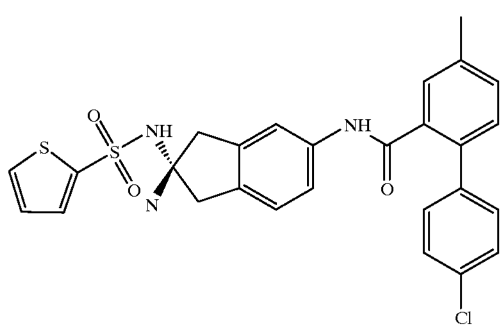 | (S) | 524 [M + 1] | 90–95 |

-continued
| Compound | Structure | Enantiomer | MS [m/z] | MP (° C.) |
|---|---|---|---|---|
| (y) | 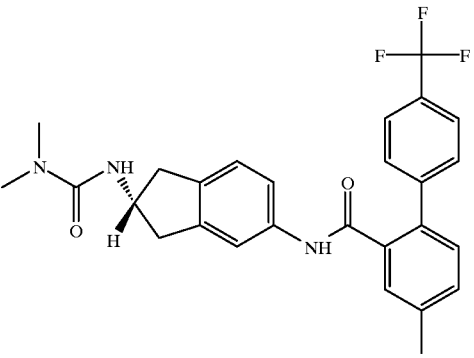 | (R) | 482 [M + 1] | 256–259 |
| (z) | 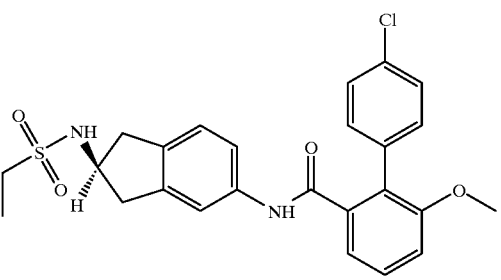 | (S) | 502 [M + NH₄] | 220–223 |
| (aa) | 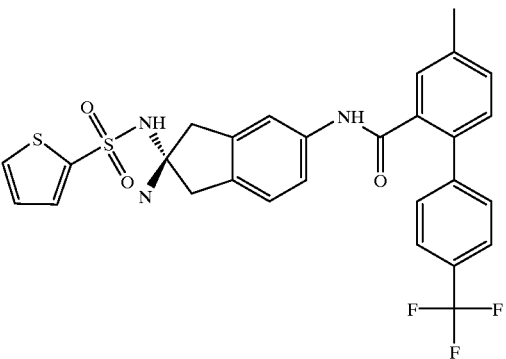 | (S) | 574 [M + NH₄⁺] | 168–169 |
| (ab) | 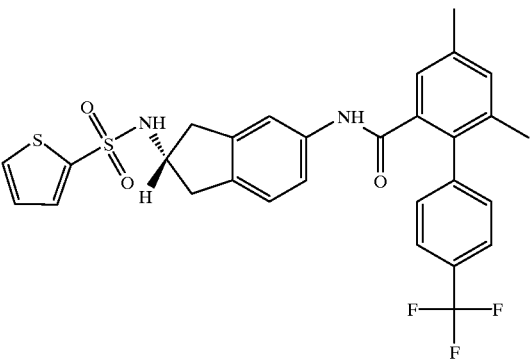 | (S) | 588 [M + NH₄⁺] | 157–158 |

-continued

| Compound | Structure | Enantiomer | MS [m/z] | MP (° C.) |
|---|---|---|---|---|
| (ac) | 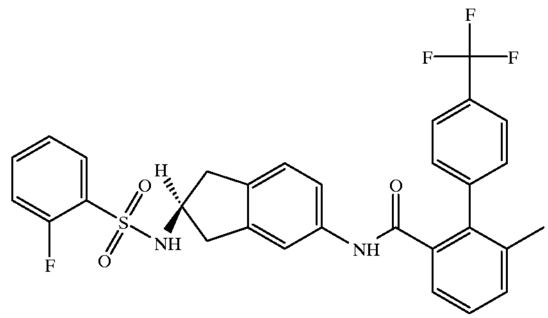 | (S) | 569 [M + 1] 586 [M + NH₄] | 97–101 |
| (ad) | 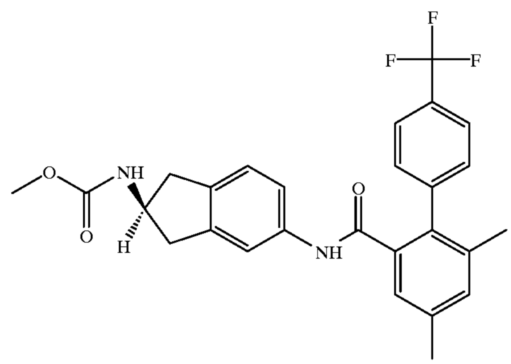 | (S) | 483 [M + 1] | 147–148 |
| (ae) | 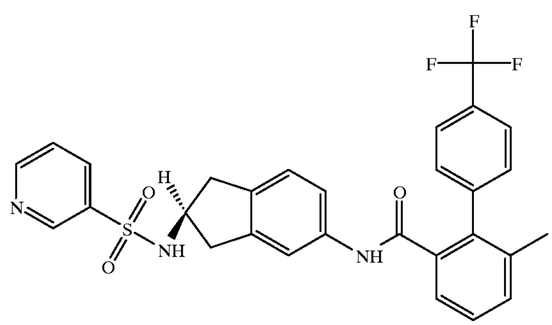 | (S) | 552 [M + 1] | 80 (dec.) |
| (af) | 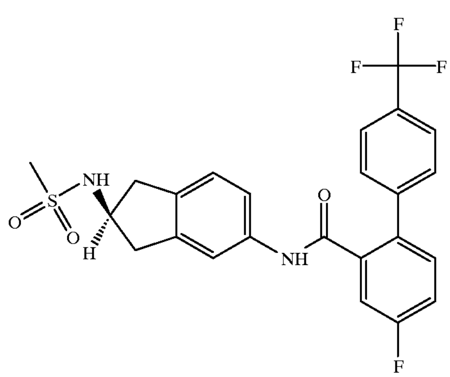 | (S) | 493 [M + 1] 510 [M + NH₄⁺] | 179–181 |

-continued
| Compound | Structure | Enantiomer | MS [m/z] | MP (° C.) |
|---|---|---|---|---|
| (ag) | 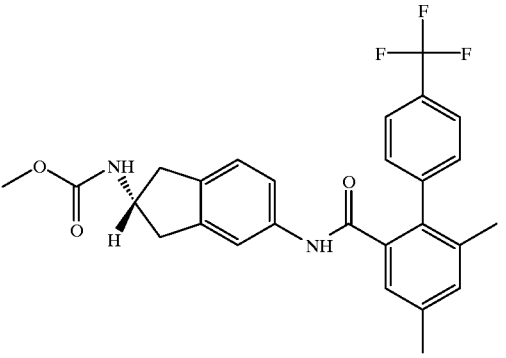 | (R) | 483 [M + 1] | 144–145 |
| (ah) | 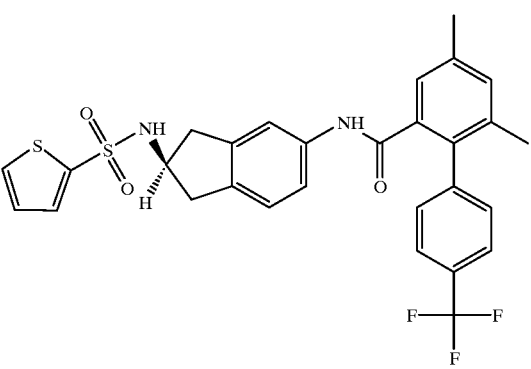 | (R) | 588 [M + NH₄⁺] | 161–162 |
| (ai) | 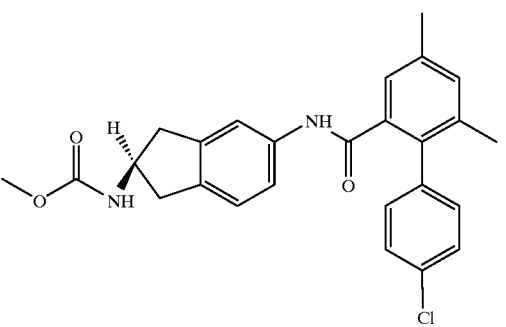 | (R) | 449 [M + 1] | 140–141 |
| (aj) | 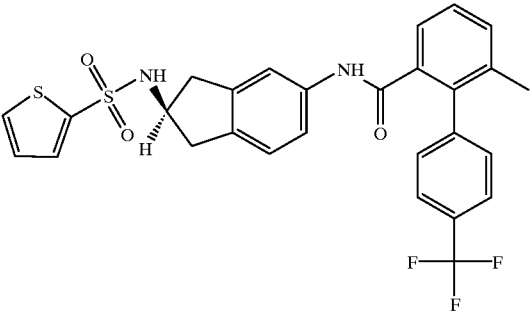 | (R) | 557 [M + 1] 574 [M + NH₄⁺] | 100–107 |

| Compound | Structure | Enantiomer | MS [m/z] | MP (° C.) |
|---|---|---|---|---|
| (ak) | 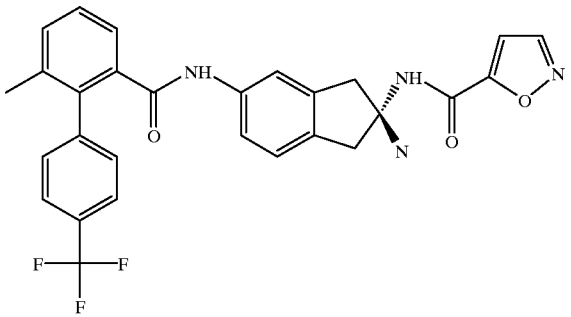 | (R) | 506 [M + 1] 523 [M + NH$_4^+$] | 113–120 |
| (al) | 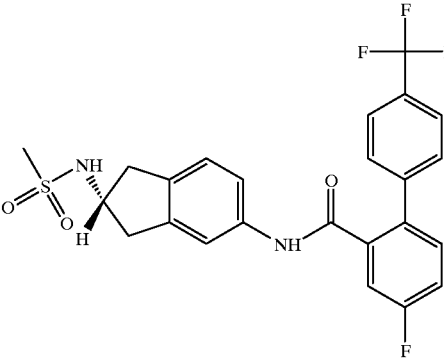 | (R) | 493 [M + 1] 511 [M + NH$_4^+$] | 181–183 |
| (am) | 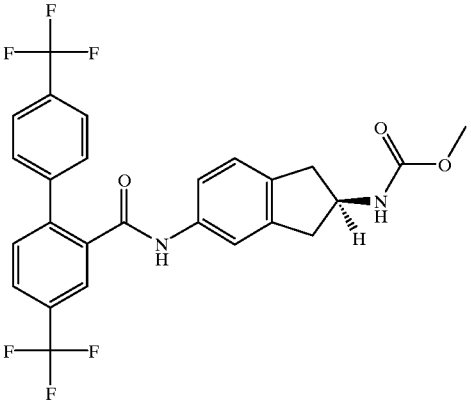 | (R) | 523 [M + 1] | 199–200 |
| (an) | 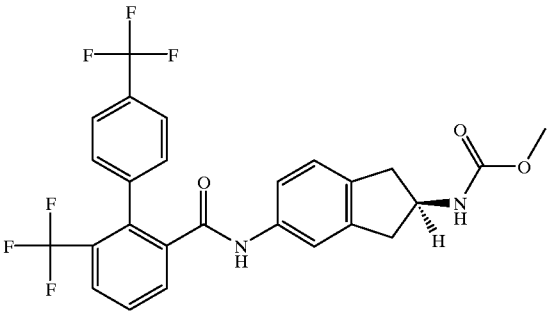 | (R) | 523 [M + 1] | 203–205 |

EXAMPLE 14

(R)-6-Methyl-4'-trifluoromethylbiphenyl-2-carboxylic acid (2-methoxycarbonylamino-indan-5-yl)-amide

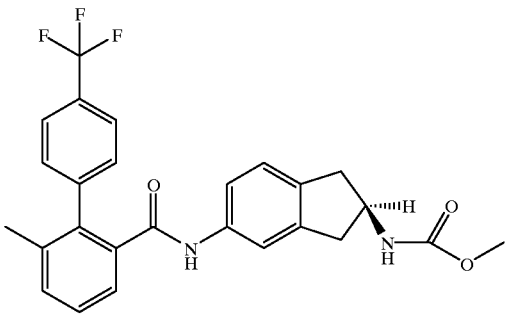

A. A solution of 2-bromo-3-methyl-benzoic acid (21.5 g, 100 mmol) in 500 mL of methanol and 8 mL of concentrated sulfuric acid is refluxed overnight. Methanol is removed under reduced pressure, the residue is taken up in ether, washed with sodium bicarbonate, brine, and dried over magnesium sulfate, filtered, and evaporated under reduced pressure to give methyl 2-bromo-3-methylbenzoate as an oil.

B. A mixture of methyl 2-bromo-3-methylbenzoate (22.33 g, 97.5 mmol), potassium phosphate (82.8 g, 390 mmol), [1,1'-bis(diphenylphosphino)-ferrocene]dichloro palladium (II), complex with dichloromethane (1:1) (3.98 g, 4.87 mmol), and p-trifluoromethylphenylboronic acid (22.2 g, 117 mmol) in 500 mL of DME is degassed and refluxed under an atmosphere of argon overnight. The mixture is concentrated, poured into water and extracted with ethyl acetate. The combined organic extracts are washed with brine, dried over magnesium sulphate, filtered and evaporated under reduced pressure. The residue is purified by silica gel chromatography eluting with ethyl acetate/toluene (1:9) to give methyl 6-methyl-4'-trifluoromethyl-biphenyl-2-carboxylate.

C. A mixture of methyl 6-methyl-4'-trifluoromethyl-biphenyl-2-carboxylate (13.6 g, 46.3 mmol), and 1N NaOH (92.5 mL, 92.5 mmol) in 225 mL of ethanol is refluxed for 5 h. Water is added to the mixture and the aqueous layer is washed with ether. The aqueous layer is acidified with 1N HCl and extracted with ethyl acetate, dried over magnesium sulfate, filtered, and concentrated under reduced pressure. The product is purified by crystallization from ethyl acetate/hexanes to yield 6-methyl-4'-trifluoromethyl-biphenyl-2-carboxylic acid melting at 202–203° C. MS m/z 279 (M−1).

D. To a ice bath cooled suspension of 6-methyl-4'-trifluoromethyl-biphenyl-2-carboxylic acid (17.7 9, 63.2 mmol) in 500 mL of methylene chloride is added oxalyl chloride (22.1 mL, 253 mmol) followed by 4 drops of DMF. The reaction is stirred for 2 h and another 22 mL of oxalyl chloride and 4 drops of DMF is added. Stirring is continued another 2 h. The mixture is concentrated under reduced pressure. Methylene chloride (100 mL) is added and the acid chloride is used as is in subsequent reactions.

E. To an ice bath cooled solution of (R)-(5-aminoindan-2-yl)-carbamic acid methyl ester (9.5 g, 46.1 mmol) prepared as described in example 12 ($[\alpha]_D$=−26.29 (c=9.87 mg/mL, DMSO); mp 144–145° C.) and pyridine (4.48 mL, 55.5 mmol) in 200 mL of methylene chloride is added 6-methyl-4'-trifluoromethyl-biphenyl-2-carboxylic acid chloride (80.5 mL of a 0.63 M solution in methylene chloride, 50.7 mmol). The reaction is stirred for 15 minutes at room temperature. The mixture is washed with 1N HCl, bicarbonate and brine. The organic layer is dried over magnesium sulfate, filtered, and concentrated under reduced pressure. The product is purified by crystallization from ethyl acetate/hexanes (1:2) to give (R)-6-methyl-4'-trifluoromethylbiphenyl-2-carboxylic acid (2-methoxycarbonylaminoindan-5-yl)-amide (the compound of example 13(i)) as a crystalline solid, mp 112–114° C. MS (ES+), m/z469 (M+1); $[\alpha]_D$=−12.85° (c=11.36 mg/ml DMSO).

Alternatively, steps D and E can be carried out as follows:

A solution of 2.5 g of 6-methyl-4'-trifluoromethyl-biphenyl-2-carboxylic acid in 8 mL of tetrahydrofuran is added to a solution of 1.2 g of oxalyl chloride and 0.06 g of dimethylformaide in 16 mL of tetrahydrofuran at 0–5° C. over 20 minutes and the temperature is maintained at 0–5° C. for 1 hour to obtain a solution of the acid chloride.

To a solution of 1.6 g of (R)-(5-aminoindan-2-yl)-carbonic acid methyl ester in 32 mL of tetrahydrofuran cooled to 0 to 5° C. is added 3.2 g of triethylamine.

The above acid chloride solution is then added over about 25 minutes at a temperature below 8° C. The reaction mixture is warmed to 0–5° C. and stirred for 2 hours.

The solvent is exchanged to ethyl acetate by concentrating to a volume of 20 mL at ca. 70 mbar/40° C., adding 40 mL of ethyl acetate, concentrating to a volume of 30 mL and adding a further 20 mL of ethyl acetate.

The ethyl acetate solution is sequentially washed with 20 mL of water, 10 mL of 2N HCl, 3×15 mL of 5% sodium tetraborate decahydrate and 20 mL of water, and then evaporated to dryness. The crude foam is then crystallized from ethyl acetate/heptane to yield product described for Step E.

EXAMPLE 15

6-Methyl-4'trifluoromethylbiphenyl-2-carboxylic acid (7-methoxycarbonylamino-6,7,8,9-tetrahydro-5H-benzocyclohepten-2-yl)-amide

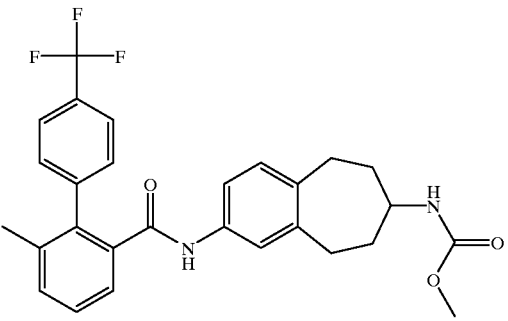

A. To 6,7,8,9-tetrahydro-5H-benzocyclohepten-7-one (2.56 g, 16 mmol) and hydroxylamine hydrochloride (2.2 g, 32 mmol) in 27 mL of water is slowly added a solution of sodium carbonate (1.69 g, 16 mmol) in 14 mL of water. The mixture is stirred overnight. The solid is then filtered off, washed with water, and dried at 50° C. under reduced pressure to give 6,7,8,9-tetrahydro-N-hydroxy-5H-benzocyclohepten-7-amine as a white solid.

B. To a suspension of $NaBH_4$ (1.98 g, 52.3 mmol) in 40 mL of DME cooled in an ice-bath is added $TiCl_4$. To this mixture is added title compound A (2.3 g, 13.1 mmol) in 28 mL of DME dropwise. The mixture is stirred overnight, poured into ice water (135 mL), basified with 28% ammonia (20 mL) and extracted with ethyl acetate. The organic extracts are dried over magnesium sulfate, filtered and concentrated under reduced pressure to give 6,7,8,9-tetrahydro-5H-benzocyclohepten-7-amine as an oil.

C. The compound from step B is treated with methyl chloroformate, nitrated, reduced, and acylated with 6-methyl-4'-trifluoromethylbiphenyl-2-carboxylic acid chloride according to procedure described in example 12 to give the title compound; m.p. 190–193° C.

EXAMPLE 16

The compound of example 15 is treated with trimethylsilyl iodide and the resulting amine is then reacted with the appropriate N-derivatizing agent (as described in previous examples) to yield the following compounds of the formula

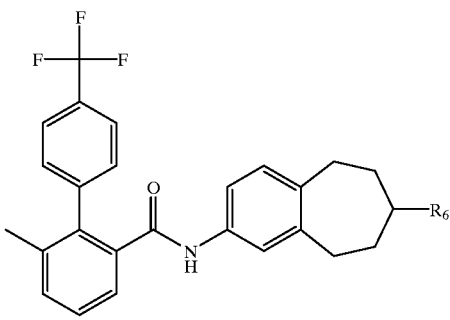

| Compound | $R_6$ | MP(° C.) |
|---|---|---|
| (1) | $CH_3SO_2NH-$ | 131–134° |
| (2) | $C_6H_5OCONH-$ | 242–244° |
| (3) | $o-FC_6H_4-SO_2NH-$ | 211–213° |

EXAMPLE 17

(R)-(5-Aminoindan-2-yl)-carbamic acid methyl ester

A mixture of ninhydrin (33 g, 0.185 mol) and acetic acid (554 g) is stirrred at rt under $N_2$ until complete dissolution of ninhydrin. Sulfuric acid is then added (54.42 g, 0.555 mol) followed by hydroxylamine sulfate (31.63 g, 0.193 mol). The mixture is heated to 55° C. for 30 minutes and is then allowed to cool to room temperature. 10% Pd/C (2.64 g, 8% w/w) is added to the resulting yellow suspension and the mixture is hydrogenated at a pressure of $H_2$ of 20 psi. After stirring for 1 hour at rt, the $H_2$ pressure is increased to 40 psi and the temperature increased to 35° C. After stirring for 8 hours, the reaction is allowed to cool before filtration on a pad of Celite (20 g). The Celite cake is washed with acetic acid (70 g). The filtrate is concentrated, xylene (250 g) is added to the resulting slurry and the mixture concentrated again. Xylene (170 g) is added followed by slow addition of 20% NaOH (367 g) until a basic pH and a clear separation of the organic and aqueous layers is obtained. The xylene layer is then separated and filtered. The HCl salt is then precipitated out by slow addition of a 4 N HCl solution in 1-pentanol (51 g). The suspension is cooled to 0° C. and filtered. The cake is rinsed with heptane (100 g) and dried under vacuum to yield 2-aminoindane hydrochloride as a white powder.

A solution of 118.8 g of 2-aminoindane hydrochloride in 594 mL of water is heated to a temperature of 58–60° C. and 120.0 g of bromine is added over a period of 50 minutes while maintaining an internal temperature at 58 to 62° C. The mixture is stirred at 60–62° C. for 1 hour and 107 mL of hydrobromic (48%) is added over a period of 5 minutes while maintaining the internal temperature of 60–62° C. The mixture is stirred for an additional 10 minutes. The reaction mixture is cooled to an internal temperature of 20–23° C. over a period of 1 hour. The resulting solid is collected by filtration, washed with 3×133 mL of 2-propanol and dried at 58–60° C. under vacuum (10–30 torr) to obtain crude (±)-5-bromo-2-aminoindan hydrobromide. A suspension of 156.0 g of crude (±)-5-bromo-2-aminoindane hydrobromide in 390 mL of deionized water is heated to a temperature at 95–100° C. to obtain a clear solution. The solution is cooled to an internal temperature at 20–23° C. over a period of 2.5 hours and stirred at 20–23° C. for an additional 30 minutes. The resulting solid is collected by filtration and washed with 3×20 mL of water (precooled to 0–5° C.), and dried at 60–65° C. under vacuum (10–30 torr) with nitrogen bleeding to obtain (±)-5-bromo-2-aminoindane hydrobromide. A mixture of 130.0 g of (±)-5-bromo-2-aminoindane hydrobromide and 1500 mL of isopropyl acetate is stirred at 20–25° C. under nitrogen. A solution (precooled to 20–25° C.) of 26.62 g of sodium hydroxide and 186.35 g of sodium chloride in 750 mL of water is added over a period of 5 minutes while maintaining an internal temperature at 20–25° C. The suspension is stirred efficiently until all the solid dissolves (30 minutes). The organic layer is separated and the aqueous layer is extracted with 750 mL of isopropyl acetate. The organic layers are combined to afford ~2330 mL of a solution of (±)-5-bromo-2-aminoindane free base.

To the above solution is added 1300 mL of isopropyl acetate and 930 mL of methanol. The solution is stirred under nitrogen and heated to an internal temperature of 65° C. to achieve a gentle refluxing, over a period of 15 minutes. A solution of 103.1 g of (1S)-(+)-10-camphorsulfonic acid in 660 mL of methanol is added over a period of 15 minutes while maintaining an internal temperature of 60–65° C. to obtain a clear solution followed by 185 mL of methanol to achieve a v/v ratio of isopropyl acetate: methanol of about 2:1. The reaction mixture is cooled to 20–23° C. over a period of 2 hours. The mixture is stirred at room temperature (20–23° C.) for an additional 2 hours. The solid is collected, washed with 500 mL of precooled (to 0–2° C.) mixture of isopropyl acetate and methanol (2:1; v/v) in two equal portions of 250 mL each, and dried at 50–55° C. (100 mm Hg) to obtain crude (R)-5-bromo-2-aminoindane (1S)-(+)-10-camphorsulfonate salt as a white solid. A mixture of 90.0 g of crude (R)-5-bromo-2-aminoindane (1S)-(+)-10-camphorsulfonate salt and 900 mL of methanol is heated to a temperature of 65° C. to achieve a gentle refluxing. This suspension is stirred at 65° C. for 1 hour and the reaction mixture is cooled to 20–23° C. over a period of 2 hours and stirred at 20–23° C. for an additional 2 hours. The resulting solid is collected, washed with 190 mL of precooled (to 0–2° C.) mixture of isopropyl acetate and methanol (1:1; v/v) in two equal protions of 95 mL each. The solid is dried at 50–55° C. (100 mm Hg) to obtain (R)-5-bromo-2-aminoindane (1S)-(+)-10-camphorsulfonate salt as a white solid (98.7% optical purity).

A suspension of 111.1 g of (R)-5-bromo-2-aminoindane (1S)-(+)-10-camphorsulfonate salt and 300 mL of isopropyl acetate is stirred at 20–25° C. and a solution of 15.0 g of sodium hydroxide and 75.0 g of sodium chloride in 300 mL of water is added over a period of 10 minutes while maintaining an internal temperature at 20 to 25° C. The suspension is stirred for 30 minutes or until all the solids dissolve. The organic layer is separated and the aqueous layer is extracted with 100 mL of isopropyl acetate. The organic layers containing (R)-5-bromo-2-aminoindane free base are combined. A solution of 60 g of sodium bicarbonate in 600 mL of water is added and the resulting white slurry is stirred under nitrogen and cooled to a temperature of 0–5° C. over a period of 15 minutes. A solution of 35.4 g of methyl chloroformate in 200 mL of isopropyl acetate is added over a period of 45 minutes while maintaining an internal temperature of 0–5° C. and the mixture is stirred at this temperature for an additional 1 hour. The organic layer is separated and washed with 150 mL of 1 N sulfuric acid is added, then with a solution of 10 g of sodium bicarbonate in 100 mL of deionized water and finally with 150 mL of deionized water. The organic layer is concentrated under vacuum (100–300 torr) at a temperature of 40–50° C. to ~150 mL of a slurry. Heptane (500 mL) is added and the mixture is again concentrated under vacuum (100–200 torr) at a temperature of 40–50° C. to about 300 mL of a slurry. Heptane (500 mL) is again added and the mixture is cooled to an internal temperature of 0–5° C. The solid is collected and washed with 40 mL of heptane in two equal portions of 20 mL each. The solid is dried at 60–65° C. under vacuum (10–30 torr) to obtain (R)-(5-bromoindan 2-yl)-carbamic acid methyl ester as a crystalline white solid.

A mixture of 94.55 g of (R)-(5-bromo-indan-2-yl)-carbamic acid methyl ester, 69.78 g of benzophenone imine, 2.32 g of (±)-2,2'-bis(diphenylphosphino)-1,1'-binaphthyl, 26.47 g of sodium methoxide, and 1.60 g of tris(dibenzylideneacetone)dipalladium(0) in 875 mL of deoxygenated and dry toluene is stirred under nitrogen and heated to an internal temperature of 70–75° C. over a period of 15 minutes. The mixture is stirred at this temperature for 16 hours, and cooled to 30–35° C. over a period of 30 minutes. Isopropyl acetate (875 mL) is added over a period of about 15 minutes and the mixture is further cooled to 20–25° C. Water (875 mL) is added over a period of about 15 minutes and the suspension is stirred for an additional 10 minutes. The solid is collected and washed with 175 mL of toluene followed by 263 mL of water to obtain crude (R)-[5-(diphenylmethylene)amino-indan-2-yl]-carbamic acid methyl ester as a yellow solid. The reaction flask, Buchner funnel, and filtration flask are washed with about 400 mL of isopropyl acetate and this is combined with the filtrate. The organic layer is separated and washed with a solution of 43.75 g of citric acid in 831 mL of water to afford a solution of additional crude (R)-[5-(diphenylmethylene)amino-indan-2-yl]-carbamic acid methyl ester which is added to the above crude product. 2 N Hydrochloric acid (170 mL) is added and the mixture is stirred at an internal temperature of 20–25° C. for 16 hours. Water (350 mL) is then added and the biphasic solution is stirred for an additional 10 minutes. The mixture is filtered, the aqueous layer is separated and washed with a total of 1750 mL of isopropyl acetate in two equal portions to yield about 2200 mL of a solution of (R)-(5-amino-indan-2-yl)-carbamic acid methyl ester hydrochloride. The solution is cooled to 0–5° C. over a period of 15 minutes. 2 N sodium hydroxide (2175 mL) is added to adjust the pH to 8–9 in 45 minutes while maintaining an internal temperature below 18° C. A solution of 93.5 g of sodium chloride in 267 mL of water is added and the resulting suspension is stirred at this temperature for an additional 30 minutes. The solid is collected by filtration and washed with 438 mL of water in two equal portions. The solid is dried at 55–60° C. under vacuum (10–30 torr) with nitrogen bleeding to obtain crude (R)-(5-amino-indan-2-yl)-carbamic acid methyl ester as a solid.

A mixture of crude (R)-(5-amino-indan-2-yl)-carbamic acid methyl ester, activated carbon (about 0.15 times weight of the weight of crude material) and methanol (about 20 times volume of the weight of crude material) is stirred and heated to an internal temperature at 65° C. to achieve a gentle refluxing over a period of 15 minutes. The mixture is stirred at this temperature for an additional 2 hours and filtered through celite to afford a solution of (R)-(5-aminoindan-2-yl)-carbamic acid methyl ester. The solution is concentrated under vacuum (200–400 torr) at an internal temperature of 45–55° C. to a small volume. Water is added (the ratio of methanol and water should be about 1:1). The mixture is cooled to an internal temperature of 0–5° C. The resulting suspension is filtered, the solid is washed with a precooled mixture of methanol and water (1:1; v/v) and dried at 55–60° C. under vacuum (10–30 torr) under nitrogen to yield (R)-(5-amino-indan-2-yl)-carbamic acid methyl ester.

EXAMPLE 18

(R)-6-Methyl-4'-trifluoromethylbiphenyl-2-carboxylic acid [2-(2-pyridylmethylamino)-indan-5-yl]-amide

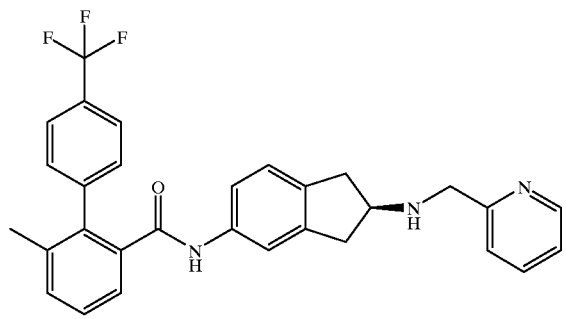

A solution of 2-bromo-3-methylbenzoic acid (21.5 g, 100 mmol) in 500 mL of methanol and 8 mL of concentrated sulfuric acid is refluxed overnight. Methanol is removed under reduced pressure, the residue is taken up in ether, washed with sodium bicarbonate, brine, and dried over magnesium sulfate, filtered, and evaporated under reduced pressure to give methyl 2-bromo-3-methylbenzoate as an oil.

A mixture of methyl 2-bromo-3-methylbenzoate (22.33 g, 97.5 mmol), potassium phosphate (82.8 g, 390 mmol), [1,1'-bis(diphenylphosphino)-ferrocene]dichloro palladium (II), complex with dichloromethane (1:1) (3.98 g, 4.87 mmol), and p-trifluoromethylphenylboronic acid (22.2 g, 117 mmol) in 500 mL of DME is degassed and refluxed under an atmosphere of argon overnight. The mixture is concentrated, poured into water and extracted with ethyl acetate. The combined organic extracts are washed with brine, dried over magnesium sulphate, filtered and evaporated under reduced pressure. The residue is purified by silica gel chromatography eluting with ethyl acetate/toluene (1:9) to give methyl 6-methyl4'-trifluoromethyl-biphenyl-2-carboxylate.

Alternatively, methyl 6-methyl-4'-trifluoromethyl-biphenyl-2-carboxylate can be prepared as follows:

To a slurry of 3-methylsalicylic acid (200 g) in 600 ml of methanol at −15° is added 65.7 g of concentrated sulfuric acid. The mixture is treated at reflux temperature for 5 days. The reaction mixture is concentrated, and methyl4-butyl ether (500 mL) and water (250 mL) are added. The ether layer is separated, washed with bicarbonate solution and evaporated to dryness to give methyl 3-methylsalicylate an oil.

A mixture of methyl 3-methylsalicylate (150 g), pyridine (178.5 g) and methylene chloride (1500 mL) is cooled to −5°. Triflic anhydride (305.6 g) is added over 30 minutes. 4-Dimethylaminopyridine (3.31 g) is then added, the reaction mixture is stirred at room temperature overnight, washed with 1N HCl, then with saturated sodium bicarbonate solution and finally with brine. The solution is dried over magnesium sulfate, and evaporated to dryness in the presence of toluene. The residual oil is disolved in toluene to obtain a volume of 3000 mL and the solution of methyl 2-trifluoromethanesulfonyloxy-3-methylbenzoate is used as is in the next step.

A solution of p-trifluoromethylbromobenzene (814.8 g) and triisopropoxyborane (681.0 g) in tetrahydrofuran (6300 mL) is cooled to −78° and n-butyllithium (2.5 m in hexanes, 1448 mL) is added over 30 minutes at a temperature below −60° to yield p-trifluoromethylphenylboronic acid.

To a solution of methyl 2-trifluoromethanesulfonyloxy-3-methylbenzoate (900 g, in toluene), potassium carbonate (629.6 g), tetrahydrofuran (2700 mL) and deionized water (5400 mL) under nitrogen is added tetrakis (triphenylphosphine) palladium (0) (104.6 g). To this is added the above solution of p-trifluoromethylphenylboronic acid and the mixture is heated at reflux for 2 days. The reaction mixture is filtered and evaporated to dryness. The residue is partitioned between water and ethyl acetate. The ethyl acetate layer is separated and evaporated to dryness. The residue is taken up in heptane-ethyl acetate (9:1), the mixture is filtered and the filtrate is evaporated to dryness to give methyl 6-methyl-4'-trifluoromethylbiphenyl-2-carboxylate as an oil.

A mixture of methyl 6-methyl-4'-trifluoromethyl-biphenyl-2-carboxylate (13.6 g, 46.3 mmol), and 1N NaOH (92.5 mL, 92.5 mmol) in 225 mL of ethanol is refluxed for 5 h. Water is added to the mixture and the aqueous layer is washed with ether. The aqueous layer is acidified with 1N HCl and extracted with ethyl acetate, dried over magnesium sulfate, filtered, and concentrated under reduced pressure. The product is purified by crystallization from ethyl acetate/hexanes to yield 6-methyl-4'-trifluoromethyl-biphenyl-2-carboxylic acid melting at 202–203° C. $^1$HNMR CDCl$_3$:300 MHz): δ 7.87 (1H, d),7.65(2H, d), 7.47(1H, d), 7.35 (1H, t), 7.25 (2H, d), 2.05(3H, s). MS m/z 279 (M−1).

To an ice bath cooled suspension of 6-methyl-4'-trifluoromethyl-biphenyl-2-carboxylic acid (17.7 g, 63.2 mmol) in 500 mL of methylene chloride is added oxalyl chloride (22.1 mL, 253 mmol) followed by 4 drops of DMF. The reaction is stirred for 2 h and another 22 mL of oxalyl chloride and 4 drops of DMF is added. Stirring is continued another 2 h. The mixture is concentrated under reduced pressure. Methylene chloride (100 mL) is added and the acid chloride is used as is in subsequent reactions.

To an ice bath cooled solution of (R)-(5-aminoindan-2-yl)-carbamic acid methyl ester (9.5 g, 46.1 mmol), ([α]$_D$=−26.29° (c=9.87 mg/mL, DMSO); mp 144–145° C.) and pyridine (4.48 mL, 55.5 mmol) in 200 mL of methylene chloride is added 6-methyl-4'-trifluoromethylbiphenyl-2-carboxylic acid chloride ( 80.5 mL of a 0.63 M solution in methylene chloride, 50.7 mmol). The reaction is stirred for 15 minutes at room temperature. The mixture is washed with 1N HCl, bicarbonate and brine. The organic layer is dried over magnesium sulfate, filtered, and concentrated under reduced pressure. The product is purified by crystallization from ethyl acetate/hexanes (1:2) to give (R)-6-methyl-4'-trifluoromethylbiphenyl-2-carboxylic acid (2-methoxycarbonylaminoindan-5-yl)-amide as a crystalline solid, mp 112–114° C. [α]$_D$=−12.85°, c=11.36 mg/mL DMS.

(R)-6-methyl-4'-trifluoromethylbiphenyl-2-carboxylic acid (2-methoxycarbonylaminoindan-5-yl)-amide (6.5 g, 13.9 mmol) is dissolved in acetonitrile (325 mL) and cooled to 0° C. under nitrogen. Iodotrimethylsilane (11.1 g, 55.6 mmol) is added dropwise, the mixture is allowed to warm to room temperature and is stirred overnight. Methanol (100 mL) is added and the mixture is stirred for 1 hour and then concentrated in vacuo. The residue is dissolved in ethyl acetate (750 mL) and washed with saturated sodium bicarbonate (2×125 mL), water (125 mL), 5% Na$_2$S$_2$O$_3$ solution (125 mL), water (125 mL), and brine (50 mL). The organic phase is dried over sodium sulfate and concentrated to afford (R)-N-(2-aminoindan-5-yl)-6-methyl-4'-trifluoromethylbiphenyl-2-carboxamide.

The amine is dissolved in methanol (160 mL), triethylamine (1.45 g, 14.4 mmol) and 2-pyridinecarboxaldehyde (1.59 g, 14.8 mmol) are added, and the mixture is stirred overnight. Polymer supported borohydride (Aldrich, borohydride on Amberlite IRA-400, 2.5 mmol/g, 6.0 g, 14.8 mmol) is added and the mixture is stirred for an additional 24 hours. The resin is removed by filtration and the filtrate is concentrated in vacuo. The residue is dissolved in a small amount of ethyl acetate and triturated with hexane to yield (R)-6-methyl4'-trifluoromethylbiphenyl-2-carboxylic acid [2-(2-pyridylmethylamino)-indan-5-yl] amide as a solid. The solid is dissolved in ethanol (100 mL) and a saturated solution of HCl (g) in ethyl ether is added. The resulting solid is collected to yield (R)-6-methyl-4'-trifluoromethylbiphenyl-2-carboxylic acid [2-(2-pyridylmethylamino)-indan-5-yl] amide hydrochloride, m.p. 281–283° C.

(b) Similarily prepared is (S)-6-methyl-4'-trifluoromethylbiphenyl-2-carboxylic acid [2-(2-pyridylmethylamino)-indan-5-yl] amide, m.p. 161–162° C.

EXAMPLE 19

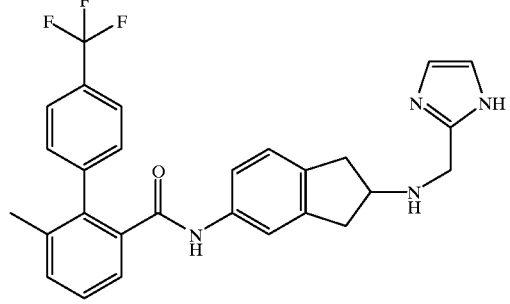

To N-(5-nitro-indan-2-yl)-acetamide (23.5 g, 107 mmol) is added 2N hydrochloric acid (500 mL). The mixture is heated to reflux for 24 h and then concentrated in vacuo. Methanol (100 mL) is added to the residue and the mixture is concentrated in vacuo. Toluene (100 mL) is added and the mixture is again concentrated. A solution of the residue in methanol (100 mL) is warmed, diethyl ether (500 mL) is added and the mixture is let stand overnight. The solid is collected by filtration and air dried to yield 2-amino-5-nitro-indane hydrochloride as a white solid.

To a solution 2-amino-5-nitro-indane hydrochloride (20.4 g, 95 mmol) in methylene chloride (500 mL) under nitrogen is added diisopropylethyl amine (14.7 g, 114 mmol). To this is added a solution of di-tert-butyldicarbonate (22.8 g, 105 mmol) in methylene chloride. The mixture is stirred for 16 h, washed with brine, 1N hydrochloric acid, brine, and then dried over sodium sulfate. The solution is concentrated in vacuo to give a solid residue which is triturated with diethyl ether to give (5-nitro-indan-2-yl)-carbamic acid tert-butyl ester as a white solid.

A solution of (5-nitro-indan-2-yl)-carbamic acid tert-butyl ester (3.52 g, 12.6 mmol) in ethanol (100 mL) is degassed and 10% palladium on carbon added. The reaction is evacuated and placed under 1 atm $H_2(g)$ for 2 h. Filtration of the reaction mixture through Celite is followed by concentration of the filtrate under reduced pressure to give (5-amino-indan-2-yl)-carbamic acid tert-butyl ester as an oil which is used directly without further purification.

To a solution of 5-amino-indan-2-yl)-carbamic acid tert-butyl ester (12.5 mmol) in methylene chloride (75 mL) is added diisopropylethyl amine (3.3 g, 25 mmol) followed by a solution of 6-methyl-4'-trifluoromethylbiphenyl-2-carboxylic acid chloride in methylene chloride (See Example 14, 12.6 mmol). After stirring 16 h, the reaction mixture is poured into ethyl acetate and washed with 1N HCl, $NaHCO_3$ solution, and brine. The organic layer is dried ($MgSO_4$) and concentrated under reduced pressure to give a solid. Recrystallization from toluene gives {5-[(6-methyl-4'-trifluoromethylbiphenyl-2-carbonyl)-amino]-indan-2-yl}-carbamic acid terf-butyl ester.

A solution of {5-[(6-methyl-4'-trifluoromethylbiphenyl-2-carbonyl)-amino]-indan-2-yl}-carbamic acid tert-butyl ester (5.19 g,10.5 mmol) in formic acid (40 mL) is heated to 40° C. with stirring. After 3 h, the reaction mixture is cooled to room temperature and stirring is continued for 16 h. The reaction mixture is concentrated under reduced pressure and the resulting oil dissolved in ethyl acetate. The organic layer is washed with 8% $NaHCO_3$ solution until the aqueous layer remains basic at which point a precipitate forms in the organic layer. The precipitate is collected by filtration to give 6-methyl-4'-trifluoromethylbiphenyl-2-carboxylic acid (2-amino-indan-5-yl)-amide.

Imidazole-2-carboxaldehyde (2.45 g, 25.5 mmol) is added to a solution of 6-methyl-4'-trifluoromethyl-biphenyl-2-carboxylic acid (2-amino-indan-5-yl)-amide hydrochloride (11.1 g, 24.9 mmol) and triethylamine (5.05 mL, 50.0 mmol) in methanol (500 mL). The mixture is stirred at room temperature for 16 hours. Polymer supported borohydride (Aldrich, borohydride on Ambelite IR-400, 2.5 mmol/g, 10.0 g, 25.0 mmol) is added, the mixture stirred for 2 hours, filtered and concentrated under reduced pressure. The residue is taken up in ethanol (100 mL) and a saturated solution of hydrochloric acid gas in diethyl ether (10 mL) is added. The white precipitate is collected to yield 6-methyl-4'-trifluoromethylbiphenyl-2-carboxylic acid [2-(2-imidazolylmethylamino)-indan-5-yl] amide hydrochloride m.p. 240–242° C. Free base has m.p. 169–170° C.

EXAMPLE 20

The following compounds are prepared similarly to the previous example, starting from racemic (5-aminoindan-2-yl)-carbamic acid methyl ester.

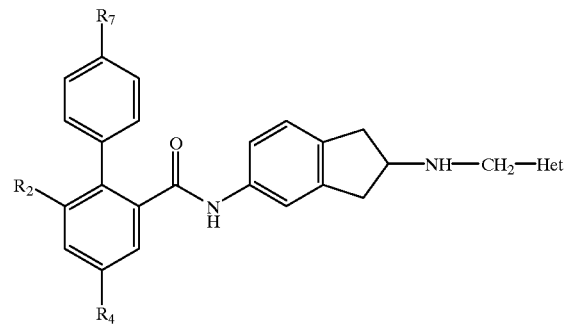

| COMPOUND | $R_2$ | $R_4$ | $R_7$ | Het | mp (° C.) |
|---|---|---|---|---|---|
| (a) | $CH_3$ | H | $CF_3$ | 3-thienyl | >230* |
| (b) | $CH_3$ | $CH_3$ | $CF_3$ | 2-thienyl | 252–254* |
| (c) | $CH_3$ | $CH_3$ | $CF_3$ | 3-thienyl | 232–234* |
| (d) | $CH_3$ | H | $CF_3$ | 2-(1-methyl-pyrrolyl) | 60–63 |
| (e) | H | $CH_3$ | $CF_3$ | 2-pyridyl | 155–156 |
| (f) | $CH_3$ | H | $CF_3$ | 2-pyridyl | 167–168 |
| (g) | $CH_3$ | H | $CF_3$ | 4-pyridyl | 188–190* |
| (h) | $CH_3$ | H | $CF_3$ | 6-methyl-2-pyridyl | 138–139 |
| (i) | $CH_3$ | H | $CF_3$ | 2-quinolyl | 158–159 |
| (j) | $CH_3$ | H | $CF_3$ | 1-methyl-2-imidazolyl | 116–119 |
| (k) | $CH_3$ | H | $CF_3$ | 2-thiazolyl | 167–168 |
| (l) | $CH_3$ | H | $CF_3$ | 3-pyridyl | 187–188* |

*2-naphthalenesulfonate salt

EXAMPLE 21

6-Methyl-4'trifluoromethylbiphenyl-2-carboxylic acid (7-(2-pyridylmethylamino)-6,7,8,9-tetrahydro-5H-benzocyclohepten-2-yl)-amide

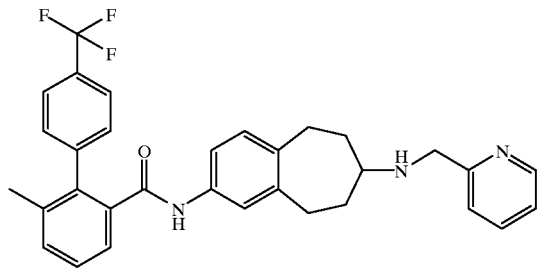

To 6,7,8,9-tetrahydro-5H-benzocyclohepten-7-one (2.56 g, 16 mmol) and hydroxylamine hydrochloride (2.2 g, 32 mmol) in 27 mL of water is slowly added a solution of sodium carbonate (1.69 g, 16 mmol) in 14 mL of water. The mixture is stirred overnight. The solid is then filtered off, washed with water, and dried at 50° C. under reduced pressure to give 6,7,8,9-tetrahydro-N-hydroxy-5H-benzocyclohepten-7-amine as a white solid.

To a suspension of $NaBH_4$ (1.98 g, 52.3 mmol) in 40 mL of DME cooled in an ice-bath is added $TiCl_4$. To this mixture is added the above compound (2.3 g, 13.1 mmol) in 28 mL of DME dropwise. The mixture is stirred overnight, poured into ice water (135 mL), basified with 28% ammonia (20 mL) and extracted with ethyl acetate. The organic extracts are dried over magnesium sulfate, filtered and concentrated under reduced pressure to give 6,7,8,9-tetrahydro-5H-benzocyclohepten-7-amine as an oil.

The amine is treated with methyl chloroformate, nitrated, reduced, acylated with 6-methyl-4'-chlorobiphenyl-2-carboxylic acid chloride, then N-deprotected and treated with 2-pyridinecarboxaldehyde under conditions similar to those described above for indane derivatives to give the title compound; m.p. 104–106° C.

EXAMPLE 22

To a solution of N-(2-aminoindan-5-yl)-6-methyl-4'-trifluoromethylbiphenyl-2-carboxamide (0.3 g, 0.73 mmol) in methylene chloride (3 mL) is added 3-thiophene carboxaldehyde (0.068 mL, 0.73 mmol) and sodium triacetoxyborohydride (0.2 g, 0.95 mmol). The mixture is stirred for 3 hours and then washed with brine. The organic phase is dried over magnesium sulfate and concentrated in vacuo. The residue is purified by flash chromatography ($SiO_2$; hexane/ethyl acetate) to give 6-methyl-4'-trifluoromethylbiphenyl-2-carboxylic acid [2-(2-di(thienylmethyl)amino)indan-5-yl] amide as a white foam, mp 58–64° C.

EXAMPLE 23

To a solution of 6-methyl-4'-trifluoromethylbiphenyl-2-carboxylic acid [2-(2-pyridylmethylamino)-indan-5-yl] amide (the compound of Example 20f, 0.4 g, 0.8 mmol) in methylene chloride (5 mL) is added triethylamine (0.12 g, 1.15 mmol) and paraformaldehyde (0.024 g, 0.8 mmol). The mixture is stirred for two hours and then sodium triacetoxyborohydride (0.24 g, 1.12 mmol) is added. The mixture is stirred overnight and then washed with dilute sodium bicarbonate, dried over sodium sulfate, and evaporated. The residue is purified by flash chromatography ($SiO_2$; ethyl acetate) to afford 6-methyl-4'-trifluoromethylbiphenyl-2-carboxylic acid [2[(2-pyridylmethyl)(methyl)amino]-indan-5-yl] amide as a white solid, mp 105–115°.

EXAMPLE 24

6-Methyl-4'-trifluoromethyl-biphenyl-2-carboxylic acid

A. 3-Methylsalicylic acid is esterified to methyl 3-methylsalicylate by reaction under reflux for about 48 hours with methanol in the presence of trimethyl orthoformate (4.0 moles) and concentrated sulfuric acid (1.1 moles) while removing by distillation the generated methyl formate and replacing the methanol which is lost by distillation. The reaction mixture is then evaporated to dryness at 40° under vacuum and toluene is added. The toluene solution is washed with water, then 20% aqueous potassium bicarbonate solution and saturated sodium chloride solution. The toluene solution is filtered through neutral activated aluminum oxide and evaporated to dryness to yield methyl 3-methylsalicylate as a liquid.

B. To a solution of 1.0 mole of methyl 3-methylsalicylate in toluene are added 2.33 moles of 4-methylmorpholine and 0.022 moles of 4-dimethylaminopyridine. The resulting solution is then treated with 1.07 moles of trifluoromethanesulfonic acid anhydride (triflic anhydride) at −15° C. The reaction mixture is stirred overnight at −3 to −4° C. and washed consecutively with 3.7% aqueous HCl, 20% potassium bicarbonate solution and saturated sodium chloride solution. The toluene solution is then filtered through alumina and evaporated to dryness at less than 50° C. and about 40 mmHg pressure. The residue is distilled at 50° C. and 5 mmHg pressure to obtain methyl 3-methyl-2-trifluoromethanesulfonyloxybenzoate as an oil.

C. A solution of 140.75 g of 4-bromobenzotrifluoride and 117.6 g of triisopropylborate in 1050 mL of dry and peroxide-free THF is cooled to −72±3° C. 275 mL of 2.5 M n-BuLi solution in hexane are slowly added over a period of 90 minutes at such a rate that the internal temperature of the reaction mixture remains below −60° C. The mixture is stirred at −65 to −70° C. for 30 minutes after the addition and warmed to 0° C. over 90 minutes. This solution of diisopropyl 4-trifluoromethylphenylboronate is used as is in the next step.

A solution of 155 g of methyl 3-methyl-2-trifluoromethylmethanesulfonyloxybenzoate, 107.8 g of potassium carbonate in 467.5 mL of THF and 935 g of deionized water is stirred under nitrogen for 20 minutes. 15.0 g of Tetrakis(triphenylphosphine)palladium (0) and ~1610 mL of boronate solution from step above are added and the reaction mixture is heated under gentle reflux (~64° C.) for 16 hours. The reaction mixture is cooled to room temperature and filtered through a pad of 40 g of the filter agent Celite® 521. The filter cake is washed with 100 mL of THF and the total filtrate is partially evaporated under reduced pressure (110–120 mbar/40° C.) to remove about 1500 mL of distillate and obtain a three phase mixture (about 1250 mL). 500 mL of t-Butyl methyl ether and 200 mL of 2% sodium chloride solution are added. The mixture is stirred for 5 minutes and filtered through a pad of 40 g of Filter agent, Celite® 521 and the filter cake is washed with 100 mL of t-butyl methyl ether. The top organic layer (1100 mL) is separated from the bottom aqueous layer (950 mL). The bottom aqueous layer (950 mL) is extracted with 300 mL of t-butyl methyl ether. The combined upper organic phases are washed with 300 mL of 2% sodium chloride solution and evaporated under reduced pressure (28 mbar/40° C.) to obtain methyl 6-methyl-4'-trifluoromethyl-biphenyl-2-carboxylate.

D. 6N Sodium hydroxide (260 mL) is added slowly at room temperature to a solution of 183 g of methyl 6-methyl-4'-trifluoromethyl-biphenyl-2-carboxylate in 1200 mL of methanol. The reaction mixture is heated under gentle reflux for 2.5 hours, cooled to room temperature and diluted with 300 mL of water. The reaction mixture is evaporated under reduced pressure (110–120 mbar/40° C.) to a suspension of about 750 mL which is filtered through the filter agent Celite® 521, and the filter cake is washed sequentially with 250 mL of water and 250 mL of heptane. The organic layer is separated and the aqueous layer is washed with 250 mL of heptane. The aqueous layer is acidified with 500 mL of 4N hydrochloric acid and extracted with ethyl acetate. The ethyl acetate extract is washed with water and filtered through the filter agent Celite® 521. The ethyl acetate solution (ca. 1000 mL) is evaporated under reduced pressure (110–120 mbar/40° C.) to a volume of 600 mL to which is added heptane (3125 mL). The suspension is then heated to reflux until a clear solution is obtained, the solution is cooled to 0° C. and the resulting solid is filtered off to yield 6-methyl-4'-trifluoromethyl-biphenyl-2-carboxylic acid.

EXAMPLE 25

Hard gelatin capsules, comprising 100 mg active substance,can be prepared for example as follows:

| Composition (for 1000 capsules) | |
|---|---|
| Active ingredient | 100.0 g |
| Lactose | 250.0 g |
| Microcrystalline cellulose | 30.0 g |
| Sodium lauryl sulfate | 2.0 g |
| Magnesium stearate | 8.0 g |

The sodium lauryl sulfate is added to the lyophilized active ingredient via a sieve with a mesh size of 0.2 mm. Both components are intimately mixed. Then first the lactose is added via a sieve with a mesh size of 0.6 mm and then the microcrystalline cellulose via a sieve with a mesh size of 0.9 mm. Thereupon these components are intimately mixed for a further 10 minutes. Finally the magnesium stearate is added via a sieve with a mesh size of 0.8 mm. After 3 minutes of further mixing, the formulation is filled into hard gelatin capsules of size 0 (390 mg each).

What is claimed is:

1. A compound of the formula

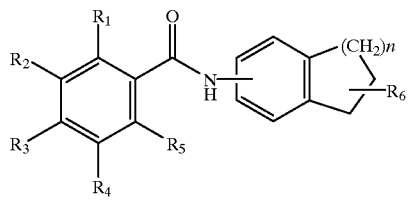

(I)

wherein $R_2$—C, $R_3$—C, $R_4$—C or $R_5$—C may be replaced by N; and wherein n is 1, 2 or 3;

$R_1$ is aryl, cycloalkyl or heterocyclyl;

$R_2$, $R_3$, $R_4$ and $R_5$ are independently hydrogen, alkyl, substituted alkyl, halo, amino, substituted amino, trifluoromethyl, cyano, carboxyl, alkoxycarbonyl, aralkoxycarbonyl, (alkyl, aryl or aralkyl)-thio, (alkyl, aryl or aralkyl)-oxy, acyloxy, (alkyl, aryl or aralkyl)-aminocarbonyloxy; or any two of $R_2$, $R_3$, $R_4$ and $R_5$ at adjacent positions are alkylenedioxy;

$R_6$ is amino, substituted amino, acylamino,

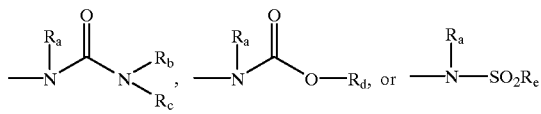

wherein $R_a$ is hydrogen or optionally substituted alkyl, $R_b$ and $R_c$ are independently hydrogen, optionally substituted alkyl, cycloalkyl, aryl or heterocyclyl; or $R_b$ and $R_c$ together represent lower alkylene or lower alkylene interrupted by O, S, or N—(H, alkyl or aralkyl);

$R_d$ is optionally substituted alkyl, cycloalkyl, aryl or heterocyclyl; and $R_e$ is optionally substituted alkyl, aryl, heterocyclyl, cycloalkyl, amino or substituted amino; the variable $R_6$ being located on the 5-, 6- or 7-membered saturated ring at a position not directly adjacent to the ring junction;

or a pharmaceutically acceptable salt thereof; or an enantiomer thereof.

2. A compound according to claim 1 of the formula

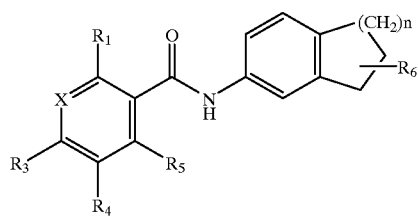

Ia wherein n is 1, 2, or 3;

$R_1$ is aryl, cycloalkyl or heterocyclyl;

X is $R_2$—C or N;

$R_2$, $R_3$, $R_4$ and $R_5$ are independently hydrogen, optionally substituted alkyl, halo, amino, substituted amino, trifluoromethyl, cyano, carboxyl, alkoxycarbonyl, aralkoxycarbonyl, (alkyl, aryl or aralkyl)-thio, (alkyl, aryl or aralkyl)-oxy, acyloxy, (alkyl, aryl or aralkyl)-aminocarbonyloxy; or any two of $R_2$, $R_3$, $R_4$ and $R_5$ at adjacent positions are alkylenedioxy;

$R_6$ is amino, substituted amino, acylamino,

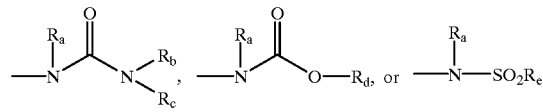

wherein $R_a$ is hydrogen or optionally substituted alkyl, $R_b$ and $R_c$ are independently hydrogen, optionally substituted alkyl, cycloalkyl, aryl or heterocyclyl; or $R_b$ and $R_c$ together represent lower alkylene or lower alkylene interrupted by O, S, or N—(H, alkyl or aralkyl);

$R_d$ is optionally substituted alkyl, cycloalkyl, aryl or heterocyclyl; and $R_e$ is optionally substituted alkyl, aryl, heterocyclyl, cycloalkyl, amino or substituted amino; the variable $R_6$ being located on the 5-, 6- or 7-membered saturated ring at a position not directly adjacent to the ring junction;

or a pharmaceutically acceptable salt thereof; or an enantiomer thereof.

3. A compound according to claim 2 of the formula

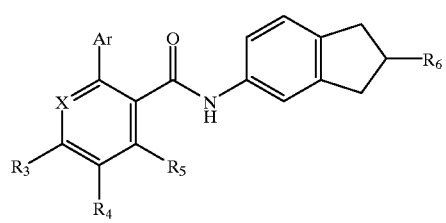

Ib wherein Ar is monocyclic aryl or heteroaryl; X is $R_2$—C or N; and $R_2$, $R_3$, $R_4$ and $R_5$ are independently hydrogen, lower alkyl, halo, trifluoromethyl, cyano, or lower alkoxy; and $R_6$ has meaning as defined in claim 2; or a pharmaceutically acceptable salt thereof; or an enantiomer thereof.

4. A compound according to claim 1 of formula I wherein $R_2$—C, $R_3$—C, $R_4$—C or $R_5$—C may be replaced by N; and wherein n is 1, 2 or 3;

$R_1$ is phenyl or thienyl which in each case is unsubstituted or substituted by a substituent selected from the group consisting of lower alkyl, lower alkoxy, halo, trifluoromethyl, cyano, and trifluoromethoxy;

$R_2$, $R_3$, $R_4$ and $R_5$ are independently hydrogen, lower alkyl, lower alkoxy, halo, trifluoromethyl, amino, lower alkylamino, di-lower alkyl amino, or lower alkanoyl-amino;

$R_6$ is amino, phenyl-lower alkyl-amino, lower alkanoyl-amino, lower alkanoyl-amino in which the alkyl group of the alkanoyl group is substituted by phenyl, by lower alkoxy, by phenoxy, by lower alkylthio, by phenylthio, by di-lower alkylamino, by morpholino, by thiomorpholino, by piperazino, or by 4-lower alkyl-piperazino, or is N-methyl-N'-lower alkanoyl-amino, benzoyl-amino, or isoxazolylcarbonyl-amino in which isoxazoyl is unsubstituted or substituted by lower alkyl, or is

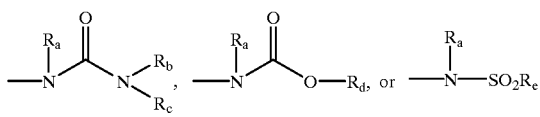

wherein $R_a$ is hydrogen or alkyl, $R_b$ and $R_c$ are independently hydrogen, lower alkyl, 5- to 7-membered cycloalkyl, or phenyl; or $R_b$ and $R_c$ together are morpholino, thiomorpholino or lower alkylene;

$R_d$ is lower alkyl, lower alkyl substituted by lower alkoxy, by lower alkoxy-lower alkoxy, by morpholino, by thiomorpholino, by 2-oxo-1-pyrrolidino, by pyridyl, by phenyl, or by phenyl which is substituted by a substituent selected from halo, trifluoromethyl, lower alkyl, and lower alkoxy, or is phenyl, phenyl substituted by substituent selected from halo, trifluoromethyl, lower alkyl, and lower alkoxy, or is 5- to 7-membered cycloalkyl, or pyranyl; and $R_e$ is lower alkyl, phenyl-lower alkyl, phenyl which is unsubstituted or substituted by a group selected from lower alkyl, lower alkoxy, halo, trifluoromethyl, and lower alkane-sulphonyl, or is naphthyl, thienyl, furyl, isoxazolyl, imidazolyl or quinolinyl each of which is unsubstituted or substituted by a group selected from lower alkyl, halo and trifluoromethyl, or is lower alkyl-amino, di-lower alkyl-amino or 5- to 7-membered cycloalkyl-amino; or a pharmaceutically acceptable salt thereof; or an enantiomer thereof.

5. A compound according to claim 3 of the formula

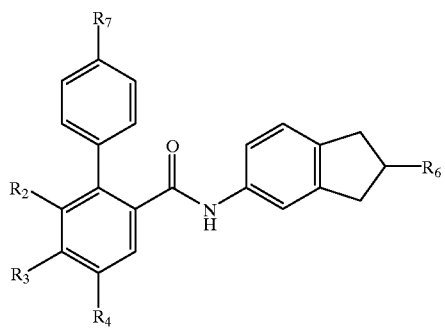

wherein $R_2$, $R_3$ and $R_4$ are independently hydrogen, $C_1$–$C_4$-alkyl, $C_1$–$C_4$-alkoxy, trifluoromethyl, chloro or fluoro; $R_7$ is trifluoromethyl, chloro or cyano; and $R_6$ is

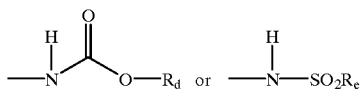

wherein $R_d$ is $C_1$–$C_4$-alkyl; and $R_e$ is $C_1$–$C_4$-alkyl, monocyclic carbocyclic aryl or heterocyclic aryl; or an enantiomer thereof.

6. A compound according to claim 5 wherein $R_2$ is methyl; $R_3$ is hydrogen; $R_4$ is hydrogen or methyl; $R_6$ is

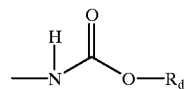

wherein $R_d$ is methyl; and $R_7$ is trifluoromethyl; or an enantiomer thereof.

7. A compound according to claim 5 which is selected from the (S)-enantiomer wherein $R_2$ is methyl; $R_3$ and $R_4$ are hydrogen; $R_e$ is methyl; and $R_7$ is trifluoromethyl;

the (S)-enantiomer wherein $R_2$ is methyl; $R_3$ and $R_4$ are hydrogen; $R_e$ is 2-thienyl; and $R_7$ is trifluoromethyl;

the (S)-enantiomer wherein $R_2$ and $R_4$ are methyl; $R_3$ is hydrogen; $R_e$ is 2-thienyl; and $R_7$ is trifluoromethyl; and the (R)-enantiomer wherein $R_2$ is methyl; $R_3$ and $R_4$ are hydrogen; $R_d$ is methyl; and $R_7$ is trifluoromethyl.

8. A compound according to claim 6 which is the (R)-enantiomer wherein $R_2$ is methyl; $R_3$ and $R_4$ are hydrogen; $R_d$ is methyl; and $R_7$ is trifluoromethyl.

9. A pharmaceutical composition comprising a compound of claim 1 and one or more pharmaceutically acceptable carriers.

10. A method of inhibiting microsomal triglyceride transfer protein in a mammal which comprises administering to a mammal in need thereof an effective microsomal triglyceride transfer protein inhibiting amount of a compound of claim 1.

11. A method of decreasing apolipoprotein B secretion in a mammal which comprises administering to a mammal in need thereof an effective apolipoprotein B secretion inhibiting amount of a compound of claim 1.

12. A method of treating microsomal triglyceride transfer protein or lipoprotein B dependent conditions in mammals which comprises administering to a mammal in need thereof an effective amount of a compound of claim 1.

13. A method according to claim 12 of treating atherosclerosis, hypertriglyceridemia or hypercholesteremia.

14. A method of preparing an enantiomer of a compound of formula Ib of claim 3 which comprises:
   (a) reducing (1S-trans)- or (1R-trans)-hydroxy-2-amino-6-nitroindane wherein the amino group is in protected form to the corresponding (R) or (S)-enantiomer of 2,6-diaminoindane in which the 2-amino group is in protected form;
   (b) condensing said (R) or (S) enantiomer with a reactive derivative of carboxylic acid substituted according to formula Ib and optionally removing the amino protecting group to obtain the (R) or (S) enantiomer of a compound of the formula

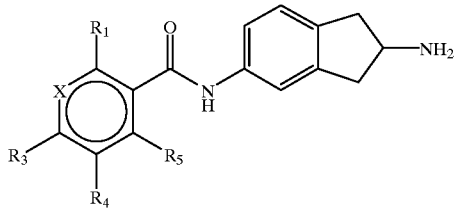

V (c) and subsequently N-derivatizing a said compound to a compound of formula Ib wherein $R_6$ is derivatized amino as defined in said claim.

15. A method for the preparation of an enantiomer of the compound of formula Ib, which comprises:
   (a) resolving 5-bromo-2-aminoindane with either (R) or (S)-10-camphorsulfonic acid to obtain either chiral (R)- or (S)-5-bromo-2-aminoindane;
   (b) protecting the resulting (R)- or (S)-5-bromo-2-aminoindane with an N-alkoxycarboxyl protecting group;
   (c) reacting a said N-alkoxycarbonyl-5-bromo-2-aminoindane with benzophenone imine under conditions of a Buchwald condensation;
   (d) cleaving the resulting 5-benzophenoneimine derivative by catalytic hydrogenation or treatment with acid;
   (e) condensing the resulting 2-protected amino-5-aminoindane with a reactive derivative of a carboxylic acid, of the formula III wherein $R_1$ is aryl or heterocyclic aryl and $R_3$–$R_5$ and X have meaning as defined herein, and optionally removing the amino protecting group to obtain the corresponding (R) or (S) enantiomer of a compound of formula V

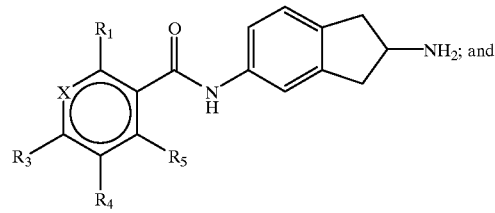

V f) N-derivatizing a said compound to obtain a compound of formula Ib wherein $R_6$ is derivatized amine as defined.

16. A process for the preparation of (R)-2-amino-5-bromoindane from racemic 2-amino-5-bromoindane which comprises reacting racemic 2-amino-5-bromoindane with 1(S)-10-camphorsulfonic acid, selectively crystallizing and purifying the (R, S) salt, and liberating with base (R)-2-amino-5-bromoindane which is substantially free of the (S)-isomer.

* * * * *